(12) United States Patent
Tunac

(10) Patent No.: US 9,212,201 B2
(45) Date of Patent: Dec. 15, 2015

(54) ANTIFUNGAL AND ANTIPARASITIC POLYENE MACROLIDES

(75) Inventor: Josefino B. Tunac, Oxford, MI (US)

(73) Assignee: ACEA Biotech, Inc., San Francisco, CA (US)

( * ) Notice: Subject to any disclaimer, the term of this patent is extended or adjusted under 35 U.S.C. 154(b) by 0 days.

(21) Appl. No.: 13/811,895

(22) PCT Filed: Jul. 22, 2011

(86) PCT No.: PCT/US2011/045112
§ 371 (c)(1),
(2), (4) Date: Jan. 23, 2013

(87) PCT Pub. No.: WO2012/012782
PCT Pub. Date: Jan. 26, 2012

(65) Prior Publication Data
US 2013/0123205 A1    May 16, 2013

Related U.S. Application Data

(60) Provisional application No. 61/367,107, filed on Jul. 23, 2010.

(51) Int. Cl.
*A61K 31/70*     (2006.01)
*C07H 17/08*     (2006.01)
*A61K 31/7048*   (2006.01)
*C07D 493/08*    (2006.01)
*A61K 9/00*      (2006.01)
*A61K 9/08*      (2006.01)
*A61K 9/20*      (2006.01)

(52) U.S. Cl.
CPC .............. *C07H 17/08* (2013.01); *A61K 9/0014* (2013.01); *A61K 9/0019* (2013.01); *A61K 9/0034* (2013.01); *A61K 9/08* (2013.01); *A61K 9/205* (2013.01); *A61K 9/2045* (2013.01); *A61K 31/7048* (2013.01); *C07D 493/08* (2013.01)

(58) Field of Classification Search
CPC ........................... C07H 17/08; A61K 31/7048
USPC ............................................. 536/6.5; 514/31
See application file for complete search history.

(56) References Cited

U.S. PATENT DOCUMENTS

| 2,908,611 | A | * | 10/1959 | Dutcher et al. ............... 424/119 |
| 3,476,856 | A |   | 11/1969 | Kulbach et al. |
| 3,928,570 | A |   | 12/1975 | Metzger |
| 5,000,958 | A | * | 3/1991  | Fountain et al. .............. 424/450 |
| 5,646,114 | A | * | 7/1997  | Lambert, Jr. .................. 514/4.4 |
| 6,514,945 | B1 | * | 2/2003 | Boettner .......................... 514/29 |
| 6,846,837 | B2 | * | 1/2005 | Maibach et al. .............. 514/350 |
| 2003/0235541 | A1 | | 12/2003 | Maibach et al. |
| 2006/0293216 | A1 | * | 12/2006 | Klaveness et al. ................ 514/2 |

FOREIGN PATENT DOCUMENTS

| DE | 2255224 A1 | 6/1973 |
| DE | 2417993 A1 | 10/1975 |
| WO | WO 2004/069230 A1 | 8/2004 |
| WO | WO 2007/063335 A2 | 6/2007 |

OTHER PUBLICATIONS

Beezer, A., et al., "The Synthesis and Characterisation of Polyene Complexes with Divalent Metal Ions: Mg(II), Ca(II), Ni(II), Cu(II) and Zn(II)," Inorganica Chimica Acta, 1985, pp. 117-122, vol. 108.
Beezer, A., et al., "Stability Constants for, and Structural Investigation of, Divalent Metal Ion Complexes with Polyene Antibiotics," 1985, pp. 123-127, vol. 108.
Database CA [Online] Chemical Abstracts Service, Columbus, Ohio, US; Delektorskii, V. V. et al: "Comparative electron microscopy study of changes in the ultrastructure of amphoglucamine", XP082717376,retrieved from STN Database accession No. 1982:466028 & Delektorskii, V. V. et al: "Comparative electron microscopy study of changes in the ultrastructure of amphoglucamine", Meditsinskaya Parazitologiya I Parazitarnye Bolezni, 51(2), 62-5, 3 Plates Coden: MPPBAB; ISSN: 0025-8326, 1982, 1 Page.
Database CA [Online] Chemical Abstracts Service, Columbus, Ohio, US; Lyubimova, L. K. et al: "Antiamebic activity of polyenic antibiotics", XP002717377, retrieved from STN Database accession No. 1985:182317 & Lyubimova, L. K. et al: "Antiamebic activity of polyenic antibiotics", Antibiotiki Meditsinskaya Biotekhnologiya, 30(3), 179-82 Coden: AMBIEH; ISSN: 0233-7525, 1985, 2 Pages.
Database CA [Online] Chemical Abstracts Service, Columbus, Ohio, US; "Pharmaceutical composition containing meglumine complexes of fungicidal polyene antibiotic-macrolides", XP002717378, retrieved from STN Database accession No. 1976:410426 & NL 7 405 072 NL (Leningrad Scientific-Research Institute of Antibiotics, USSR) Apr. 16, 1974, 4 Pages.
Database CA [Online] Chemical Abstracts Service, Columbus, Ohio, US; Metzger, Julio: 11 Water-soluble amphotericin B complexes 11, XP002717379, retrieved from STN Database accession No. 1973:453751 DE 2255224 A1, Jun. 17, 1973, Squibb & Son Inc., 6 Pages.
Supplementary European Search Report for European Patent Application No. EP 11810502.2, Jan. 20, 2014, 11 Pages.
Gilead Sciences, Inc., AmBisome-Product Information, Revised: Oct. 2008, 28 Pages, Archived on web.archive.org on Sep. 17, 2010, Can be retrieved from the internet <URL:http://web.archive.org/web/20100915000000*/http://www.astellas.us/docs/ambisome.pdf>.

(Continued)

*Primary Examiner* — Elli Peselev
(74) *Attorney, Agent, or Firm* — Weaver Austin Villeneuve & Sampson LLP

(57) ABSTRACT

In certain aspects, the present disclosure provides for novel, water-soluble polyene macrolides and salts or solvates thereof and methods of making the water-soluble polyene macrolides. Also provided are compositions and methods for inhibiting, preventing, and/or treating fungal and parasitic diseases in a subject.

18 Claims, 30 Drawing Sheets

(56) References Cited

OTHER PUBLICATIONS

Graybill, A., "Lipid Formulations for Anphotericin B: Does the Emperor Need New Clothes?" Annals of Internal Medicine, 1996, pp. 921-923, vol. 1245.

Khoo, S.H., et al., Administering amphotericin B-a practical approach, The Journal of Antimicrobial Chemotherapy, 1994, pp. 203-213, vol. 33.

Meyerhoff, A., "U.S. Food and Drug Administration Approval of AmBisome (Liposomal Amphotericin B) for Treatment of Visceral Leishmaniasis," Clinical Infectious Diseases, Jan. 1999, pp. 42-48, vol. 28.

PCT International Search Report and Written Opinion, PCT/US2011/045112, Dec. 12, 2011, 10 Pages.

Reuter, S., et al., "Salvage Treatment with Amphotericin B in Progressive Human Alveolar Echinococcosis," Antimicrobial Agents and Chemotherapy, Nov. 2003, p. 3586-3591, vol. 47, No. 11.

Tollemar, J., et al., "Liposomal Amphotericin B Prevents Invasive Fungal Infections in Liver Transplant Recipients," Transplantation, Jan. 15, 1995, pp. 45-50, vol. 59, No. 1.

Zotchev, S., "Polyene Macrolide Antibiotics and their Applications in Human Therapy," Current Medicinal Chemistry, 2003, pp. 211-223, vol. 10, No. 3.

European Office Action dated Oct. 14, 2014 issued in 11 810 502.2.
European Office Action dated Apr. 17, 2015 issued in 11 810 502.2.

\* cited by examiner

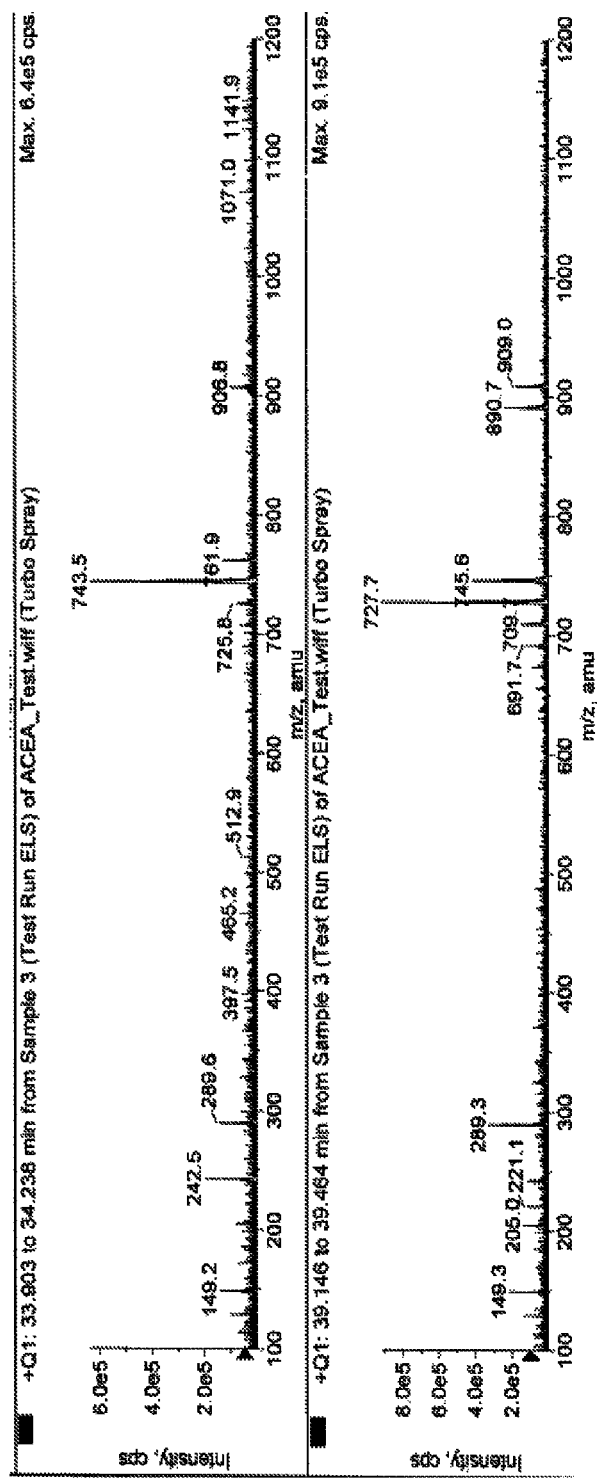
Figure 2 (con't)

Figure 3 (con't)
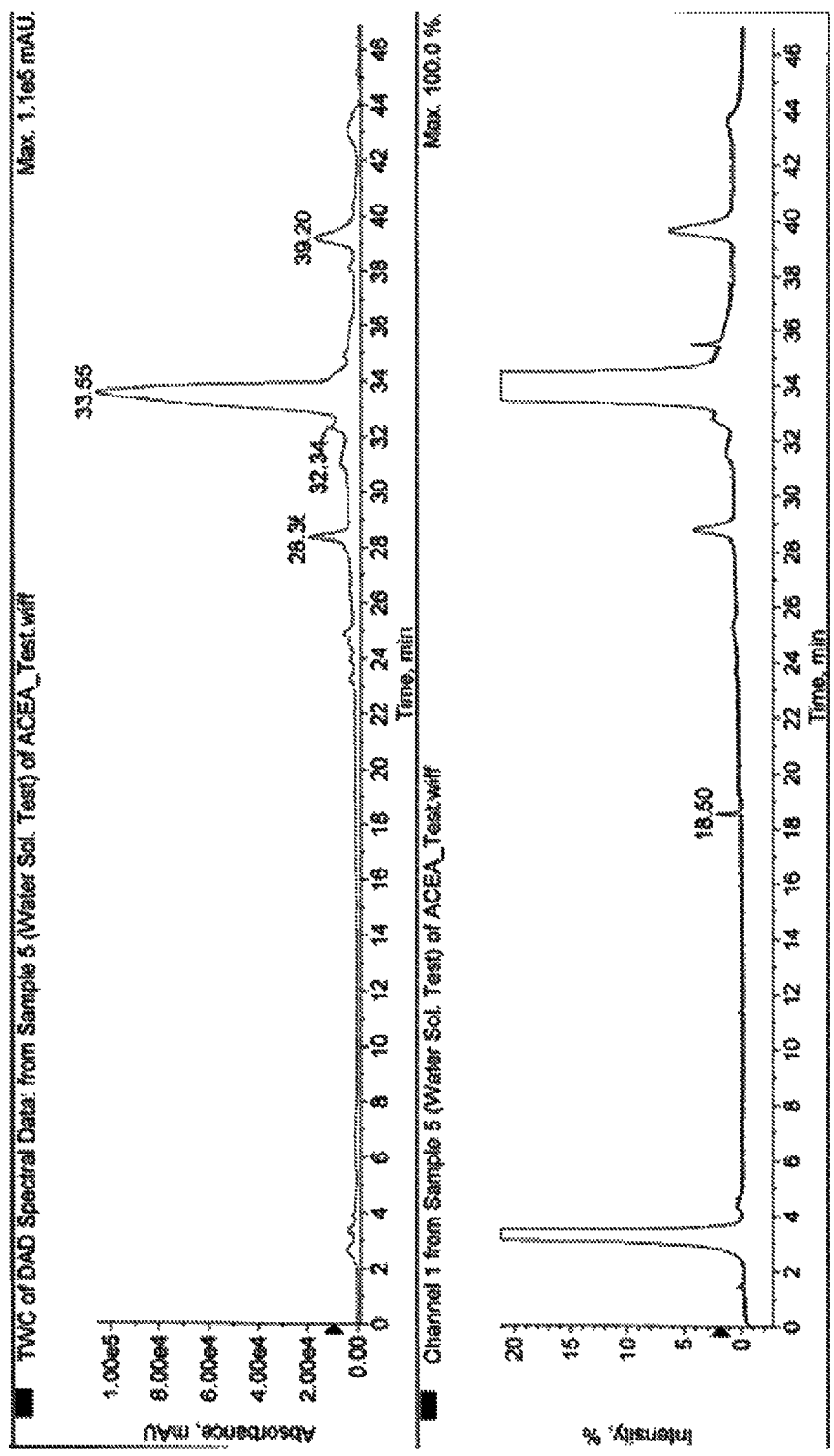

Figure 6

Single Mass Analysis
Tolerance = 5.0 PPM   /   DBE: min = -1.5, max = 50.0
Selected filters: None Monoisotopic Mass, Even Electron Ions
114 formula(e) evaluated with 2 results within limits (up to 50 closest results for each mass)
Elements Used:
C: 40-60   H: 60-90   N: 0-2   O: 10-30
0.01 mg-ml in FA buffer
Set mass: 0.0   CE: 20.0
Cone Voltage: 5.0
Confungin MS Pos 25 (1.209) Cm (1:52)

HAB229
15825.000000000

1: TOF MS ES+
8.16e4

| Minimum: | | | -1.5 | |
| Maximum: | | 5.0 | 5.0 | 50.0 |

| Mass | Calc. Mass | mDa | PPM | DBE | i-FIT | Formula |
|---|---|---|---|---|---|---|
| 924.4987 | 924.5015 | -2.8 | -3.0 | 2.5 | 563.2 | C40 H78 N O22 |
| | 924.4957 | 3.0 | 3.2 | 11.5 | 166.5 | C47 H74 N O17 |

(a) Na adduct:

(b) K adduct:

ANTIFUNGAL AND ANTIPARASITIC POLYENE MACROLIDES

RELATED APPLICATIONS

This application is the 35 USC §371 national stage entry of PCT/US2011/045112 and claims the benefit of U.S. Provisional Application Ser. No. 61/367,107 filed Jul. 23, 2010, which is hereby incorporated by reference in its entirety for all purposes.

FIELD

The present disclosure relates to novel water-soluble polyene macrolides having broad spectrum antifungal and antiparasitic activity and other beneficial properties. The present disclosure also relates to pharmaceutical compositions and therapeutic methods involving administering such compounds and compositions.

BACKGROUND

The incidence of fungal infections and the emergence of opportunistic fungal infections are increasing (Hajjeh et al., J Clin Microbiol, 42:1519-1527 (2004); Walsh et al., Clin Microbiol Infect, 10 (Suppl.1):48-66 (2004)). The increase in immunocompromised patients due to diseases (e.g., AIDS, cancer, organ transplants), and use of medical devices (Kojic et al., Clin Microbiol Rev, 17(2):255-267 (2004)) contribute to the substantial increase in the occurrence of serious fungal infections. The limited number of effective and non-toxic antifungals and the emergence of resistance highlight the need for alternative antifungals. For example, candidiasis is a major nosocomial infection in immunocompromised patients and the most common hospital-acquired mycosis (Rees et al., Clin Infect Dis, 27:1138-1147 (1998)). Griseofulvin, introduced in 1958, was the first available drug for the treatment of severe systemic mycoses; amphotericin B was introduced in 1960 and remains the mainstay therapy for serious *Candida* infections (Gupta et al., J Am Acad Dermatol, 30:677-698 (1994)). However, the clinical utility of Amphotericin B is hampered by dose-limiting nephrotoxicity (Sabra et al., Drug Saf, 5:94-108 (1990); Dismukes, Clin Infect Dis, 30:653-657 (2000)). Fluconazole provides new options for invasive candidiasis, but the emergence of resistance poses some problems (Müller et al., J Antimicrob Chemother, 46:338-341 (2000)).

Thus, new classes of antifungal agents such as the candins (pneumocandins, echinocandins), the nikkomycins, and the pradamicins-benanomicins were developed (Ghannoum et al., Clin Microbiol Rev, 12:501-517 (1999)). The echinocandins are semisynthetic lipopeptide compounds targeted to the fungal cell wall, particularly the biosynthesis of 1,3-β-D-glucan. Cilofungin (N-p-octyloxybenzoylechinocandin B nucleus), the first echinocandin developed for clinical trials, has excellent in vitro an in vivo activity against disseminated candidiasis (Perfect et al., Antimicrob Agents Chemother, 33:1811-1812 (1989)); however, clinical development of cilofungin was discontinued because of toxicity (Walsh et al., Clin Infect Dis, 14 (Suppl. 1):139-147 (1992)). An improved echinocandin, Eraxis (anidulafungin: echinocandin B nucleus with a terphenyl head group and a C5 tail), was most recently approved by the FDA against life-threatening bloodstream *Candida* infections. Eraxis administered by injection is indicated for candidemia, peritonitis (infection of the abdominal cavity and intra-abdominal abscesses), and esophageal candidiasis (relapse rates post-therapy were higher for patients on Eraxis). Eraxis has not been studied in endocarditis, osteomyclitis, and meningitis due to *Candida*, and has not been studied in sufficient numbers of neutropenic patients (low white blood cell counts) to determine efficacy (Benjamin et al., Antimicrob Agents Chemother, 50(2):632-663 (2006)).

Leading Antifungals:

Amphotericin B. The only fungicidal agent available and remains the 'gold standard' for the treatment of most systemic mycoses today (Khoo et al., J Antimicrob Chemother, 33:203-213 (1994)). Amphotericin B is highly hydrophobic and commonly administrated as desoxycholate amphotericin (DAMB), a detergent micelle complex. Amphotericin B is usually administered by intravenous infusion; however, its use is limited by its substantial infusion-related and end organ toxicity (Gallis et al., Rev Infect Dis, 12:308-328 (1990)). Amphotericin B is insoluble in water, which accounts for its toxicity and poor bioavailability. Thus, new lipid-based formulations have been developed (Graybill, Ann Inter Med, 1245:921-923 (1996)): Abelcet (ABLC, amphotericin B: lipid Complex); Amphocil (ABCD: amphotericin B Colloid Dispersion); and, Ambisome (Liposomal amphotericin B). Each has been shown to be substantially less nephrotoxic than amphotericin B deoxycholate (Tollemar et al., Transplantation, 59:45-50 (1995)). Despite these new lipid formulations, amphotericin B combined with the detergent deoxycholate, still forms the first line therapy for empirical treatment of opportunistic fungal infections with greater in vivo activity and significantly less expensive than liposomal amphotericin B (Pahls et al., J Infect Dis, 169:1057-1061 (1994)).

Azole antifungals: Itraconazole (Sporanox) is the only marketed azole effective against pulmonary or extrapulmonary aspergillosis, particularly for patients refractory or intolerant to amphotericin B (Herbrecht et al., N Engl J Med, 347:408-415 (2002)). Itraconazole is the drug of choice against non-life threatening histoplasmosis, blastomycosis, paraccocidiodomycosis and meningeal coccidioidomycosis; and, the preferred agent for treatment of lymphocutaneous sporotrichosis. In candidemia, fluconazole (Diflucan) remains the drug of choice in neutropenic and non-neutropenic patients. However, amphotericin B is the agent of choice against *C. krusei* or fluconazole-resistant organism and in patients developing candidemia while on fluconazole therapy (Sheehan et al., Clin Microbial Rev, 12:40-79 (1999); Fidel et al., Clin Microbial Rev, 12(1):80-96 (1999)). In general, the azoles have a broad-spectrum antifungal activities and safer than amphotericin B, but are fungistatic, which lead to resistance and clinical failures.

Echinocandins: The echinocandins are a relatively new class of antifungals introduced some 15 years ago (Denning, J Antimicrob Chemother, 49:889-891 (2002)). The first FDA approved echinocandin product is caspofungin acetate (Cancidas; Merck); subsequent members of the class include micafungin (Mycamine; Fujisawa) and most recently (2/17/2006) anidulafungin (Eraxis; Pfizer). Although the echinocandins, in general, show comparable antifungal activities with the azoles, they have high molecular weights and are lipophilic (poorly soluble in water). Poor water-solubility may explain their poor oral absorption, which limits their utility to intravenous administration; thus, the need to develop water-soluble echinocandins (Hino et al., J Ind Microbiol Biotechnol, 27(3):157-162 (2001)).

Antifungal Therapy with AIDS

AIDS (acquired immune deficiency syndrome) disease is characterized by a gradual deterioration of immune function, particularly the CD4 positive (CD4+) T cells, due to HIV (human immune deficiency virus) infection. A healthy person usually has 800 to 1,200 CD4+ T cells per cubic millimeter (mm 3); once the CD4+ T cell count falls below 200/mm3, an individual becomes vulnerable to opportunistic infections and cancers. The FDA has approved several antifungal agents of different chemical classes (polyenes, pyrimidines, azoles, and echinocandins); however, treatment is often complicated by high toxicity, low tolerability, or narrow spectrum (Dismukes, Clin Infect Dis, 30:653-657 (2000)). Intensive therapy with amphotericin B is the treatment of choice in most situations.

In cryptococcal meningitis, the favored regimen is an "initial therapy" of amphotericin B plus flucytosine (Ancobon) for 2 weeks or until the patient's condition stabilizes, followed by a "consolidative therapy" of itraconazole or fluconazole for another 8-12 weeks (Saag et al., Clin Infect Dis, 30:710-718 (2000)). However, emergence of resistance to fluconazole after long treatments or prophylaxis is a growing concern (Berg et al., Clin Infect Dis, 26:186-187 (1998)), which now requires greater vigilance and more-widespread surveillance (Chandenier et al., J Clin Microbiol Infect Dis, 23:506-508 (2004)). In AIDS patients with extra-meningeal cryptococcosis (such as that of lungs, bone, soft tissue, disseminated form), itraconazole is quite effective, but is not indicated in cryptococcuria (Denning et al., Arch Intern Med, 149(10):2301-2308 (1989)).

In coccidioidal meningitis with AIDS, intrathecal amphotericin B has been the treatment of choice but is associated with compliance/administration problems and high incidence of adverse effects such as neurological toxicity (Stevens et al., Semin Respir Infect, 16:263-269 (2001)). Thus, fluconazole is the best alternative because of easy administration, better CSF penetration and predictable toxicity profile (Galgiani et al., Clin Infect Dis, 30(4):658-661 (2000)). In disseminated histoplasmosis with AIDS, initial intensive amphotericin B is the treatment of choice followed by maintenance therapy with itraconazole (Bartlett, Medical management of HIV infections, 113-137 (1999)); ketoconazole is not advisable for maintenance therapy because of a high failure rate.

Invasive aspergillosis is a serious complication in AIDS patients, and is associated with a poor prognosis (Marr et al., Infect Dis Clin North Am, 16:875-894 (2002)). Amphotericin B remains the drug of choice, though cure is rarely achieved. Itraconazole is indicated in patients intolerant to amphotericin B for maintenance therapy (Dupont, J Am Acad Dermatol, 23:607-614 (1990)), although only half are clinically stable for before succumbing to aspergillosis or another AIDS-related complications (Denning et al., Rev Infect Dis, 12:1147-1201 (1990)). Despite the introduction of newer antifungals (Steinbach et al., Clin Infect Dis, 37:157-187 (2003)), mortality rate associated with invasive aspergillosis remains nearly 100% in some patient groups (Denning, Clin Infect Dis, 23:608-615 (1996)).

Another common fungal infection in AIDS patients is mucosal and invasive candidiasis, especially the oropharyngeal (OPC) and esophageal form. Fluconazole in high doses (400-800 mg/day) remains the drug of choice for treatment (Newman et al., Clin Infect Dis, 19(4):684-686 (1994)); at low doses (150 mg per week), it is effective in preventing relapse. Unfortunately, the widespread use of fluconazole has spawned fluconazole-resistant strains of *C. albicans* and is a major problem in patients with advanced AIDS (Metzger et al., Mycoses, 40(Suppl. 1):56-63 (1997)). Itraconazole oral suspension have shown good results in AIDS patients with OPC who were clinically resistant to fluconazole (Saag et al., AIDS Res Hum Retroviruses, 15(16):1413-1417 (1999)), and esophageal candidiasis responds to 100 mg/day for at least 3 weeks, including 2 weeks after resolution of symptoms (Wilcox et al., J Infect Dis, 176:227-232 (1997)).

Antifungals and Drug Interaction:

Xenobiotics. Foreign chemicals or drugs are xenobiotics, which are subjected to a detoxification process by the cytochrome P450 (CYP) enzymes: converting lipophilic drugs into water-soluble forms for urine excretion. A drug that inhibits a specific CYP isozyme may decrease the metabolism of the drug and increase serum concentrations of drugs that are substrates for that isoenzyme. Conversely, a drug that induces a specific CYP isozyme may increase the metabolism of the drug and decrease serum concentrations of drugs that are substrates for that isozyme. Interference of drug metabolism by CYP induction, suppression, or inhibition accounts for some of the most common and potentially severe drug interactions encountered in the clinic (Zhou et al., Clin Pharmacokinet, 44(3):279-304 (2005)).

Because of the lipophilic nature of current antifungal drugs, drug interactions can arise with virtually any antifungal therapy, occurring in the gastrointestinal tract, liver and kidneys. Many drug interactions are a result of inhibition or induction of CYP, which changes the absorption or elimination of the interacting drug as well as the antifungal agent (Gubbins et al., Drug Interactions in Infectious Diseases (2001)). In the GI tract, changes in pH, complexation with ions, or interference with transport and enzymatic processes in the intestinal lumen can interfere with drug absorbance. Induction or inhibition of metabolism in the liver can inhibit or accelerate, respectively, drug clearance. In the kidney, decreases in glomerular filtration, active tubular secretion or other mechanisms can slow renal elimination resulting in excessive drug exposure.

The principal site for drug metabolism is the liver where lipophilic compounds are transformed into ionized metabolites for renal elimination (Kashuba et al., Drug Interactions in Infectious Diseases (2001)). The kidneys, usually known for excretion of water, electrolytes, drugs and other chemicals, also are very active in drug biotransformation. The CYP enzyme system in the kidneys has been identified as being as active as that in the liver, when corrected for organ mass. Therefore, patients with severe renal insufficiency receiving chronic drug therapy may experience accumulation of metabolites of some agents as well as the parent compounds.

Amphotericin B has several formidable toxicities, which are divided into 2 broad categories: infusion toxicities (chemical phlebitis, hypoxia, chills, fever, and nausea) and nephrotoxicity (manifested by renal insufficiency, hypokalemia, hypomagnesemia, renal tubular acidosis, and anemia). Nephrotoxicity occurs in as many as 80% of patients on amphotericin B and is enhanced by concomitant use of other nephrotoxic agents such as aminoglycosides, cyclosporine, cisplatin and nitrogen mustard compounds (Gleckman, Infect Dis Clin North Am, 9(3):575-590 (1995)).

All of the azole-class antifungals currently licensed by the FDA are metabolized to some degree by the CYP P450 system. Antifungal imidazole derivatives are frequently used both systemically and topically (depending on the particular agent) in the treatment of systemic candidal infections and mycoses. These derivatives, including ketoconazole (Nizoral), miconazole, tioconazole (Vagistat-1), clotrimazole (Lotrimin, Mycelex), and sulconazole (Exelderm), are recognized as potent ligands of the heme iron atom of P450s (Katz, Br J Dermatol, 141(Supp156):26-32 (1999)). Ketoconazole and itraconazole are weak bases, virtually insoluble in water, and are ionized only at a low pH. Consequently, dissolution and absorption of these compounds is heavily dependent on acidic gastric conditions in the stomach (Lange et al., J Clin Pharmacol, 37:535-540 (1997)). Drugs that increase gastric pH (e.g., $H_2$ antagonists, proton pump inhibitors) slow the dissolution of the solid dosage forms and decrease drug available for absorption in the intestinal lumen. Because the azole drugs are metabolized by the hepatic cytochrome P-450 system, a variety of interactions can occur between these agents and other medications. The azole antifungals decrease the catabolism of numerous drugs resulting in increased serum concentrations of these medications and the potential for drug toxicity (e.g., histamine H1 receptor antagonists, warfarin, cyclosporin, tacrolimus, sirolimus, digoxin, felodipine, lovastatin, midazolam, triazolam, methylprednisolone, glibenclamide, rifabutin, ritonavir, saquinavir, nevirapine, nortriptyline, sulfonylureas, omeprazole, and cisapride). Conversely, serum concentrations of the triazoles are decreased by rifampin, isoniazid, phenytoin, fosphenytoin, and carbamazepine (Albengres et al., Drug Saf, 18(2):83-97 (1998)). Griseofulvin is a CYP inducer of coumarin-like drugs and estrogens (Kojo et al., Arch Toxicol, 72:336-346 (1998)).

Antifungals and highly active antiretroviral therapy (HAART). One of the most challenging issues facing providers treating patients with human immunodeficiency virus (HIV) infection is the complex problem of drug interactions associated with highly active antiretroviral therapy (HAART). Given the effects of the protease inhibitor (PI) and non-nucleoside reverse transcriptase (NNRTI) class on the CYP450 system, metabolism drug interactions are most common and problematic when prescribing HAART. Approximately 50% of all drugs are substrates of CYP3A4, including HIV protease inhibitors (PIs) and non-nucleoside reverse transcriptase inhibitors (NNRTIs). Antifungal drugs (ketoconazole, itraconazole, fluconazole) and macrolides (erythromycin, clarithromycin) are CYP3A4 inhibitors and increase plasma concentrations of NNRTIs and P is (Piscitelli et al., N Engl J Med, 344:984-996 (2001)). The azole antifungal ketoconazole is a potent CYP3A4 inhibitor and increases the level of drug exposure to saquinavir and amprenavir by 190% and 31%, respectively. Conversely, ritonavir and lopinavir/ritonavir have demonstrated a three-fold increase in ketoconazole levels when used concurrently. Therefore doses >200 mg/day of ketoconazole are not recommended when using these medications concurrently. In general, ketoconazole should be avoided with concurrent HAART. The newest azole antifungal, voriconazole (Vfend), has significant activity against aspergillosis and *Candida albicans,* but should be closely monitored for toxicity, such as elevated transaminases and visual toxicity.

Thus, besides the classic non-polyenic antibiotics (Gottlieb et al., Ann Rev Phytopathol, 8:371-380 (1970): cycloheximide, griseufulvin, antimycin, the polyoxins, the oligomycins, and variotin), and the echinocandins, new antifungal antibiotics continue to be discovered: diazaquinomycin (Maskey et al., Nat Prod Res, 19(2):137-142 (2005)), norresistomycin and resistoflavin (Kock et al., J Antibiot (Tokyo), 58(8):530-534 (2005)), fridamycin (Maskey et al., J Antibiot (Tokyo), 56(11):942-949 (2003)) transvalencin (Hoshino et al., J Antibiot (Tokyo), 57(12):803-807 (2004)), clavariopsins—cyclic depsipeptides (Kaida et al., J Antibiot (Tokyo), 54(1):17-21 (2001)). The echinocandins are synthetic modifications of naturally produced lipopeptides; these natural lipopeptides are produced by fungi (Denning, J Antimicrob Chemother, 49:889-891 (2002)), which include aculeacin A (*Aspergillus aculeatus*), echinocandin B (*Aspergillus rugulovalvus*), pneumocandin B (*Zalerion arboricola*), enfumafungin (*Hormonema*-like fungus) and the papulacandins (*Papularia sphaerosperma*). On the other hand, fengycin is a lipopeptide produced by a bacterium, *Bacillus subtilis* (Vanittanakom et al., J Antibiot (Tokyo), 39(7):888-901 (1986)).

Because of the shortcomings of existing antifungal treatments, there is a need in the art for improved antifungal therapies having greater efficacy, bioavailability, and/or reduced side effects.

SUMMARY

The present disclosure addresses long-felt needs in the field of medicine by providing novel compositions and methods for treating fungal and parasitic infections. While polyene macrolides as a class are limited by their insolubility in water, the present disclosure provides novel polyene macrolides, which are water-soluble broad-spectrum agents exhibiting antibiotic, antifungal, and antiparasitic activities with improved bioavailability and low toxicity in animals.

The present disclosure provides compositions and methods for the treatment and inhibition of fungal and parasitic infections. The present disclosure relates to novel polyene macrolides, biosynthetic methods for producing these polyene macrolides, and methods of treating fungal and parasitic infections using the novel polyene macrolides.

In various aspects, the present disclosure provides for compounds of Structure (I):

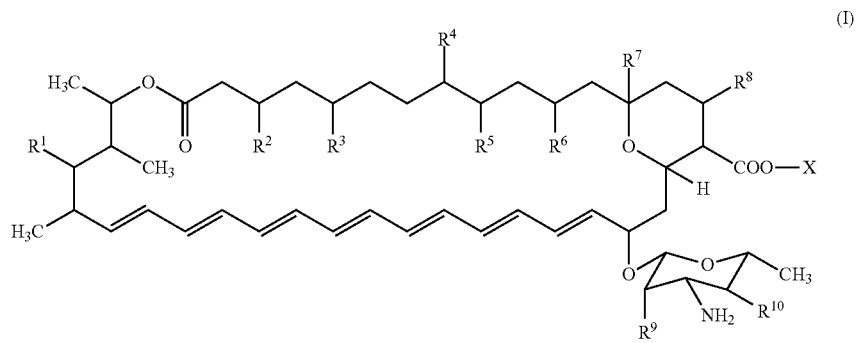

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation, wherein the cation is an organic cation or is a cation of aluminum, calcium, lithium, magnesium, or zinc.

In certain aspects, the present disclosure provides for compounds of Structure (II)

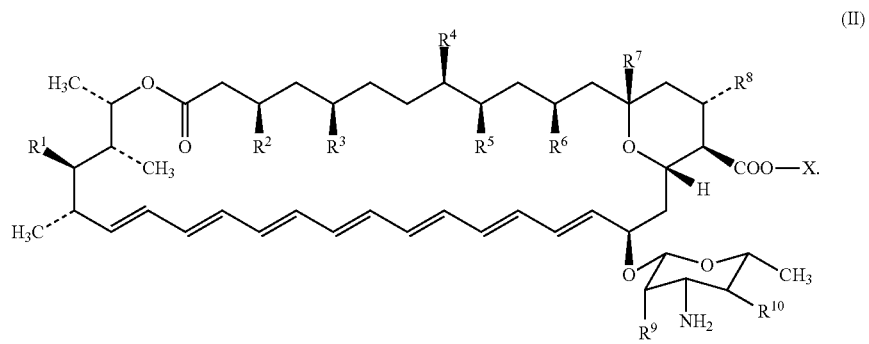

(II)

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation, wherein the cation is an organic cation or is a cation of aluminum, calcium, lithium, magnesium, or zinc.

In certain aspects, the present disclosure provides for compounds of one of the following Structures (III) or (IV):

or a pharmaceutically acceptable isomer thereof, wherein

X is a pharmaceutically acceptable cation, wherein the cation is an organic cation or is a cation of aluminum, calcium, lithium, magnesium, or zinc.

In various aspects, the compounds of the present disclosure have antifungal activity. In further aspects, the compounds of the present disclosure have antibacterial activity. In yet further aspects, the compounds of the present disclosure have antiparasitic activity.

In certain aspects, the present disclosure provides methods for treating or inhibiting a fungal infection in a subject, the

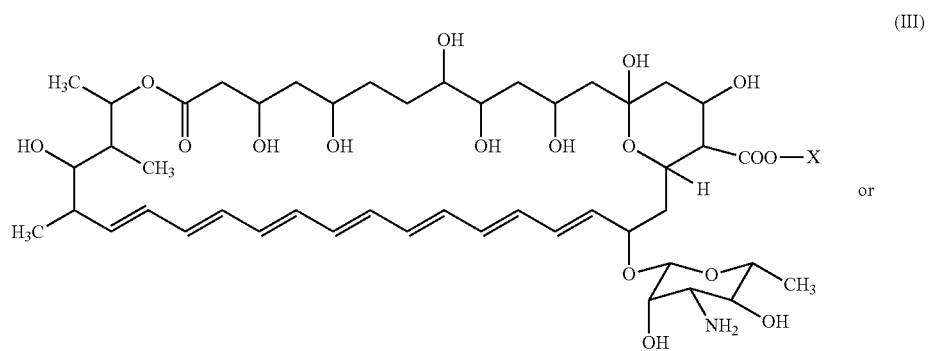

(III)

or

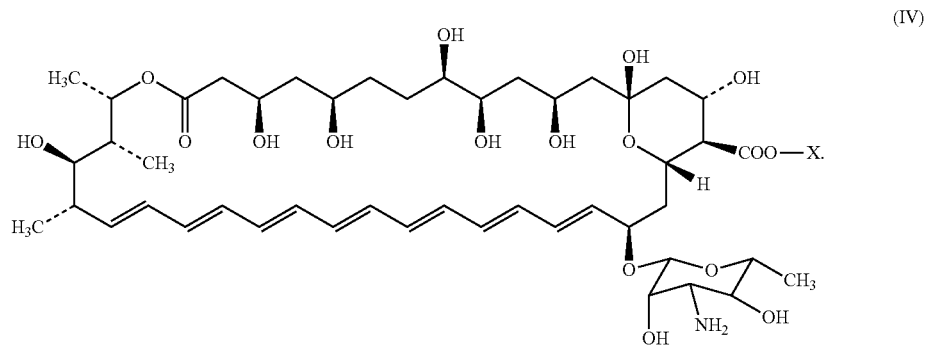

(IV)

method comprising administering to the subject an effective amount of a compound of Structure (I):

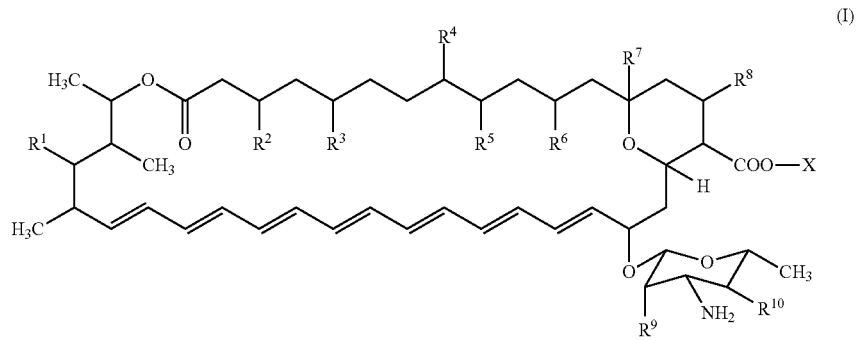

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation, wherein the cation is an organic cation or is a cation of aluminum, calcium, lithium, magnesium, or zinc.

In certain aspects, the present disclosure provides methods for treating or inhibiting a parasitic infection in a subject, the method comprising administering to the subject an effective amount of a compound of Structure (I):

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation, wherein the cation is an organic cation or is a cation of aluminum, calcium, lithium, magnesium, or zinc.

(I)

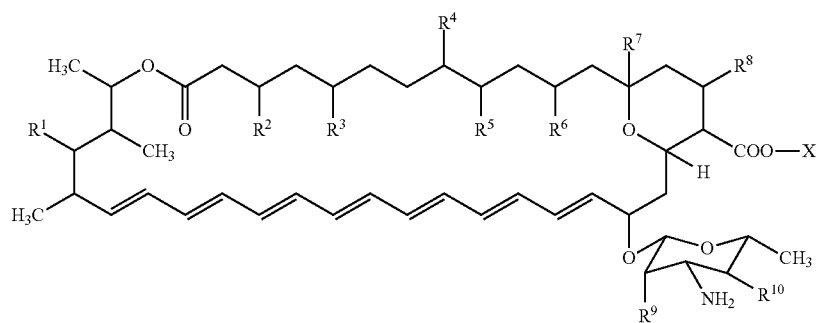

In some aspects, the present disclosure provides for methods of producing a compound of Structure (I):

(I)

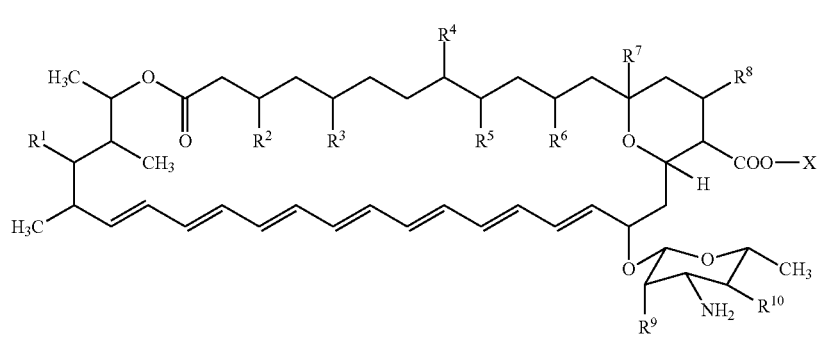

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation, wherein the cation is an organic cation or is a cation of aluminum, calcium, lithium, magnesium, or zinc the method comprising the steps of:

combining microorganisms with a seed media having a suitable pH and temperature;

combining the microorganisms with a complex media;

fermenting the microorganisms in the complex media;

producing a fermentation product;

isolating the fermentation product by extracting the fermentation product into an organic solvent; and forming the salt of the fermentation product by combining the fermentation product with a pharmaceutically acceptable cation, wherein the cation is an organic cation or is a cation of aluminum, calcium, lithium, magnesium, or zinc, thereby forming the compound of Structure (I).

In certain aspects, the present disclosure provides for pharmaceutical compositions comprising the compounds of the present disclosure together with one or more pharmaceutically acceptable vehicles. In certain aspects, the pharmaceutically acceptable vehicle is an excipient. In further aspects, the pharmaceutically acceptable excipient is a permeation enhancer excipient. In some aspects, the composition is formulated in an enterically coated time controlled release pharmaceutical dosage form.

BRIEF DESCRIPTION OF THE DRAWINGS

FIG. 6 shows the accurate mass analysis of corifungin.

DETAILED DESCRIPTION

Figure 1:
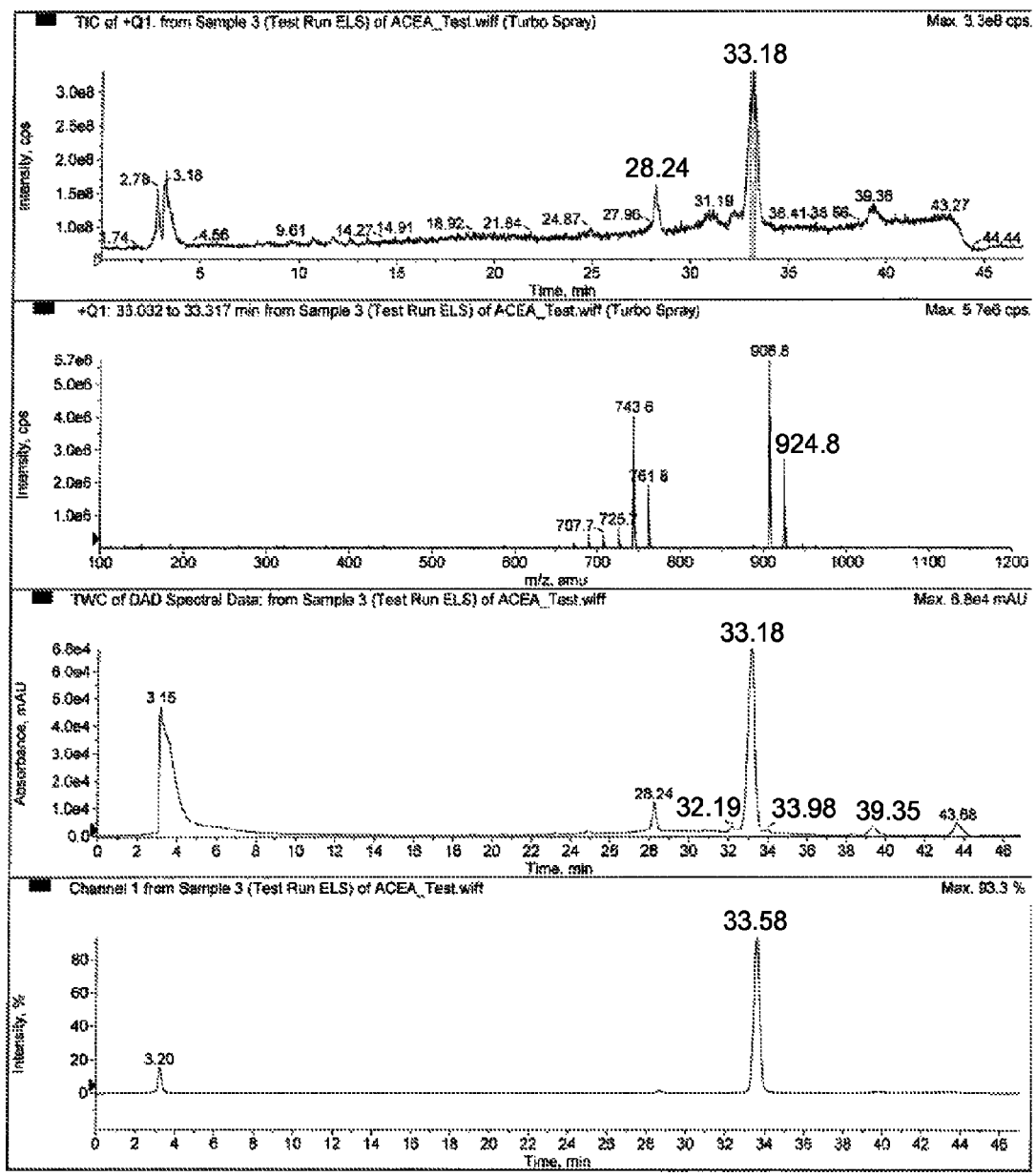
FIG. 1 shows the LC-MS analysis of corifungin, including the TIC mass spectrum of the major peak, UV chromatogram, and ELS chromatogram.

Briefly stated, the present disclosure provides methods and compositions for the treating fungal and parasitic infections.

The present disclosure further relates to novel methods for producing the compounds of the present disclosure, and methods of treating fungal or parasitic infections using those compounds.

The descriptions of various embodiments of the present disclosure are presented for purposes of illustration, and are not intended to be exhaustive or to limit the invention to the forms disclosed. Persons skilled in the relevant art can appreciate that many modifications and variations are possible in light of the embodiment teachings. Accordingly, the disclosure is intended to be illustrative, but not limiting, of the scope of invention.

Any terms not directly defined herein shall be understood to have the meanings commonly associated with them as understood within the art of the present disclosure. Certain terms are discussed herein to provide additional guidance to the practitioner in describing the compositions, devices, methods and the like of embodiments of the present disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the present disclosure herein.

Screening for Antifungal Agents

Antifungal agents are produced either synthetically or as natural products from microorganisms. Screening of antifungals from natural sources, particularly actinomycetes, predominantly yield polyene macrolides. Up to 88% of actinomycetes are capable of producing polyenes (Ball et al., J Gen Microbiol, 17:96-101 (1957); Iznaga et al., Phytother Res, 18(6):494-496 (2004)), and there are at least 185 known polyenes. While polyenes are not water-soluble because of their hydrophobic double-bond macrolide structure, hydroheptin was found to be water-soluble (Tunac et al., J Antibiot (Tokyo), 32(12):1230-1238 (1979)). To date, polyene macrolide antibiotics are still the most effective antifungal agents due to their potent fungicidal activity, broad spectrum, and relatively low frequency of resistance among the fungal pathogens. However, polyene macrolides are particularly toxic, causing such serious side effects as renal failure, hypokalemia and thrombophlebitis, especially upon intravenous administration (Zotchev, Curr Med Chem, 10(3):211-223 (2003)).

Because of the associated toxicity observed with polyenes, there is a continued interest in the screening for non-polyene antifungals. In order to increase the chance of discovery, unusual microorganisms or sources are being investigated including, clinical actinomycete isolates (Lemriss et al., Can J Microbiol, 49:669-674 (2003)), microorganisms from dessert soil (Hacene et al., Microbios, 79(319):81-85 (1994)), marine microorganisms (Bernan et al., Curr Med Chem—Anti-Infective Agents, 3(3):181-195 (2004)), marine invertebrates (Antonio et al., J Nat Prod, 56(1):54-61 (1993)) and, extremophiles (Horikoshi, Microbiol Mol Biol Rev, 63:735-750 (1999)) or piezophiles—high pressure (Abe et al., Trends Biotechnol, 19:102-108 (2001)). Another strategy involves change of culture media (Tunac, Anticancer Drug Discovery and Development: Natural Products and New Molecular Models (1991)), or physical environment such as high-aeration (Tunac, J Ferment Bioeng, 68:157-159 (1989)).

Compounds

The present disclosure provides compositions and methods for treating or inhibiting diseases caused by fungal or parasitic infections. The compounds and compositions of the present disclosure can be delivered alone or in combination with additional agents and are used for the treatment or inhibition of superficial or systemic fungal or parasitic infections.

In various aspects, the present disclosure provides for compounds of Structure (I):

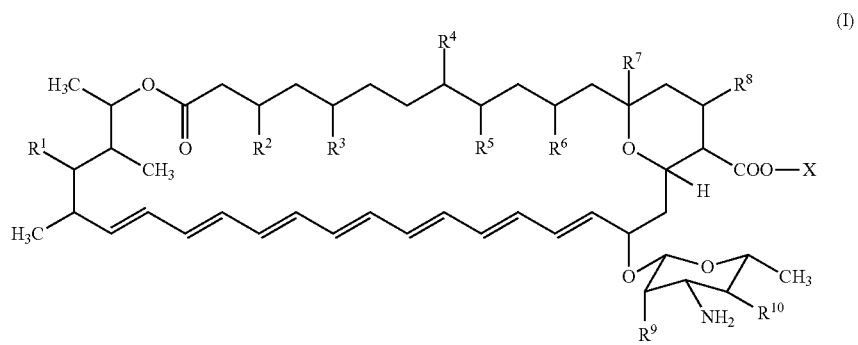

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation.

In certain aspects of Structure (I), $R^1$, $R^2$, $R^3$, $R^4$, $R^5$, $R^6$, $R^7$, $R^8$, $R^9$, and $R^{10}$ are each independently —OH or hydrogen.

In certain aspects of Structure (I), $R^1$, $R^2$, $R^3$, $R^4$, $R^5$, $R^6$, $R^7$, $R^8$, $R^9$, and $R^{10}$ are each independently —OH.

In certain aspects of Structure (I), X is an inorganic cation.

In certain aspects of Structure (I), X is a cation of sodium, potassium, aluminum, calcium, lithium, magnesium, or zinc.

In certain aspects of Structure (I), X is a cation of sodium.

In certain aspects of Structure (I), X is a cation of potassium.

In certain aspects of Structure (I), X is a cation of calcium.

In certain aspects of Structure (I), X is a cation of aluminum, calcium, lithium, magnesium, or zinc.

In certain aspects of Structure (I), X is an organic cation.

In certain aspects of Structure (I), X is a cation of an amine, $C_1$-$C_{10}$ alkyl, halo-$C_1$-$C_6$ alkyl, $C_2$-$C_6$ alkenyl, $C_2$-$C_6$ alkynyl, $C_1$-$C_6$ sulfinylalkyl, $C_1$-$C_6$ sulfonylalkyl, $C_1$-$C_6$ thioalkyl, $C_1$-$C_6$ aminoalkyl, $C_1$-$C_6$ hydroxyalkyl, arylalkyl, cycloalkyl, heterocycle, or heteroaryl.

In certain aspects of Structure (I), X is a cation of an amine and the amine is tetramethylammonium, ammonia, ethylenediamine, N-methylglucamine, lysine, arginine, orthinine, choline, N,N' dibenzylethylenediamine, chloroprocaine, diethanolamine, procaine, N-benzylphenethylamine, 1-p-chlorobenzyl-2-pyrrolidine-1'-methylbenzimidazole, diethylamine, piperazine, morpholine, 2, 4, 4-trimethyl-2-pentamine, or tris(hydroxymethyl)amino methane.

In certain aspects of Structure (I), the compound has antifungal activity.

In certain aspects of Structure (I), the compound has antibacterial activity.

In certain aspects of Structure (I), the compound has antiparasitic activity.

In certain aspects of Structure (I), the compound has anti-*Leishmania* activity or anti-*Naegleria* activity.

In certain aspects, the present disclosure provides for compounds of Structure (II)

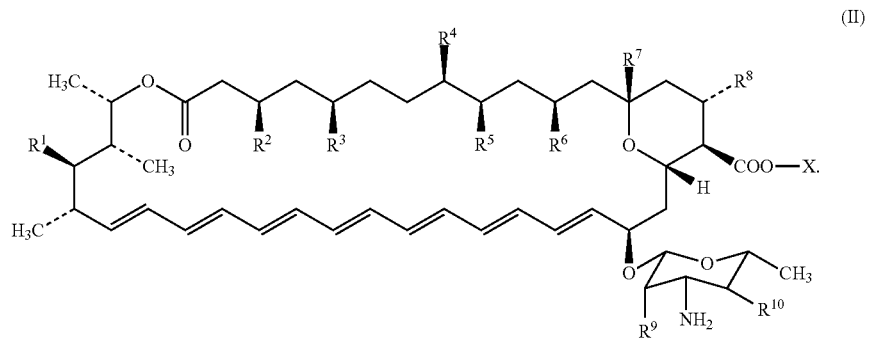

(II)

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_i$-$C_6$ alkoxy, optionally substituted $C_1$-$C_6$ alkanoyl, amide, carboxy, or ester; and X is a pharmaceutically acceptable cation.

In certain aspects of Structure (II), $R^1$, $R^2$, $R^3$, $R^4$, $R^5$, $R^6$, $R^7$, $R^8$, $R^9$, and $R^{10}$ are each independently —OH or hydrogen.

In certain aspects of Structure (II), $R^1$, $R^2$, $R^3$, $R^4$, $R^5$, $R^6$, $R^7$, $R^8$, $R^9$, and $R^{10}$ are each independently —OH.

In certain aspects of Structure (II), X is an inorganic cation.

In certain aspects of Structure (II), X is a cation of sodium, potassium, aluminum, calcium, lithium, magnesium, or zinc.

In certain aspects of Structure (II), X is a cation of sodium.

In certain aspects of Structure (II), X is a cation of potassium.

In certain aspects of Structure (II), X is a cation of calcium.

In certain aspects of Structure (II), X is a cation of aluminum, calcium, lithium, magnesium, or zinc.

In certain aspects of Structure (II), X is an organic cation.

In certain aspects of Structure (II), X is a cation of an amine, $C_1$-$C_{10}$ alkyl, halo-$C_1$-$C_6$ alkyl, $C_2$-$C_6$ alkenyl, $C_2$-$C_6$ alkynyl, $C_1$-$C_6$ sulfinylalkyl, $C_1$-$C_6$ sulfonylalkyl, $C_1$-$C_6$ thioalkyl, $C_1$-$C_6$ aminoalkyl, $C_1$-$C_6$ hydroxyalkyl, arylalkyl, cycloalkyl, heterocycle, or heteroaryl.

In certain aspects of Structure (II), X is a cation of an amine and the amine is tetramethylammonium, ammonia, ethylenediamine, N-methylglucamine, lysine, arginine, orthinine, choline, N,N' dibenzylethylenediamine, chloroprocaine, diethanolamine, procaine, N-benzylphenethylamine, 1-p-chlorobenzyl-2-pyrrolidine-1'-methylbenzimidazole, diethylamine, piperazine, morpholine, 2, 4, 4-trimethyl-2-pentamine, or tris(hydroxymethyl)aminomethane.

In certain aspects of Structure (II), the compound has antifungal activity.

In certain aspects of Structure (II), the compound has antibacterial activity.

In certain aspects of Structure (II), the compound has antiparasitic activity.

In certain aspects of Structure (II), the compound has anti-*Leishmania* activity or anti-*Naegleria* activity.

In certain aspects, the present disclosure provides for compounds of one of the following Structures (III) or (IV):

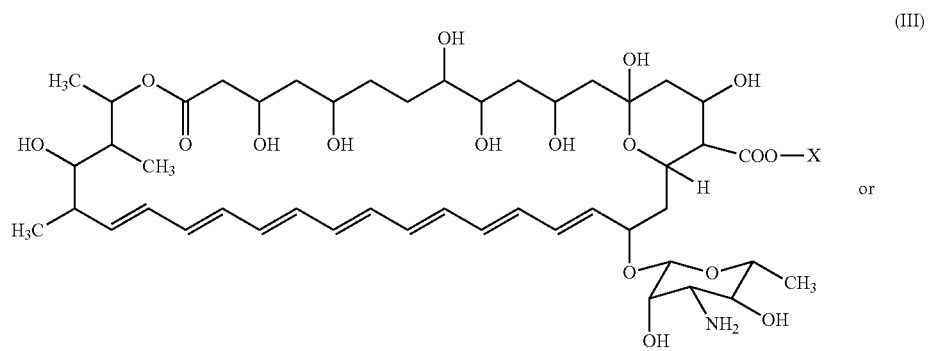

(III)

or

-continued (IV)

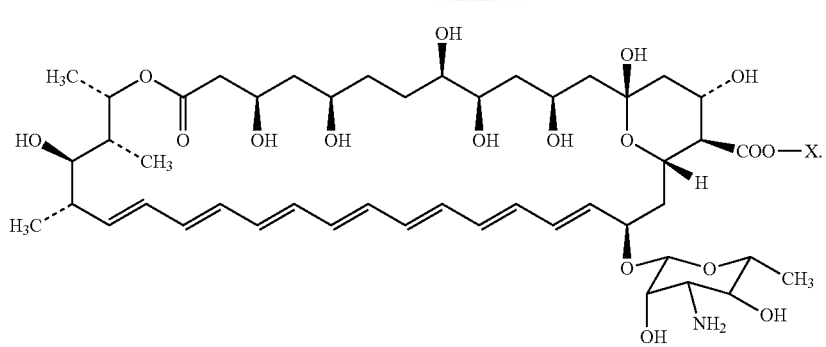

or a pharmaceutically acceptable isomer thereof, wherein
X is a pharmaceutically acceptable cation.

In certain aspects of Structure (III) or (IV), X is an inorganic cation.

In certain aspects of Structure (III) or (IV), X is a cation of sodium, potassium, aluminum, calcium, lithium, magnesium, or zinc.

In certain aspects of Structure (III) or (IV), X is a cation of sodium.

In certain aspects of Structure (III) or (IV), X is a cation of potassium.

In certain aspects of Structure (III) or (IV), X is a cation of calcium.

In certain aspects of Structure (III) or (IV), X is a cation of aluminum, calcium, lithium, magnesium, or zinc.

In certain aspects of Structure (III) or (IV), X is an organic cation.

In certain aspects of Structure (III) or (IV), X is a cation of an amine, $C_1$-$C_{10}$ alkyl, halo-$C_1$-$C_6$ alkyl, $C_2$-$C_6$ alkenyl, $C_2$-$C_6$ alkynyl, $C_1$-$C_6$ sulfinylalkyl, $C_1$-$C_6$ sulfonylalkyl, $C_1$-$C_6$ thioalkyl, $C_1$-$C_6$ aminoalkyl, $C_1$-$C_6$ hydroxyalkyl, arylalkyl, cycloalkyl, heterocycle, or heteroaryl.

In certain aspects of Structure (III) or (IV), X is a cation of an amine and the amine is tetramethylammonium, ammonia, ethylenediamine, N-methylglucamine, lysine, arginine, orthinine, choline, N,N' dibenzylethylenediamine, chloroprocaine, diethanolamine, procaine, N-benzylphenethylamine, 1-p-chlorobenzyl-2-pyrrolidine-1'-methylbenzimidazole, diethylamine, piperazine, morpholine, 2,4,4-trimethyl-2-pentamine, or tris(hydroxymethyl)aminomethane.

In certain aspects of Structure (III) or (IV), the compound has antifungal activity.

In certain aspects of Structure (III) or (IV), the compound has antibacterial activity.

In certain aspects of Structure (III) or (IV), the compound has antiparasitic activity.

In certain aspects of Structure (III) or (IV), the compound has anti-*Leishmania* activity or anti-*Naegleria* activity.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. The compositions and formulations described herein can be practiced employing the pharmaceutically acceptable excipients and salts available in *Remington's Pharmaceutical Sciences*, $18^{th}$ Edition (Easton, Pa.: Mack Publishing Company, 1990).

"Compounds of the invention" refers to compounds encompassed by structural Formulae (I), (II), (III), (IV), and (V) disclosed herein. The compounds of the invention can be identified either by their chemical structure and/or chemical name. When the chemical structure and chemical name conflict, the chemical structures is determinative of the identity of the compound. The compounds of the invention may contain one or more chiral centers and/or double bonds and therefore, may exist as stereoisomers, such as double-bond isomers (i.e., geometric isomers), enantiomers or diastereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass of conventionally found in nature. Examples of isotopes that may be incorporated into the compounds of the invention include, but are not limited to $^2H$, $^3H$, $^{13}C$, $^{15}N$, $^{18}O$, $^{17}O$, $^{31}P$, $^{32}P$, $^{35}S$, $^{18}F$ and $^{36}Cl$. Further, it should be understood, when partial structures of the compounds of the invention are illustrated, that brackets of dashes indicate the point of attachment of the partial structure to the rest of the molecule.

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1$, $C_2$, $C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1$, $C_2$, $C_3$, $C_{1-2}$, $C_{1-3}$, and $C_{2-3}$ alkyl.

"Alkylamino" refers to an amino group substituted by an alkyl group.

"Alkanoyl" refers to a R—C(=O)— group, where R is an alkyl group as defined below.

"Alkoxy" refers to an O-atom substituted by an alkyl group as defined herein, for example, methoxy [—$OCH_3$, a $C_1$alkoxy]. The term "$C_{1-6}$ alkoxy" encompasses $C_1$ alkoxy, $C_2$ alkoxy, $C_3$ alkoxy, $C_4$ alkoxy, $C_5$ alkoxy, $C_6$ alkoxy, and any sub-range thereof.

"Alkyl," "alkenyl," and "alkynyl," refer to straight and branched chain aliphatic groups having from 1 to 30 carbon atoms, or preferably from 1 to 15 carbon atoms, or more preferably from 1 to 6 carbon atoms, each optionally substituted with one, two or three substituents depending on valency. Examples of such groups include, without limitation, methyl, ethyl, propyl, isopropyl, butyl, tent-butyl, isobutyl, pentyl, hexyl, vinyl, allyl, isobutenyl, ethynyl, and propynyl. The term "$C_{1-6}$ alkyl" encompasses $C_1$ alkyl, $C_2$ alkyl, $C_3$ alkyl, $C_4$ alkyl, $C_5$ alkyl, $C_6$ alkyl, and any sub-range thereof.

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Amino" refers to the group —$NH_2$.

"Aminoalkyl" refers to an alkyl group substituted with an amino group.

"Amine" refers to a —N(R')R" group, wherein R' and R" are independently selected from the group consisting of alkyl, aryl, and alkylaryl.

"Aryl" refers to aromatic groups which have at least one ring having a conjugated pi electron system and includes carbocyclic aryl, and biaryl groups, all of which can be optionally substituted. Phenyl and naphthyl groups are preferred carbocyclic aryl groups.

"Aralkyl" or "arylalkyl" refer to alkyl-substituted aryl groups. Examples of aralkyl groups include butylphenyl, propylphenyl, ethylphenyl, methylphenyl, 3,5-dimethylphenyl, tert-butylphenyl.

"Cycloalkyl" refers to a ring, which can be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which can be either an aryl ring or a cycloalkyl ring, both as defined above.

"Corifungin" refers to the sodium salt of amphotericin B as shown below in Structure (V):

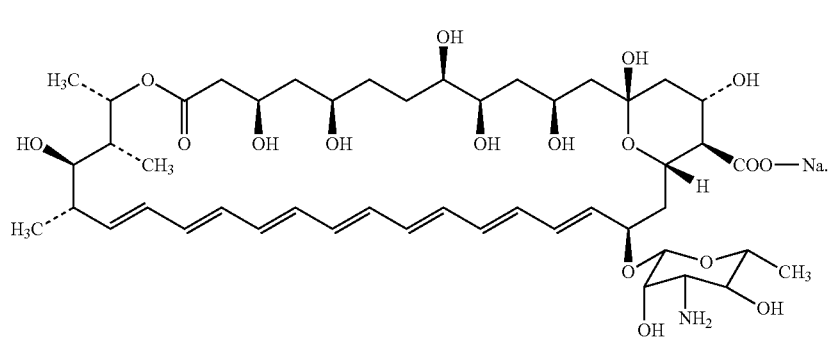

(V)

"Heterocycle" refers to a 5- to 7-membered cycloalkyl ring system containing 1, 2 or 3 heteroatoms, which can be the same or different, selected from N, O or S, and optionally containing one double bond.

"Halogen" refers to a chloro, bromo, fluoro or iodo atom radical. The term "halogen" also contemplates terms "halo" or "halide".

"Halo-alkyl" refers to an alkyl group substituted with a halogen.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present disclosure.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing a hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Isomer" refers to compounds of the present invention that possess asymmetric carbon atoms (optical centers) or double bonds, the racemates, diastereomers, enantiomers, geometric isomers, structural isomers and individual isomers are all intended to be encompassed within the scope of the present invention.

"Sulfinyl," whether used alone or linked to other terms such as alkylsulfinyl, denotes respectively divalent radicals —S(O)—.

"Alkylsulfinyl" or "sulfinylalkyl" are as used herein alone or as part of another group, to refer to an alkyl group, as defined herein, appended to a parent molecular moiety through a sulfinyl group, as defined herein.

"Sulfonyl" as used herein alone or as part of another group, refers to an $SO_2$ group. The $SO_2$ moiety is optionally substituted.

"Alkylsulfonyl" or "aminosulfonyl" refer to an alkyl or amino group, as defined herein, appended to a parent molecular moiety through a sulfonyl group, as defined herein.

"Thioalkyl" or "alkylthio" refer to a sulfur atom substituted by an alkyl group, for example, methylthio, butylthio, and the like.

A "substituted" moiety is a moiety in which one or more hydrogen atoms have been independently replaced with another chemical substituent. As a non limiting example, substituted phenyl groups include 2-fluorophenyl, 3,4-dichlorophenyl, 3-chloro-4-fluorophenyl, and 2-fluoro-3-propylphenyl. In some instances, a methylene group (—$CH_2$—) is substituted with oxygen to form a carbonyl group (—CO).

An "optionally substituted" group can be substituted with from one to four, or preferably from one to three, or more preferably one or two non-hydrogen substituents. Examples of suitable substituents include, without limitation, alkyl, alkenyl, alkynyl, cycloalkyl, heterocycloalkyl, aryl, heteroaryl, aroyl, halo, hydroxy, oxo, nitro, alkoxy, amino, imino, azido, mercapto, acyl, carbamoyl, carboxy, carboxamido, amidino, guanidino, sulfonyl, sulfinyl, sulfonamido, formyl, cyano, and ureido groups.

Compounds of the present disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present disclosure contemplates various stereoisomers and mixtures thereof and are specifically included within the scope of the present disclosure. Stereoisomers include enantiomers, diastereomers, and mixtures of enantiomers or diastereomers. Individual stereoisomers of compounds of the present disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Also, moieties disclosed herein which exist in multiple tautomeric forms include all such forms encompassed by a given tautomeric structure.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

"Acid addition salts" according to the present disclosure, are formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"Base addition salts" according to the present disclosure are formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature can cause a single crystal form to dominate.

Synthesis of Compounds

Also described herein are methods of synthesizing the compounds of the present disclosure. In some aspects, the present disclosure provides for methods of producing a compound of Structure (I):

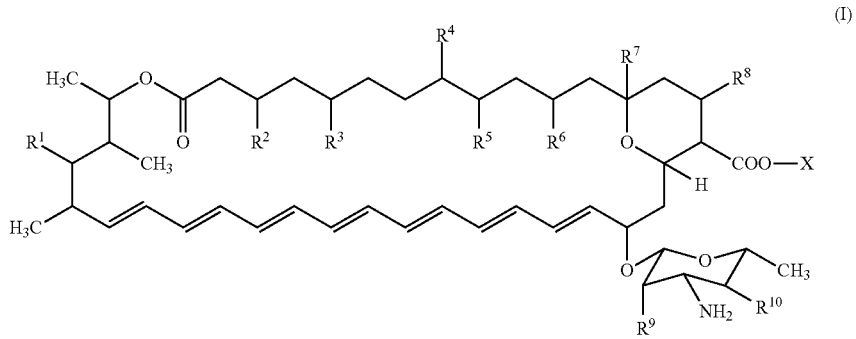

(I)

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation, wherein the cation is an organic cation or is a cation of aluminum, calcium, lithium, magnesium, or zinc; the method comprising the steps of:

combining microorganisms with a seed media having a suitable pH and temperature;

combining the microorganisms with a complex media;

fermenting the microorganisms in the complex media;

forming a fermentation product;

isolating the fermentation product by extracting the fermentation product into an organic solvent; and forming the salt of the fermentation product by combining the fermentation product with a pharmaceutically acceptable cation, wherein the cation is an organic cation or is a cation of aluminum, calcium, lithium, magnesium, or zinc, thereby forming the compound of Structure (I).

The compounds of the present disclosure can be synthesized using any suitable microorganism. Suitable microorganisms according to the present disclosure include, for example, Streptomyces nodosus and mutants thereof. In various aspects of the present disclosure, the Streptomyces nodosus NRRL B-2371 strain can be used to synthesize the compounds of the present disclosure. The pH and temperature conditions can be adjusted in order to optimize the production of the present compounds. Typically, cell culture agitation and aeration improve compound production.

According to one aspect of the present methods, the microorganisms are initially innoculated into a liquid seed media comprising 1.0% dextrose, 0.3% soya fluff, 0.3% brewer's yeast (Tunac, J Ferment Bioeng, 68:15 - 159 (1989)), followed by incubation and shaking overnight. The compounds can then be produced by fermentation in a complex medium comprising 4.0% dextrose, 2.0% soya fluff, 0.5% brewer's yeast, and 0.5% calcium carbonate using aeration and agitation. Modification of these reaction conditions enables the production of related compounds.

In various aspects, the pH of the seed media is between about pH 3 and about pH 10. In further aspects, the pH of the seed media is between about pH 5 and pH 7. In certain aspects, the pH of the seed media is about pH 6. In various aspects, the reaction temperature is between 18° C. and 33° C. In further aspects, the reaction temperature is between 21° C. and 27° C. In certain aspects, the reaction temperature is about 24° C. In various aspects, the compounds of the present disclosure can be extracted using an organic solvent, wherein the organic solvent is selected from the group consisting of methanol, ethanol, isopropanol, butanol, and ethyl acetate.

Compounds of the present disclosure can be produced on a larger scale through the use of a suitable bioreactor (e.g., Tunac, U.S. Pat. No. 5,075,234 (1991)), including 25-, 100-, 500-gallon size Airmentors.

In shake-flasks, aeration is achieved by agitating the flasks to bring about intimate mixing of the inoculated medium with air. In stationary tank fermentors, agitation is provided by impellers, which can take the form of disc turbines, vaned discs, or open turbine or marine propellers. Aeration is accomplished by sparging air or oxygen into the agitated mixture.

According to certain aspects of the present disclosure, the fermentation products can be isolated and purified from the source microorganisms. Typically, the mycelium is separated from the whole broth by filtration or centrifugation after a suitable period of growth. The mycelium can then be extracted using a suitable solvent. Suitable solvents include methanol, ethanol, isopropanol, butanol, ethyl acetate, and similar solvents. The solvent extract is then evaporated in vacuo to dryness and washed with a second solvent, for example acetone or the like.

The fermentation product can then be dried in a desiccator and further processed to yield various salts or solvates. The pharmaceutically acceptable salts of the present invention can be synthesized from the fermentation product, which contains a basic or an acidic moiety, by conventional chemical methods. Generally the salts are prepared by contacting the free base or acid with stoichiometric amounts or with an excess of the desired salt-forming inorganic or organic acid or base in a suitable solvent or dispersant or from another salt by cation or anion exchange. Suitable solvents are, for example, ethyl acetate, ether, alcohols, acetone, THF, dioxane or mixtures of these solvents.

In various aspects, a salt is formed from an inorganic cation. In certain aspects, a sodium, potassium, aluminum, calcium, lithium, magnesium, or zinc salt is formed. For example, in certain aspects, corifungin can be produced by treating the above fermentation product with NaOH.

In various aspects, the salt is formed from an organic cation. In certain aspects a salt of an amine, $C_1$-$C_{10}$ alkyl, halo-$C_1$-$C_6$ alkyl, $C_2$-$C_6$ alkenyl, $C_2$-$C_6$ alkynyl, $C_1$-$C_6$ sulfinylalkyl, $C_1$-$C_6$ sulfonylalkyl, $C_1$-$C_6$ thioalkyl, $C_1$-$C_6$ aminoalkyl, $C_1$-$C_6$ hydroxyalkyl, arylalkyl, cycloalkyl, heterocycle, or heteroaryl is formed. In further aspects, a salt of an amine is formed, wherein the amine is tetramethylammonium, ammonia, ethylenediamine, N-methylglucamine, lysine, arginine, orthinine, choline, N,N' dibenzylethylenediamine, chloroprocaine, diethanolamine, procaine, N-benzylphenethylamine, 1-p-chlorobenzyl-2-pyrrolidine-1'-methylbenzimidazole, diethylamine, piperazine, morpholine, 2,4,4-trimethyl-2-pentamine, or tris(hydroxymethyl) aminomethane.

Pharmaceutical Formulations and Modes of Administration

In certain aspects, the present disclosure provides for a pharmaceutical composition comprising the compounds of the present disclosure together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, and the like.

The term "pharmaceutically acceptable vehicle" refers to a diluent, adjuvant, excipient or carrier with which a compound of the present disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an "effective amount" for therapeutic uses is the amount of the composition comprising one or more polyene macrolide compounds disclosed herein required to treat diseases caused by fungal infections to provide a clinically significant decrease in infections. An appropriate "effective" amount in any individual case can be determined by one of ordinary skill in the art using routine experimentation.

"Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, etc.

The present disclosure includes a pharmaceutical composition comprising a compound of the present disclosure including isomers, racemic or non-racemic mixtures of isomers, or pharmaceutically acceptable salts or solvates thereof together with one or more pharmaceutically acceptable carriers, and optionally other therapeutic and/or prophylactic ingredients.

The present disclosure provides for methods of treating fungal and parasitic infections using the compounds of the present disclosure. The fungal or parasitic infections can be superficial or systemic. The methods of the present disclosure comprise administering to the subject a therapeutically effective amount of the compounds of the present disclosure.

In general, the compounds of the present disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present disclosure for a given disease.

Thus, the compounds of the present disclosure can be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. In certain aspects, the manner of administration is intravenous, oral, or topical using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present disclosure, generally a therapeutic amount will be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In certain aspects, the present disclosure provides for a pharmaceutical composition comprising one of the compounds of Structure (I), (II), (III), or (IV) together with one or more pharmaceutically acceptable vehicles. In certain aspects, the pharmaceutically acceptable vehicle is an excipient. In further aspects, the pharmaceutically acceptable excipient is a permeation enhancer excipient.

Oral Administration

In certain aspects, the pharmaceutical compositions of the present disclosure are suitable for oral administration. For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compounds of the present disclosure can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Thus, for example, capsules can be prepared by conventional procedures so that the dosage unit is 100 mg of the compounds of the present disclosure, 100 mg of cellulose and 10 mg of magnesium stearate. A large number of unit capsules can also prepared by filling standard two-piece hard gelatin capsules each with 100 mg of powdered active ingredient, 150 mg of lactose, 50 mg of cellulose, and 10 mg magnesium stearate. Or, tablets can be prepared by conventional procedures so that the dosage unit is 100 mg of the compounds of the present disclosure, 150 mg of lactose, 50 mg of cellulose and 10 mg of magnesium stearate. A large number of tablets can also be prepared by conventional procedures such that the dosage unit was 100 mg of the compounds of the present disclosure, and other ingredients can be 0.2 mg of colloidal silicon dioxide, 5 mg of magnesium stearate, 250 mg of microcrystalline cellulose, 10 mg of starch and 100 mg of lactose. Appropriate coatings can be applied to increase palatability or delay absorption.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

In addition to the elements described above, the oral drug delivery systems of the present invention can also comprise pharmaceutically acceptable excipients such as carriers, binders, stabilizers, bulking agents, preserving agents (e.g., methyl-, ethyl-, and propyl-hydroxy-benzoates, butylated hydroxytoluene, butylated hydroxyanisole), sweetening agents, flavoring agents, coloring agents, lubricating agents, wetting agents, emulsifying agents, solubilizing agents, suspending agents, and disintegrating agents (e.g., crospovidone, croscarmellose sodium). The system can be provided in any dosage form suitable for oral administration such as a tablet, a capsule, a pellet, a granule, fine granules, a lozenge, and a powder. Preferably, the system is administered in the form of a tablet or capsule.

Parenteral Administration

In certain aspects, the pharmaceutical compositions of the present disclosure are suitable for parenteral administration.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the present disclosure into the body of a patient through a needle or a catheter, propelled by a sterile syringe or some other mechanical device such as an continuous infusion system. A formulation provided by the present disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the present disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

The formulations can optionally contain an isotonicity agent. The formulations preferably contain an isotonicity agent, and glycerin is the most preferred isotonicity agent. The concentration of glycerin, when it is used, is in the range known in the art, such as, for example, about 1 mg/mL to about 20 mg/mL.

The pH of the parenteral formulations can be controlled by a buffering agent, such as phosphate, acetate, TRIS or L-arginine. The concentration of the buffering agent is preferably adequate to provide buffering of the pH during storage to maintain the pH at a target pH±0.2 pH unit. The preferred pH is between about 7 and about 8 when measured at room temperature.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) can optionally be added to the formulation, and can be useful if the formulations will contact plastic materials. In addition, the parenteral formulations can contain various antibacterial and antifungal agents, for example, parabens, chlorobutanol, phenol, sorbic acid, thimerosal, and the like.

Sterile injectable solutions are prepared by incorporating one or more of the compounds of the present disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Topical Administration

In certain aspects, the pharmaceutical compositions of the present disclosure are suitable for topical administration. In certain aspects, the pharmaceutical compositions comprise the compounds of Structures (I), (II), (III), or (IV), a pharmaceutically acceptable topical carrier, and a permeation enhancer. In some aspects, the permeation enhancer comprises a base. In certain aspects, the base is present at a concentration sufficient to provide a formulation pH in the range of approximately 7.5 to 13.0, preferably about 8.0 to 11.5, and most preferably about 8.5 to 10.5.

In certain aspects, the pharmaceutical composition is aqueous. In some aspects, the aqueous pharmaceutical composition is a cream, gel, lotion, paste, or solution. In certain aspects, the pharmaceutical compositions of the present dislcosuer further comprise a pharmaceutically acceptable topical carrier; a skin-permeation enhancing agent comprising an inorganic hydroxide; and a therapeutically effective amount of any one of the compounds of Structure (I), (II), (III), or (IV). In certain aspects, the inorganic hydroxide is ammonium hydroxide, alkali metal hydroxide, alkaline earth metal hydroxide, or a combination thereof. In further aspects, the inorganic hydroxide is ammonium hydroxide, sodium hydroxide, calcium hydroxide, potassium hydroxide, magnesium hydroxide, or a combination thereof. In yet further aspects, the inorganic hydroxide is sodium hydroxide.

In various aspects, the present pharmaceutical compositions comprise a base. In further aspects, the base is an inorganic base. Exemplary inorganic bases are inorganic hydroxides, inorganic oxides, inorganic salts of weak acids, and combinations thereof. Preferred inorganic bases are those whose aqueous solutions have a high pH, and are acceptable as food or pharmaceutical additives. Examples of such preferred inorganic bases are those listed below, along with their respective pHs. Some of the bases are identified by their hydrate forms, and it is understood that when referring to a "base," both the hydrated and non-hydrated forms are intended to be included.

In certain aspects, the present pharmaceutical compositions comprise an inorganic base. Exemplary inorganic bases with their respective pHs and concentrations are provided below: ammonium hydroxide (pH 11.27 (1 N), pH 10.27 (0.001 N)); sodium hydroxide (pH 14 (5%), pH 13 (0.5%), pH 12 (0.05%)); potassium hydroxide (pH 13.5 (0.1 M)); calcium hydroxide (pH 12.4 (saturated solution in water)); magnesium hydroxide (pH 9.5 to 10.5); slurry magnesium oxide (pH 10.3 (saturated aqueous solution)); calcium oxide (soluble in water as $Ca(OH)_2$); sodium acetate (pH 8.9 (0.1 N)); sodium acetate, trihydrate (pH 8.9 (0.1 N);) sodium acetate, anhydrous (pH ~8.9 (0.1 N)); sodium borate decahydrate (pH 8.8-9.4, 9.15 to 9.2 (0.01 M)); sodium borate (pH 8.8-9.4, 9.15 to 9.2 (0.01 M)); sodium metaborate (strongly alkaline); Sodium carbonate (pH ~11.6); Sodium carbonate hydrate (pH ~11.6); sodium carbonate anhydrous (pH ~11.6); sodium bicarbonate (pH 8.3 (0.1 M fresh)); sodium phosphate, tribasic (pH ~11.5 (0.1%), pH ~11.7 (0.5%), pH ~11.9 (1.0%)); sodium phosphate, tribasic dodecahydrate (pH 11.5 (0.1%), pH 11.7 (0.5%), pH 11.9 (1.0%)); sodium phosphate, dibasic (pH 9.1 (1%) anhydrous); sodium phosphate, dibasic, heptahydrate (pH ~9.5); sodium phosphate, dibasic (pH ~9.5); sodium phosphate, dibasic, dehydrate (pH ~9.5); sodium phosphate, dibasic, dodecahydrate (pH ~9.5); potassium carbonate (pH ~11.6); potassium bicarbonate (pH 8.2 (0.1 M)); potassium citrate (pH ~8.5); potassium citrate, monohydrate (pH 8.5); potassium acetate (pH 9.7 (0.1 M)); potassium phosphate (aqueous solution is slightly alkaline dibasic); potassium phosphate, tribasic (aqueous solution is strongly alkaline); ammonium phosphate dibasic (pH ~8). Additional details regarding suitable inorganic bases and their respective pHs can be found in the "Chemicals in Compliance with Pharmaceutical Standards: Inactive Ingredient Guide," the "Handbook of Pharmaceutical Additives," and the FDA's food additive database In certain aspects, the present pharmaceutical compositions comprise an inorganic hydroxide. Inorganic hydroxides include, for example, ammonium hydroxide, alkali metal hydroxide and alkaline earth metal hydroxides, and mixtures thereof. Preferred inorganic hydroxides include ammonium hydroxide; monovalent alkali metal hydroxides such as sodium hydroxide and potassium hydroxide; divalent alkali earth metal hydroxides such as calcium hydroxide and magnesium hydroxide; and combinations thereof.

The amount of inorganic hydroxide included in the compositions and systems of the present disclosure, will typically represent about 0.3-7.0 wt %, preferably 0.5-4.0 wt %, more preferably about 0.5-3.0 wt %, most preferably about 0.75-2.0 wt %, of a topically applied formulation or of a drug reservoir of a drug delivery system, or patch.

The formulation may be in any form suitable for topical application, for example to the skin or nail and surrounding tissues, and may comprise, for example, a cream, lotion, solution, gel, ointment, paste, plaster, paint, bioadhesive, or the like, and/or may be prepared so as to contain liposomes, micelles, and/or microspheres. For those formulations in which the pharmacologically active base is a hydroxide-releasing agent, it is preferred although not essential that water be present. Thus, such a formulation may be aqueous, i.e., contain water, or may be nonaqueous and optionally used in combination with an occlusive overlayer so that moisture evaporating from the body surface is maintained within the formulation upon application to the body surface and thereafter.

Formulations of the invention may optionally contain a pharmaceutically acceptable viscosity enhancer and/or film former. A viscosity enhancer increases the viscosity of the formulation so as to inhibit its spread beyond the site of application. Balsam Fir (Oregon) is an example of a pharmaceutically acceptable viscosity enhancer.

A film former, when it dries, forms a protective film over the site of application. The film inhibits removal of the active ingredient and keeps it in contact with the site being treated. An example of a film former that is suitable for use in this invention is Flexible Collodion, USP. As described in Remington: The Science and Practice of Pharmacy, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former may act additionally as a carrier. Solutions that dry to form a film are sometimes referred to as paints.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Creams, as also well known in the art, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Plasters are comprised of a pasty mixture that is spread on the body, either directly or after being saturated into a base material such as cloth. Medications, including the bases of the invention, may be dissolved or dispersed within the plaster to make a medicated plaster.

Bioadhesives are preparations that adhere to surfaces of body tissues. Polymeric bioadhesive formulations are well known in the art; see, for example, Heller et al., "Biodegradable polymers as drug delivery systems," in Chasin, M. and Langer, R., eds.: Dekker, New York, pp. 121-161 (1990); and U.S. Pat. No. 6,201,065. Suitable non-polymeric bioadhesives are also known in the art, including certain fatty acid esters (U.S. Pat. No. 6,228,383).

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art to be comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the nail and surrounding tissues.

Microspheres, similarly, may be incorporated into the present formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids. Preparation of microspheres is well known in the art and described in the pertinent texts and literature.

Although the bases herein are particularly effective permeation enhancers in topical formulations for the treatment of nail funguses, it may be desirable, for other uses and particularly with weaker bases or thicker nails, to include an added permeation enhancer in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and C.sub.10 MSO may also be used, but are less preferred.

Most preferred enhancers are those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter of plasticizing enhancers is in the range of about 2.5 to about 10, preferably in the range of about 5 to about 10. Such enhancers are described in detail in co-pending, commonly assigned U.S. patent application Ser. No. 09/738,410, filed on Dec. 14, 2000, which is now U.S. Pat. No. 6,586,000, and in International Patent Application No. PCT/US00/34483, filed on Dec. 15, 2000, published Jun. 21, 2001 as WO 01/43775 A2. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a C.sub.2 -C.sub.4 alkane diol or triol, are substituted with one or two fatty ether substituents.

Additional permeation enhancers will be known to those of ordinary skill in the art of topical drug delivery, and/or are described in the pertinent texts and literature. See, e.g., Percutaneous Penetration Enhancers, Smith et al., editors (CRC Press, 1995).

Various additives, known to those skilled in the art, may be included in the topical formulations. For example, solvents, including relatively small amounts of alcohol, may be used to solubilize certain formulation components. The present formulations may also include conventional additives such as opacifiers, antioxidants, fragrance, colorants, gelling agents, thickening agents, stabilizers, surfactants, and the like. Other agents may also be added, such as antimicrobial agents, to prevent spoilage upon storage, i.e., to inhibit growth of microbes such as bacteria, yeasts, and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The formulations may also contain irritation-mitigating additives to minimize or eliminate the possibility of skin irritation or skin damage resulting from the base or other components of the composition. Suitable irritation-mitigating additives include, for example: -tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the composition.

The pharmaceutical compositions of the present disclosure can also be administered through the skin or nail and surrounding tissues using a conventional skin patch, wherein the agent is contained within a laminated structure that serves as a drug delivery device to be affixed to the body surface. In such a structure, the pharmaceutical formulation is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the nail or skin during drug delivery; typically, the adhesive material is a pressure-sensitive adhesive (PSA) that is suitable for long-term skin or nail contact, and that should be physically and chemically compatible with the base and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing drug, base, or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and nail and be worn comfortably on areas of skin such as at joints or other points of flexure, that are normally subjected to mechanical strain, with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the skin, nail and/or skin surrounding the nail. The release liner should be made from a drug/vehicle impermeable material, and is a disposable element that serves only to protect the device prior to application. Typically, the release liner is formed from a material impermeable to the pharmacologically active agent and the base, and which is easily stripped from the patch prior to use.

In an alternative embodiment, the active agent-containing reservoir and skin or nail contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly(hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be an active agent, an enhancer, or some other component contained in the drug delivery system. A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

In the case of nail treatment, the underlying surface of the transdermal device, i.e., the nail and skin contact area, has an area in the range of about 0.25 $cm^2$ to 12 $cm^2$, preferably about 0.5 $cm^2$ to 7 $cm^2$, more preferably about 1 $cm^2$ to 5 $cm^2$. That area will vary, of course, with the size of the area to be treated. Larger patches will be necessary to accommodate larger nails, whereas smaller patches can be used for smaller nails. In the case of skin treatment, the surface area of the transdermal device can be any suitable size corresponding to the infection area.

Such drug delivery systems may be fabricated using conventional coating and laminating techniques known in the art. For example, adhesive matrix systems can be prepared by casting a fluid admixture of adhesive, active agent and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture. In general, these patches are fabricated by solvent evaporation, film casting, melt extrusion, thin film lamination, die cutting, or the like. The active agent will generally be incorporated into the device during patch manufacture rather than subsequent to preparation of the device.

In a preferred delivery system, an adhesive overlayer that also serves as a backing for the delivery system is used to better secure the patch to the skin or nail and surrounding tissue. This overlayer is sized such that it extends beyond the drug reservoir so that adhesive on the overlayer comes into contact with the body surface. In certain aspects, the overlayer will make contact with the skin surrounding the nail, while the drug reservoir is positioned over the nail, particularly the infected portions of the nail. The overlayer is useful because the adhesive/drug reservoir layer may lose its adhesion a few hours after application due to hydration. By incorporating such adhesive overlayer, the delivery system remains in place for the required period of time.

Other types and configurations of topically applied drug delivery systems may also be used in conjunction with the present invention, as will be appreciated by those skilled in the art of topical drug delivery. See, for example, Ghosh, Transdermal and Topical Drug Delivery Systems (Interpharm Press, 1997), particularly Chapters 2 and 8.

Miscellaneous Modes of Administration

Alternatively, the pharmaceutical compositions of the present disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the present disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Formulations for buccal administration include tablets, lozenges, gels and the like. Alternatively, buccal administration can be effected using a transmucosal delivery system as known to those skilled in the art. The compounds of the present disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compounds of the present disclosure can be formulated for aerosol administration, particularly to the respiratory tract and including intranasal administration. The compound will generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

Permeation Enhancers

Peroral delivery of hydrophilic drugs is one of the greatest challenges in biopharmaceutical research. Hydrophilic drugs usually present low bioavailability after oral administration. One of the causes of this low bioavailability is poor intestinal permeation through the paracellular pathway. This pathway is actually restricted by the presence of tight junctions at the apical side of the enterocytes. Permeation enhancers can advantageously improve bioavailability by improving intestinal permeation.

In certain aspects, pharmaceutical formulations of the present disclosure can comprise permeation enhancers. The term "permeation enhancer" or "penetration enhancer" as used herein refers to an agent that improves the rate of transport of a pharmacologically active agent (e.g., the compounds of Structures (I), (II), (III), and (IV)) across the skin (for transdermal drug delivery) or the intestinal mucosal surface (for oral drug delivery). Typically a permeation enhancer increases the permeability of skin or mucosal tissue to a pharmacologically active agent. Permeation enhancers, for example, increase the rate at which the pharmacologically active agent permeates through skin and enters the bloodstream Enhanced permeation effected through the use of permeation enhancers can be observed, for example, by measuring the flux of the pharmacologically active agent across animal or human skin as described in the EXAMPLE 9 herein below. An "effective" amount of a permeation enhancer as used herein means an amount that will provide a desired increase in skin or intestinal mucosa permeability to provide, for example, the desired depth of penetration of a selected compound, rate of administration of the compound, and amount of compound delivered.

The term "permeation enhancers" includes all enhancers which increase the flux of a permeant, drug, or other molecule across the skin or intestinal mucosa. In other words, all cell envelope disordering compounds, solvents, steroidal detergents, bile salts, chelators, surfactants, non-surfactants, fatty acids, and any other chemical enhancement agents are intended to be included.

Permeation enhancers are comprised of two primary categories of components, i.e., cell-envelope disordering compounds and solvents or binary systems containing both cell-envelope disordering compounds and solvents. Other categories of permeation enhancer are known, however, such as steroidal detergents, bile salts, chelators, surfactants, non-surfactants, and fatty acids.

Cell envelope disordering compounds are known in the art as being useful in topical pharmaceutical preparations and function also in drug delivery through the skin or mucosa. These compounds are thought to assist in dermal penetration by disordering the lipid structure of the stratum corneum cell-envelopes. It is believed that any cell envelope disordering compound is useful for purposes of this invention.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

An example of a permeation enhancer is chitosan for the transport of a hydrophilic compound like the compounds of Structures (I), (II), (III), or (IV). The structure of chitosan is shown below as Structure (VI):

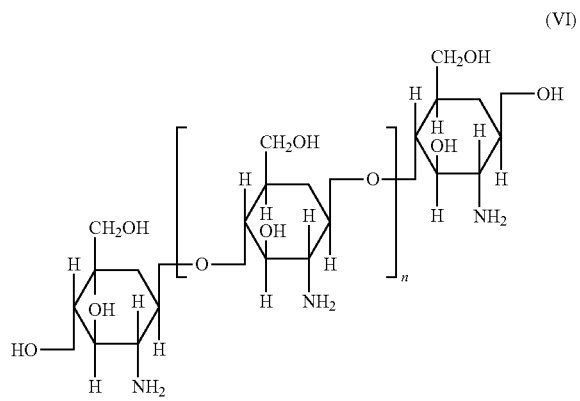

(VI)

Without being bound by any particular theory, the mechanism underlying chitosan's permeation enhancing effect seems to be based on the positive charges of chitosan, which interact with the cell membrane resulting in a structural reorganization of tight junction-associated proteins. The permeation enhancing effect of chitosan can advantageously improved by the immobilization of thiol groups for example by using chitosan-4-thiobutylamidine (chitosan-TBA). The structure of chitosan-TBA is shown below as Structure (VII):

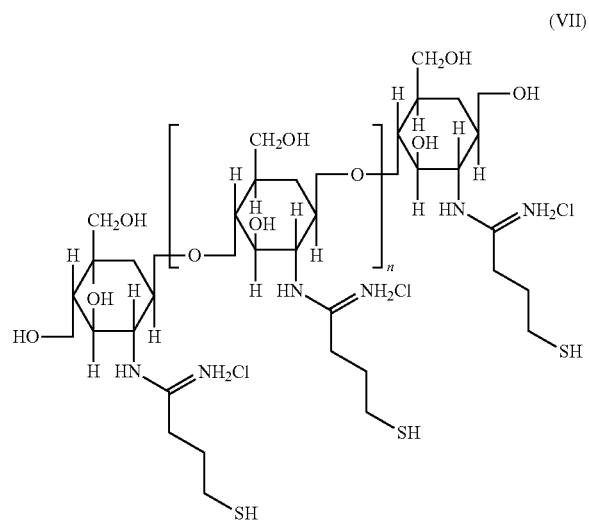

(VII)

Thiolated chitosans also display, besides their strong mucoadhesive and permeation enhancing properties, excellent cohesive properties. The reduced thiol functions on the chitosan backbone enable thiolated chitosans not only to form disulfide bonds with mucus glycoproteins, but also to form inter- as well as intra-molecular disulfide bonds. Such a cross-linking of the polymeric chains results in a high stability of drug carrier systems.

One possible mechanism for improving permeation enhancement is through the inhibition of the enzyme, tyrosine phosphatase. This enzyme seems to be involved in the opening and closing process of the tight junctions. Thus, the presently disclosed pharmaceutical compositions can comprise any permeation enhancing agent that inhibits tyrosine phosphatase. For instance, inhibition of tyrosine phosphatase can be carried out by compounds such as phenylarsine oxide, pervanadate or reduced glutathione leads consequently to phosphorylation and opening of the tight junctions. In certain aspects, the present pharmaceutical compositions comprise glutathione. In further aspects, the glutathione is in a reduced state.

In certain aspects, the present disclosure provides for a pharmaceutical composition comprising the compounds of the present disclosure together with one or more pharmaceutically acceptable vehicles. In certain aspects, the pharmaceutically acceptable vehicle is an excipient. In further aspects, the pharmaceutically acceptable excipient is a permeation enhancer excipient. In further aspects, the pharmaceutically acceptable excipient is a polymer. In certain aspects, the polymer is a polycation, polyanion, thiolated polymer, or a combination thereof. In some aspects, the polymer is a polycation and the polycation is chitosan, a quaternary ammonium derivative of chitosan, poly-L-arginine, aminated gelatin, dimethylaminoethyl methacrylate-methyl methacrylate copolymer, a polyvinyl acetal diethylaminoacetate, or a combination thereof. In certain aspects, the polycation is chitosan. In some aspects, the polymer is a polyanion and the polyanion is N-carboxymethyl chitosan, poly-acrylic acid, or a combination thereof. In certain aspects, the polymer is a thiolated polymer and the thiolated polymer is carboxymethyl cellulose-cysteine, polycarbophil-cysteine, chitosan-thiobutylamidine, chitosan-thioglycolic acid, a chitosan-glutathione conjugate, or a combination thereof. In further aspects, the thiolated polymer is chitosan-4-thiobutylamidine. In yet further aspects, the thiolated polymer is a chitosan-glutathione conjugate. In further aspects, the permeation enhancer excipient is glutathione.

In various aspects, the pharmaceutically acceptable excipient has a concentration of between 0.1% to 40.0% w/w.

In certain aspects, the pharmaceutically acceptable excipient comprises a combination of chitosan-4-thiobutylamidine and glutathione. In certain aspects, the pharmaceutically acceptable excipient comprises 0.1% to 1.0% chitosan-4-thiobutylamidine and 1% to 10% glutathione. In further aspects, the pharmaceutically acceptable excipient comprises 0.25% to 0.75% chitosan-4-thiobutylamidine and 2.5% to 7.5% glutathione. In yet further aspects, the pharmaceutically acceptable excipient comprises 0.5% chitosan-4-thiobutylamidine and 5% glutathione.

Enteric Coats

In various aspects, the pharmaceutical compositions of the present disclosure can be enterically coated. The enteric coating polymer material, i.e., the polymer which does not dissolve in the stomach but in the small intestine, can be any pharmaceutically-acceptable polymer material. In particular, polymer materials which dissolve at a pH of about 6 or higher are preferred. Examples of suitable enteric coating polymers include, without limitation, a methyl methacrylate-methacrylic acid (1:1) copolymer (e.g., Eudragit L; Rohm & Haas Co.), a methyl methacrylate-methacrylic acid (2:1) copolymer (e.g., Eudragit S; Rohm & Haas Co.), an ethyl acrylate-methacrylic acid (1:1) copolymer (e.g., Eudragit LD-55; Rohm & Haas Co.), hydroxypropylmethylcellulose phthalate (JPXII), cellulose acetate phthalate (JPXII), shellac (JPXII), and combinations thereof. Preferably, the enteric coating polymer is a methyl methacrylate-methacrylic acid (1:1) copolymer (e.g., Eudragit L). The polymer can further comprise a plasticizer such as triacetin, Macrogol 400, triethyl citrate, Tween 80, castor oil, etc., as well as minerals such as magnesium silicate hydroxide (i.e., talc). The enteric coating polymer is present in an amount of from about 1% to about 50% w/w, preferably from about 1% to about 20% w/w, more preferably from about 1% to about 10% w/w. In a preferred embodiment, the enteric coat comprises an enteric coating polymer (e.g., Eudragit L100), triethyl citrate, magnesium silicate hydroxide (i.e., talc), and optionally, a drug and a buffering agent.

In certain aspects, the pharmaceutical compositions of the present disclosure are formulated in an enterically coated time-controlled release pharmaceutical dosage form. In certain aspects, the enteric coating is a fat-fatty acid mixture, cellulose acetate phthalate, acrylic acid polymer, acrylic acid copolymer, alkyl-substituted acrylic acid polymer, alkyl-substituted acrylic acid copolymer, or a combination thereof. In some aspects, the enteric coating is polyvinyl acetate phthalate, titanium dioxide, talc, colloidal silicon dioxide, triethyl citrate, polyethylene glycol, sodium bicarbonate, purified stearic acid, sodium alginate, methyl methacrylate-methylacrylate acid (1:1) copolymer, a methyl methacrylate-methacrylate acid (2:1) copolymer, an ethyl acrylate-methacrylic acid (1:1) copolymer, hydroxypropylmethylcellulose phthalate, cellulose acetate phthalate, shellac, or a combination thereof. In further aspects, the enteric coating is an acrylic acid-containing and methacrylic acid-containing polymer. In yet further aspects, the enteric coating is poly(methylmethacrylate-co-methacrylic acid).

In certain aspects, the enteric coating further comprises a buffering agent.

Methods of Treatment

In various aspects, the compounds of the present disclosure have antifungal activity. A compound is considered to have antifungal activity if it has an inhibitory effect on fungus. Fungus is inhibited if it is killed, the growth of the fungus is prevented, or if the growth of the fungus is slowed. The antifungal compound can have an inhibitory effect on any form of fungus.

In various aspects, the compounds of the present disclosure have antibacterial activity. A compound is considered to have antibacterial activity if it has an inhibitory effect on bacteria. Bacteria is inhibited if it is killed, the growth of the bacteria is prevented, or if the growth of the bacteria is slowed. The antibacterial compound can have an inhibitory effect on any form of bacteria.

In further aspects, the compounds of the present disclosure have antiparasitic activity. A compound is considered to have antiparasitic activity if it has an inhibitory effect on a parasite. A parasite is inhibited if it is killed, the growth of the parasite is prevented, or if the growth of the parasite is slowed. The antiparasitic compound can have an inhibitory effect on any form of parasite, such as, for example, nematodes, cestodes, trematodes, infectious protozoa, or amoebas. In some aspects, the compounds of the present disclosure inhibit protozoal parasites. In further aspects, the compounds of the present disclosure inhibit the protozoal parasite *Naegleria*. In further aspects, the compounds of the present disclosure inhibit the protozoal parasite *Leishmania*.

In certain aspects, the present disclosure provides methods for treating or inhibiting a fungal infection in a subject, the method comprising administering to the subject an effective amount of a compound of Structure (I):

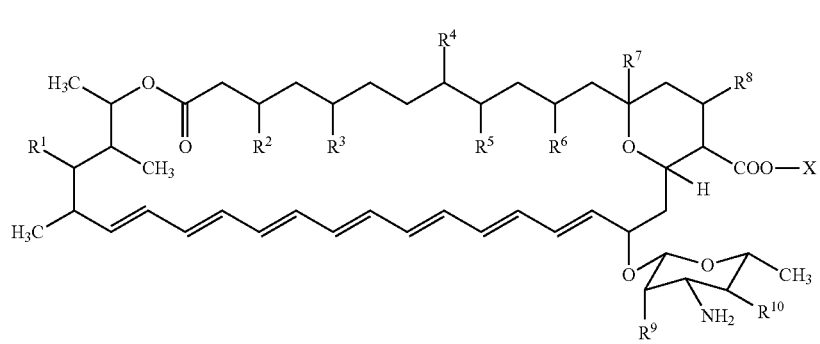

(I)

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation.

In certain aspects of Structure (I), $R^1$, $R^2$, $R^3$, $R^4$, $R^5$, $R^6$, $R^7$, $R^8$, $R^9$, and $R^{10}$ are each independently —OH or hydrogen.

In certain aspects of Structure (I), $R^1$, $R^2$, $R^3$, $R^4$, $R^5$, $R^6$, $R^7$, $R^8$, $E^9$, nd $R^{10}$ are each independently —OH.

In certain aspects of Structure (I), X is an inorganic cation.

In certain aspects of Structure (I), X is a cation of sodium, potassium, aluminum, calcium, lithium, magnesium, or zinc.

In certain aspects of Structure (I), X is a cation of sodium.

In certain aspects of Structure (I), X is a cation of potassium.

In certain aspects of Structure (I), X is a cation of calcium.

In certain aspects of Structure (I), X is a cation of aluminum, calcium, lithium, magnesium, or zinc.

In certain aspects of Structure (I), X is an organic cation.

In certain aspects of Structure (I), X is a cation of an amine, $C_1$-$C_{10}$ alkyl, halo-$C_1$-$C_6$ alkyl, $C_2$-$C_6$ alkenyl, $C_2$-$C_6$ alkynyl, $C_1$-$C_6$ sulfinylalkyl, $C_1$-$C_6$ sulfonylalkyl, $C_1$-$C_6$ thioalkyl, $C_1$-$C_6$ aminoalkyl, $C_1$-$C_6$ hydroxyalkyl, arylalkyl, cycloalkyl, heterocycle, or heteroaryl.

In certain aspects of Structure (I), X is a cation of an amine and the amine is tetramethylammonium, ammonia, ethylenediamine, N-methylglucamine, lysine, arginine, orthinine, choline, N,N' dibenzylethylenediamine, chloroprocaine, diethanolamine, procaine, N-benzylphenethylamine, 1-p-chlorobenzyl-2-pyrrolidine-1'-methylbenzimidazole, diethylamine, piperazine, morpholine, 2, 4, 4-trimethyl-2-pentamine, or tris(hydroxymethyl)aminomethane.

In certain aspects, the method treats a systemic fungal infection. In certain aspects, the method treats a non-systemic fungal infection. In some aspects, the fungal infection is onychomycosis. In certain aspects, the subject is immunocompromised. In further aspects, the subject is immunocompromised by AIDS, cancer, or treatment with immunosuppressant agents.

In certain aspects, the compound is administered orally. In further aspects, the compound is administered parenterally. In further aspects, the compound is administered topically.

In certain aspects, the compound of Structure (I) has one of the following Structures (II), (III), or (IV):

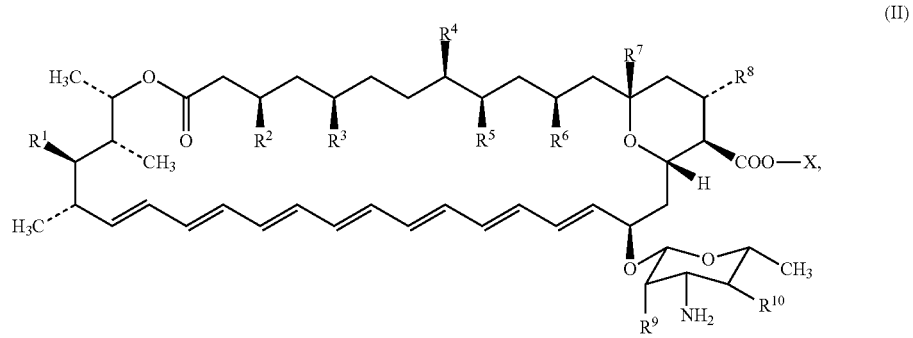

(II)

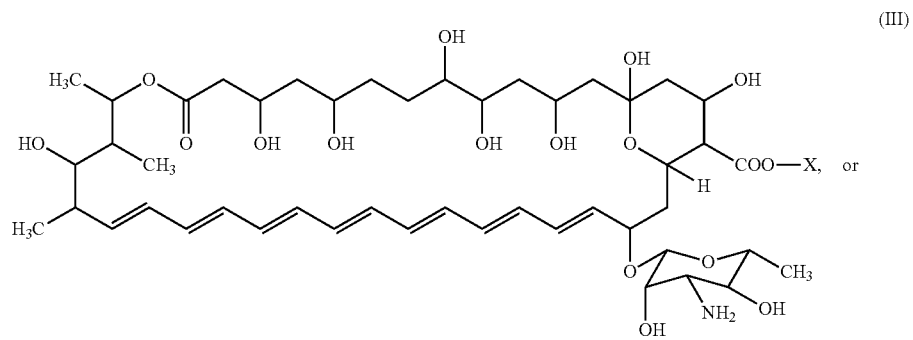

(III)

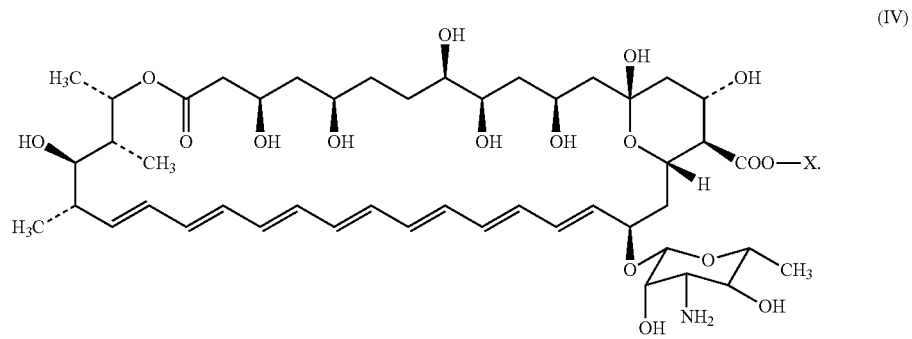

(IV)

In certain aspects, the present disclosure provides methods for treating or inhibiting a parasitic infection in a subject, the method comprising administering to the subject an effective amount of a compound of Structure (I):

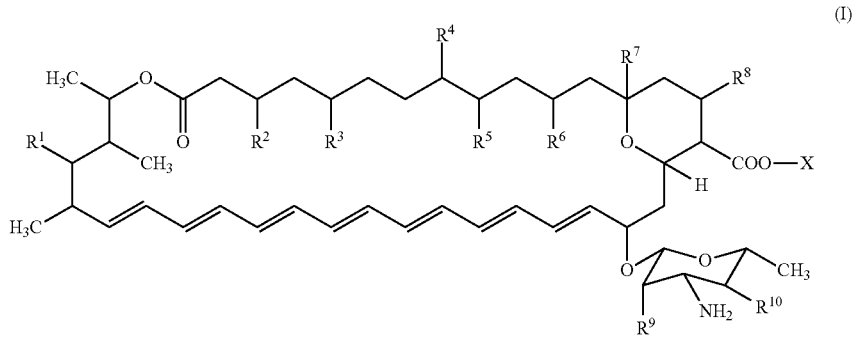

(I)

or a pharmaceutically acceptable isomer thereof, wherein:

$R^1$, $R^2$, $R^3$, $R^4$, $R^5$, $R^6$, $R^7$, $R^8$, $R^9$, and $R^{10}$ are each independently hydrogen, —OH, —SH, amino, nitro, cyano, halo, optionally substituted $C_1$-$C_6$ alkoxy, optionally substituted $C_1$-$C_6$ alkanoyl, amide, carboxy, or ester; and X is a pharmaceutically acceptable cation.

In certain aspects of Structure (I), $R^1$, $R^2$, $R^3$, $R^4$, $R^5$, $R^6$, $R^7$, $R^8$, $R^9$, and $R^{10}$ are each independently —OH or hydrogen.

In certain aspects of Structure (I), $R^1$, $R^2$, $R^3$, $R^4$, $R^5$, $R^6$, $R^7$, $R^8$, $R^9$, and $R^{10}$ are each independently —OH.

In certain aspects of Structure (I), X is an inorganic cation.

In certain aspects of Structure (I), X is a cation of sodium, potassium, aluminum, calcium, lithium, magnesium, or zinc.

In certain aspects of Structure (I), X is a cation of sodium.

In certain aspects of Structure (I), X is a cation of potassium.

In certain aspects of Structure (I), X is a cation of calcium.

In certain aspects of Structure (I), X is a cation of aluminum, calcium, lithium, magnesium, or zinc.

In certain aspects of Structure (I), X is an organic cation.

In certain aspects of Structure (I), X is a cation of an amine, $C_1$-$C_{10}$ alkyl, halo-$C_1$-$C_6$ alkyl, $C_2$-$C_6$ alkenyl, $C_2$-$C_6$ alkynyl, $C_1$-$C_6$ sulfinylalkyl, $C_1$-$C_6$ sulfonylalkyl, $C_1$-$C_6$ thioalkyl, $C_1$-$C_6$ aminoalkyl, $C_1$-$C_6$ hydroxyalkyl, arylalkyl, cycloalkyl, heterocycle, or heteroaryl.

In certain aspects of Structure (I), X is a cation of an amine and the amine is tetramethylammonium, ammonia, ethylenediamine, N-methylglucamine, lysine, arginine, orthinine, choline, N,N' dibenzylethylenediamine, chloroprocaine, diethanolamine, procaine, N-benzylphenethylamine, 1-p-chlorobenzyl-2-pyrrolidine-1'-methylbenzimidazole, diethylamine, piperazine, morpholine, 2,4, 4-trimethyl-2-pentamine, or tris(hydroxymethyl)aminomethane.

In certain aspects, the method treats a systemic parasitic infection. In certain aspects, the method treats a non-systemic parasitic infection. In some aspects, the parasitic infection is of the central nervous system. In certain aspects, the parasitic infection is of the internal organs. In further aspects, the parasitic infection is of the skin.

In certain aspects the parasitic infection is a protozoal infection. In some aspects, the parasitic infection is leishmaniasis. In further aspects, the parasitic infection is visceral leishmaniasis. In yet further aspects, the parasitic infection is cutaneous leishmaniasis. In some aspects, the parasitic infection is primary amoebic meningoencephalitis.

In certain aspects, the compound is administered orally. In further aspects, the compound is administered parenterally. In further aspects, the compound is administered topically.

In certain aspects, the compound of Structure (I) has one of the following Structures (II), (III) or (IV):

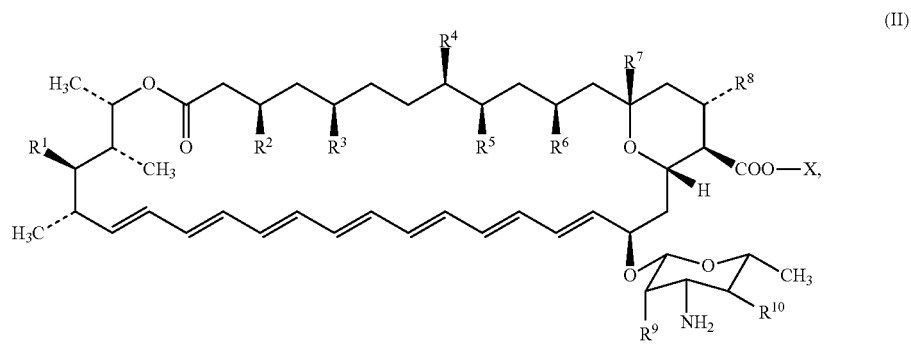

(II)

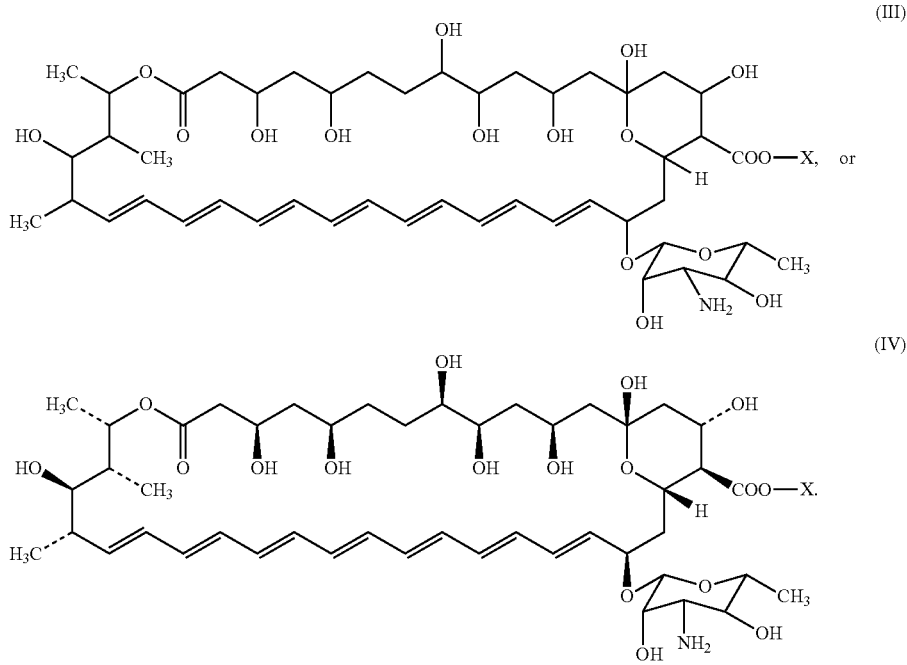

The term "treating" includes the administration of the compounds or agents of the present invention to a subject to prevent or delay, to alleviate, or to arrest or inhibit development of the symptoms or conditions associated with fungal or parasitic infections. A skilled medical practitioner will know how to use standard methods to determine whether a patient is suffering from a disease associated with a fungal or parasitic infection, e.g., by examining the patient and determining whether the patient is suffering from a disease known to be associated with a fungal or parasitic infection or by assaying for fungus or parasite levels in blood plasma or tissue of the individual suspected of suffering from a fungal or parasitic infection. Accordingly, the present invention provides, inter alia, methods of administering a compound of the present invention to a subject and determining the presence of a fungal or parasitic infection in the subject. Fungal or parasitic infections in the subject can be determined before and/or after administration of the compound.

A "therapeutically effective amount" means the amount of a compound that, when administered to a patient for treating a disease, is sufficient to effect such treatment for the disease. The "therapeutically effective amount" will vary depending on the compound, the disease and is severity and the age, weight, etc., of the patient to be treated, and can be determined by one of skill in the art without undue experimentation.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary aspect of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that are associated with the targeted or suspected disease or condition. These and other routine methods allow the clinician to select patients in need of therapy using the methods and formulations of the present invention.

Methods of Topically Treating Fungal or Parasitic Infections

In various aspects, the presently described compounds can be used to topically treat fungal or parasitic infections. For instance, the present pharmaceutical compositions can be administered for the treatment of cutaneous leishmaniasis (a parasitic infection of the skin) and onychomycosis (a fungal infection of the nail).

Cutaneous leishmaniasis is the most common form of leishmaniasis. It is a skin infection caused by a single-celled parasite that is transmitted by sandfly bites. There are about 20 species of Leishmania that may cause cutaneous leishmaniasis. In certain aspects, cutaneous leishmaniasis can be treated by administering a therapeutically effective amount of one of the compounds of Structure (I), (II), (III), or (IV).

Fungal infections of the nail, referred to by the terms "nail fungus," "onychomycosis," or "tinea unguium," are common throughout the world. An estimated 2-13% of the population is affected in North America, with at least 15-20% of those aged 40-60 having one or more fingernails or toenails infected. Infections can range from superficial, causing little more than discoloration, to severe, resulting in loss of the nail together with deformities of the surrounding digit. The incidence of onychomycosis has been rising over the past few decades, due to factors such as an increased elderly population, increased participation in vigorous physical activity while wearing moisture-retaining shoes and socks, an increase in the number of HIV infected individuals, an increased incidence of diabetes, and increased use of steroids, antibiotics, and other therapeutics that can suppress immunologic responses to fungi. In certain aspects, onychomycosis can be treated by administering a therapeutically effective amount of one of the compounds of Structure (I), (II), (III), or (IV).

In various aspects, a cream, ointment, paste, plaster, or lotion may be spread on the affected area or gently rubbed in. Similarly, a polymeric or other bioadhesive formulation may be spread or dabbed on the affected area. A solution may be applied in the same ways, but more typically will be applied with a dropper, swab, or the like, and carefully applied to the affected area. Petrolatum may be spread on the skin surrounding the affected area to protect it from possible irritation during treatment.

The dose regimen will depend on a number of factors that may readily be determined, such as the areal extent and thickness of the affected skin or nail and the responsiveness of the infection to treatment, but will normally be one or more doses per day, with a course of treatment lasting from several weeks to several months, or until a cure is effected or a significant reduction of the infection is achieved. One of ordinary skill may readily determine optimum dosages, dosing methodologies and repetition rates. In general, it is contemplated that the formulation will be applied one to four times daily. With a skin patch, the device is generally maintained in place on the body surface throughout a drug delivery period, typically in the range of 8 to 72 hours, and replaced as necessary.

These and other aspects of the present disclosure will become evident upon reference to the following detailed description. In addition, various references are set forth herein which describe in more detail certain procedures or compositions, and are therefore incorporated by reference in their entirety.

Exemplary Aspects

Below are examples of specific embodiments for carrying out the present disclosure. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

EXAMPLE 1

Production of Corifungin

The compounds of the present disclosure were synthesized using a microorganism, particularly a strain of *Streptomyces nodosus* NRRL B-2371. The microorganism was maintained as a stock in frozen vials: For transfers contents of a frozen vial is thawed and inoculated into 100 mL liquid seed (SD-01) 1.0% dextrose, 0.3% soya fluff; 0.3% brewer's yeast in 300-mlFul-Baf Tunair flasks (Tunac, J Ferment Bioeng, 68:15 - 159 (1989)). The flasks were incubated at 28° C. on a 245 rpm shaker for 2 days. For the fermentation production of the compound a complex medium composed of 4.0% dextrose; 2.0% soya fluff; 0.5% brewer's yeast; 0.5% calcium carbonate, incubated at 28° C. on a 245 rpm shaker. For optimum antibiotic yields the flasks were usually harvested 3-4 days after inoculation.

The compound is produced by fermentation using proprietary fermentation media. Production of the samples was carried out in high-aeration flasks: the Tunair flask (http://www.sheltonscientific.com) system (Tunac, J Ferment Bioeng, 68:15 - 159 (1989)).

Production of additional compounds was carried out on proprietary bioreactors (Tunac, U.S. Pat. No. 5,075,234 (1991)), including 25-, 100-, 500-gal size Airmentors.

To start the fermentation process, the seed of *Streptomyces sp.* was prepared in the Tunair shake flask, and then successively transferred to larger size vessels. The number of seed transfers depends on the final size of the production Airmentor. A typical sequence would be a seed prepared initially in a 300-mL Tunair flask, incubated by shaking overnight, then 10-mL growth transferred to a 3-L Tunair flask; three 3-L Tunair seed flasks would be used to inoculate a 25-gal production Airmentor. The 25-gal Airmentor was incubated for 3 days.

The fermentation medium was prepared by dissolving or suspending the ingredients in water and subsequently sterilizing the resulting medium by autoclaving or by steam heating. The sterilized medium was cooled to a temperature of between 16° C. and 45° C., inoculated with the microorganism, and thereafter fermentation was carried out with aeration and agitation using either shake-flasks or stationary tank fermentors. In shake-flasks, aeration is achieved by agitating the flasks to bring about intimate mixing of the inoculated medium with air. In stationary tank fermentors, agitation is provided by impellers, which can take the form of disc turbines, vaned discs, or open turbine or marine propellers. Aeration is accomplished by sparging air or oxygen into the agitated mixture.

The biological activity of the fermentation broths was assayed by the agar diffusion assay involving *Saccharomyces cerevisiae* (RSY) and *Aspergillus terreus* (MEVS).

25-Gal Stirred-Jar Fermentation

A cryogenic vial containing approximately 1 mL of a suspension of the culture was used to inoculate 100 mL of seed culture medium (SCM) in a 300-mL Tunair Ful-Baf shake flask. The inoculated flask was incubated for about 16-24 hours at 28° C. for 16-24 hours shaking (180 rpm gyratory shaker, 5-cm throw). After sufficient growth is obtained, 10-mL aliquots of the microbial growth were transferred aseptically to four 2-L Erlenmeyer seed flasks containing a 500-mL of SCM. The inoculated medium was incubated at 28° C. for 16-24 hours shaking (180 rpm gyratory shaker, 5-cm throw). The microbial growth from these four flasks were pooled and used to inoculate a 25-gal Airmentor. The production fermentor contained 20 gallons (80 liters) of production culture medium (CPM), which was 'steam sterilized' for 40 minutes at 121.degree. C. The medium was cooled to 28° C. before inoculation. Fermentation was carried out for about 20 hours, stirred at 155 rpm, and sparged with air at 1 CFM air. A silicone-based antifoam was used to control foaming as needed.

Isolation and purification. After growth has been completed, mycelium is separated from the whole broth by filtration or centrifugation and the mycelium is extracted with 3 parts ethyl acetate. Ethyl acetate extract was evaporated in vacuo to dryness then washed with acetone yielding a pale yellow powder, which was dried in a desiccator. The yellow powder was further processed as illustrated below:

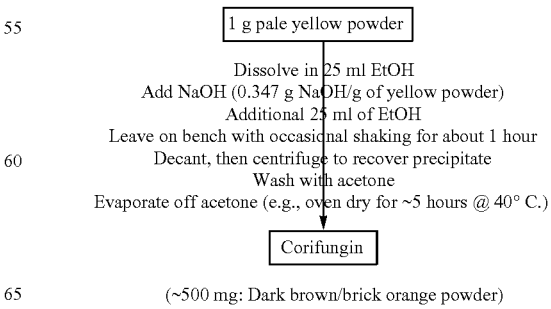

(~500 mg: Dark brown/brick orange powder)

EXAMPLE 2

Characterization of Corifungin

LC-MS Analysis:

A series of LC-MS analyses were performed to determine the composition of the above sample with the following conditions:

Column: Phenomenex Luna C18, 250×4.6 mm, 5 µm, p/n 00G-4252-E0
UV Detection: DAD (200-600 nm)
Mobile Phase A: $H_2O$ (5 mM $NH_4OAc$)
Mobile Phase B: Acetonitrile (5 mM $NH_4OAc$)
Flow Rate: 1000 µL/min
Temperature: Ambient
Injection volume: 30 µL
Gradient:

| Time | % A | % B |
|------|-----|-----|
| 0.0  | 90  | 10  |
| 40.0 | 40  | 60  |
| 40.1 | 90  | 10  |
| 47.0 | 90  | 10  |

FIG. 1 shows the results of the LC-MS analysis of the corifungin sample dissolved in DMSO-methanol (1:1). The major peak in the UV chromatogram was observed at 33.18 min (33.58 min in the ELS and 33.18 min in the TIC). The mass spectrum corresponding to this peak is shown in the second panel of FIG. 1 and indicated a potential [M+H]+ ion at m/z 924 (i.e., the molecular weight of amphotericin B).

Figure 2:
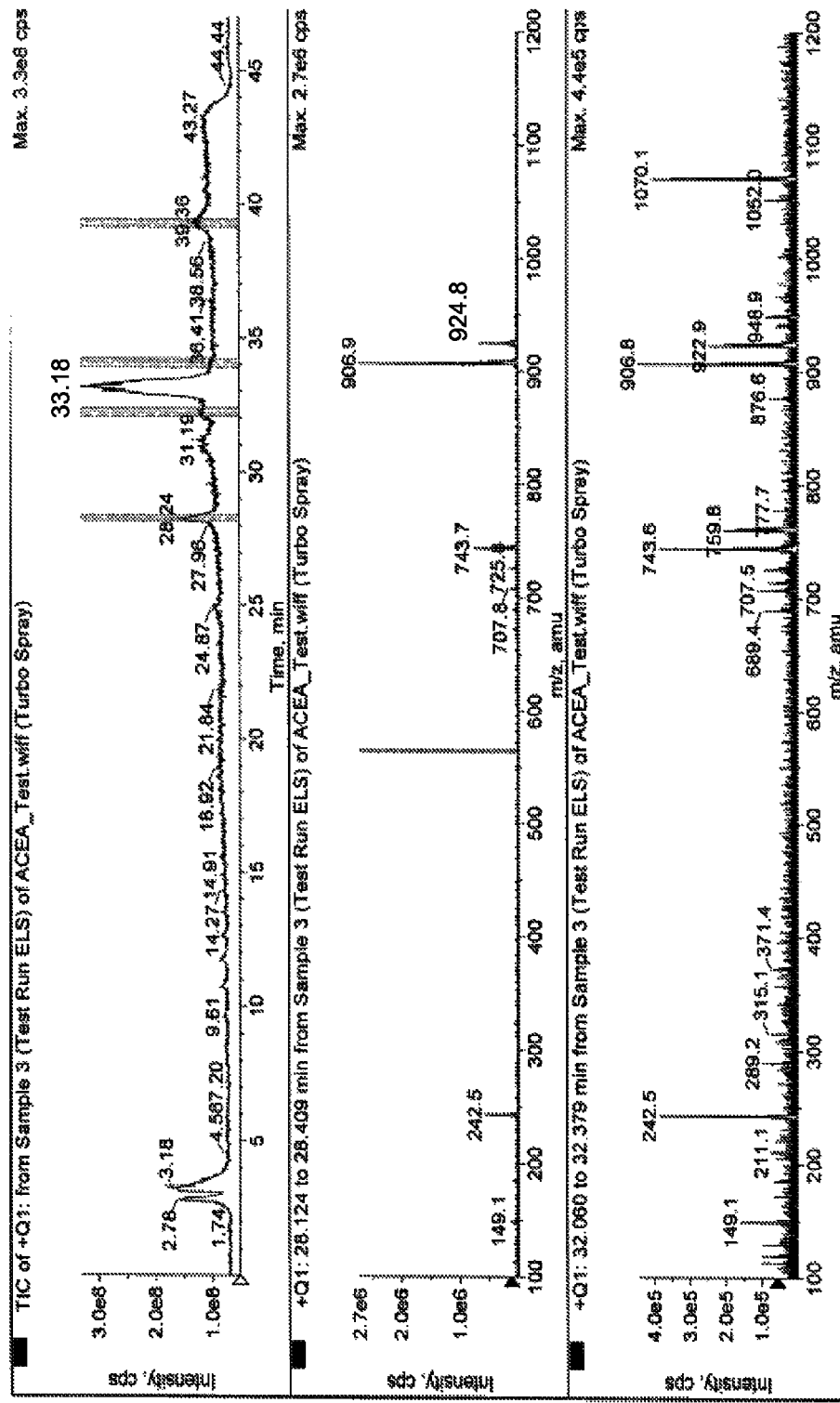
FIG. 2 shows the mass spectra corresponding to the minor peaks observed in FIG. 1.

Also, the mass spectra for several of the minor peaks (28.24, 32.19, 33.98, and 39.35 min in the UV chromatogram shown in FIG. 1 were determined Anaysis of the mass spectra for the minor peaks indicated that each appears to be related to the main component in the sample as shown in FIG. 2.

Figure 3:
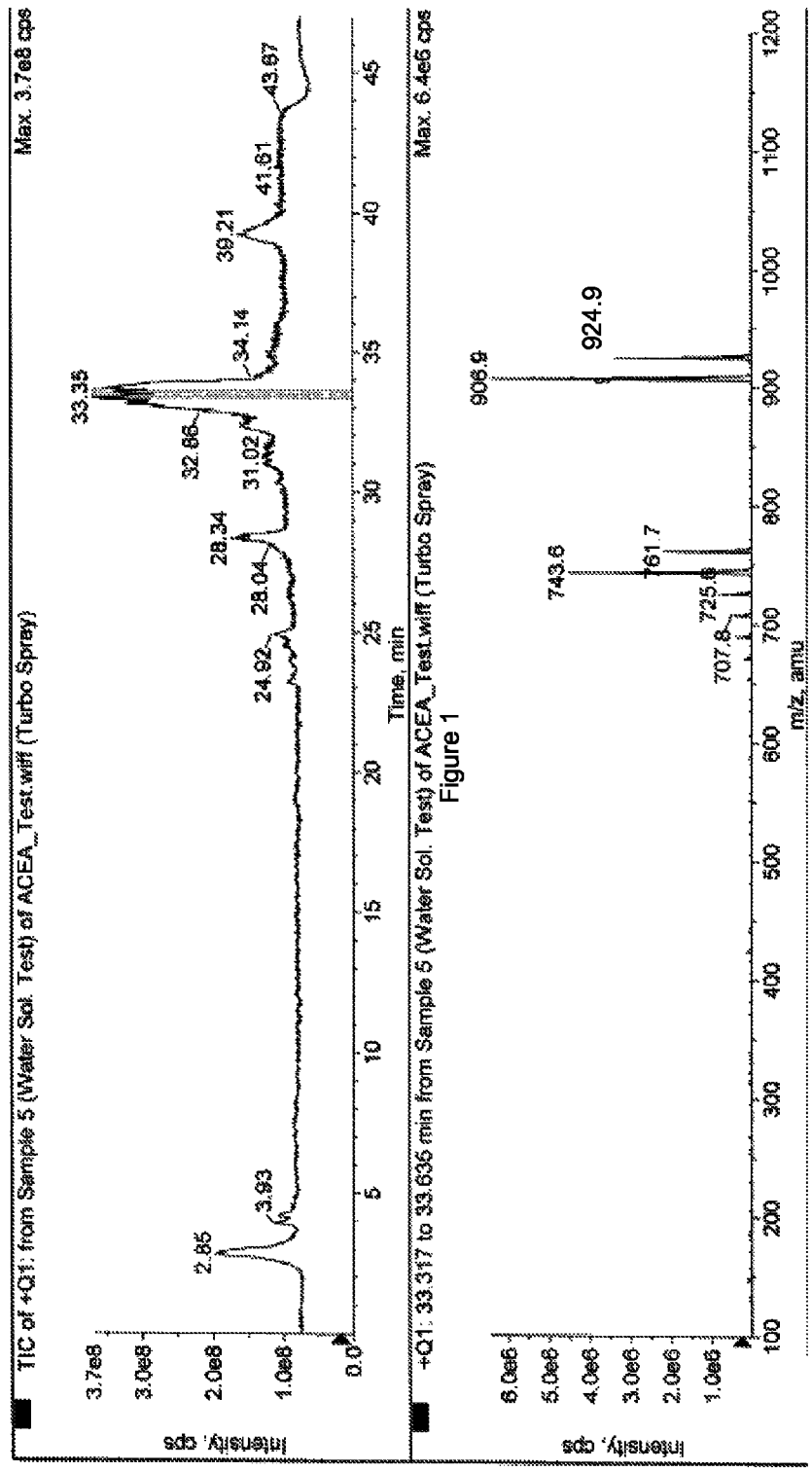
FIG. 3 shows the LC-MS analysis of corifungin solubilized in $H_2O$ including the TIC, mass spectrum of the major peak, UV chromatogram, and ELS chromatogram.

The LC-MS of corifungin dissolved in water is shown in FIG. 3. As with the analysis in DMSO-methanol, the major peak in the UV chromatogram of FIG. 3 corresponds to m/z 924 (i.e., the molecular weight of amphotericin B). As demonstrated by FIG. 3, corifungin is soluble in water.

Figure 4:
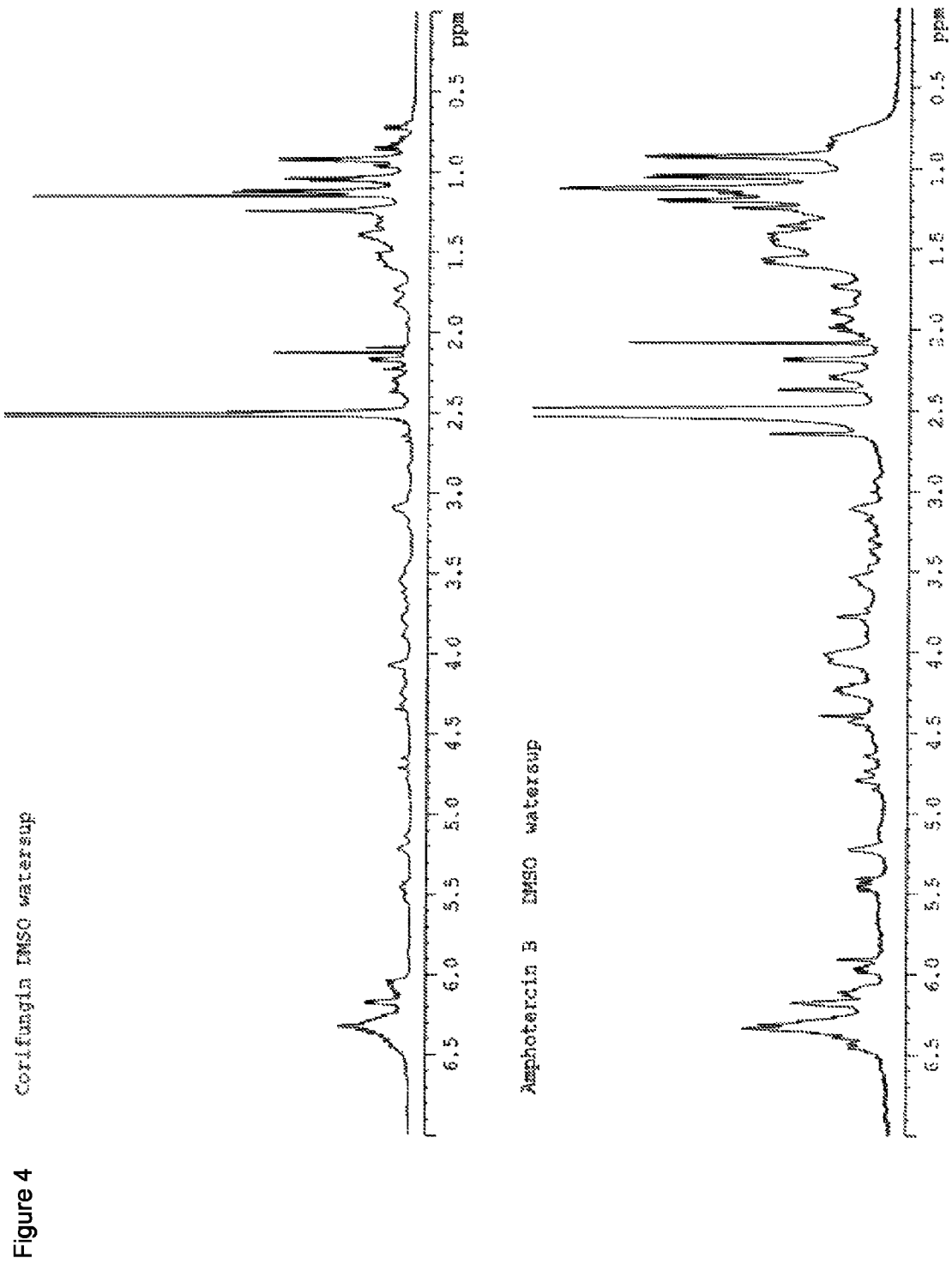
FIG. 4 shows the 1H NMR spectrum (500 MHz, DMSO-d6) of corifungin sample (Top) and amphotericin B (Bottom).

NMR Analysis:

The LC-MS data above suggests that the main component present in corifungin was indistinguishable from amphotericin B. The 1H NMR spectra, although generally similar, differed in several regions. These variations are likely due to variations in the sample composition, which could indicate that corifungin was in a salt form (FIG. 4).

Figure 5:
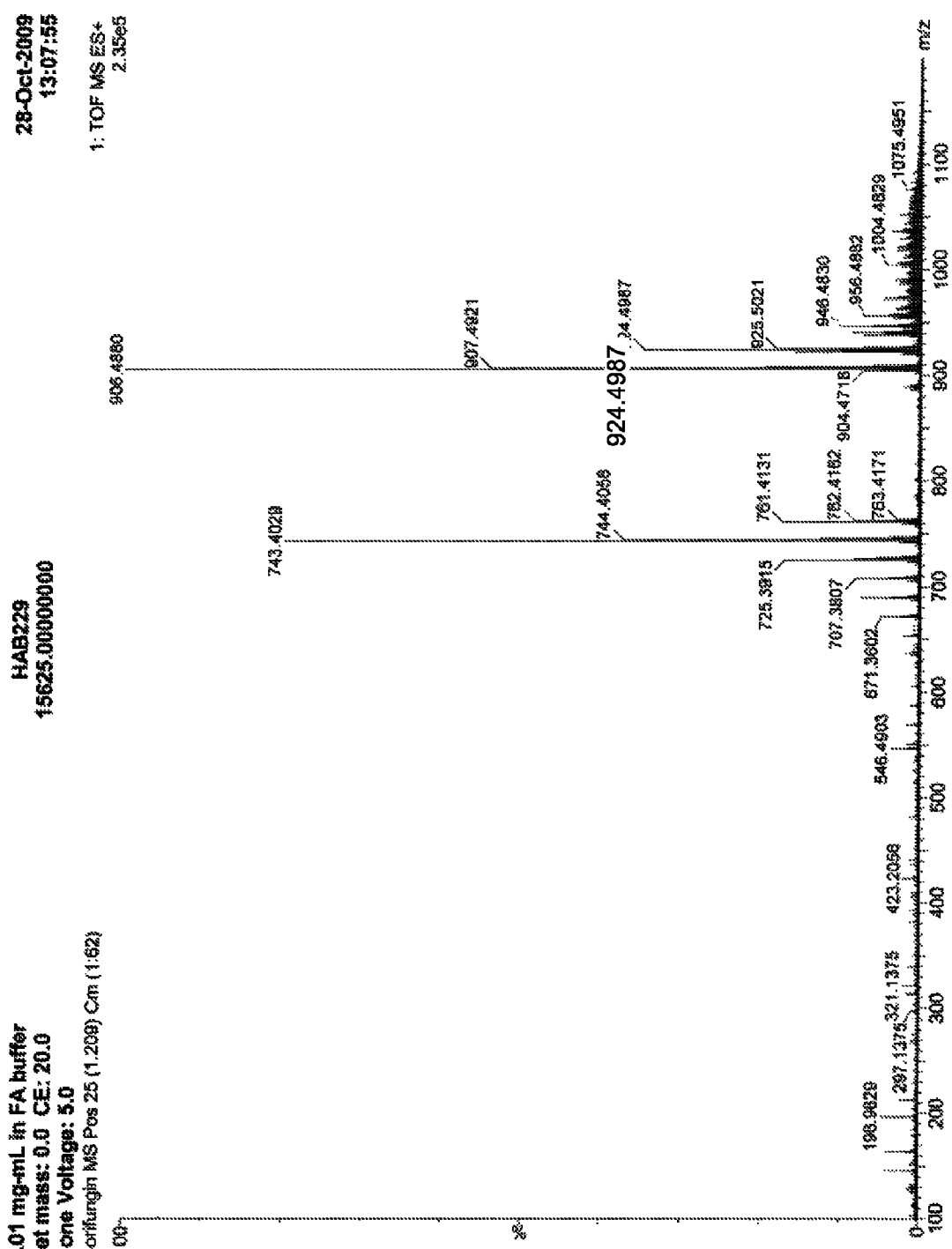
FIG. 5 shows the positive electrospray TOF mass spectrum of corifungin.

MS Analysis:

A sample of corifungin was prepared in a standard MS buffer consisting of acetonitile-$H_2O$ with 0.1% formic acid. This sample was analyzed on a Waters premier Q-Tof mass spectrometer. The positive electrospray ionization Tof mass spectrum is shown in FIG. 5.

The Tof mass spectrum provided results similar to those observed by LC-MS. Accurate mass analysis of [M+H]+ ion observed at m/z 924.4987 indicated that it was in good agreement with the molecular formula $C_{47}H_{73}NO_{17}$ (calculated mass for $C_{47}H_{74}NO_{17}$: 924.4957, error: 3.2 ppm) for the major component present in the corifungin sample (FIG. 6).

Figure 7:
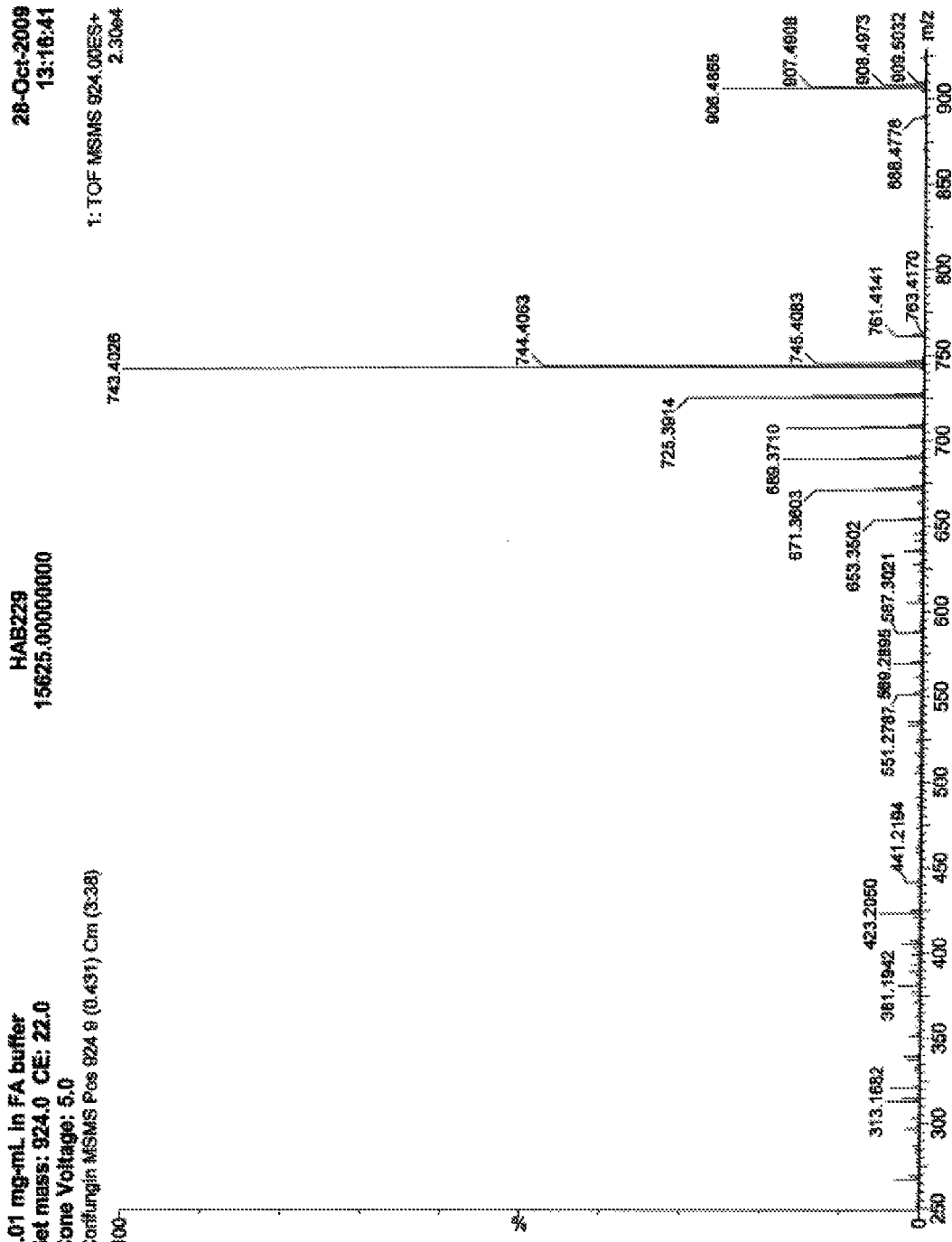
FIG. 7 shows the MS/MS analysis of corifungin, selecting the [M+H]+ ion at m/z 924 for fragmentation.

This is the same molecular formula as amphotericin B. The positive electrospray MS/MS analysis selecting the [M+H]+ ion at m/z 924 is shown in FIG. 7.

Figure 8:
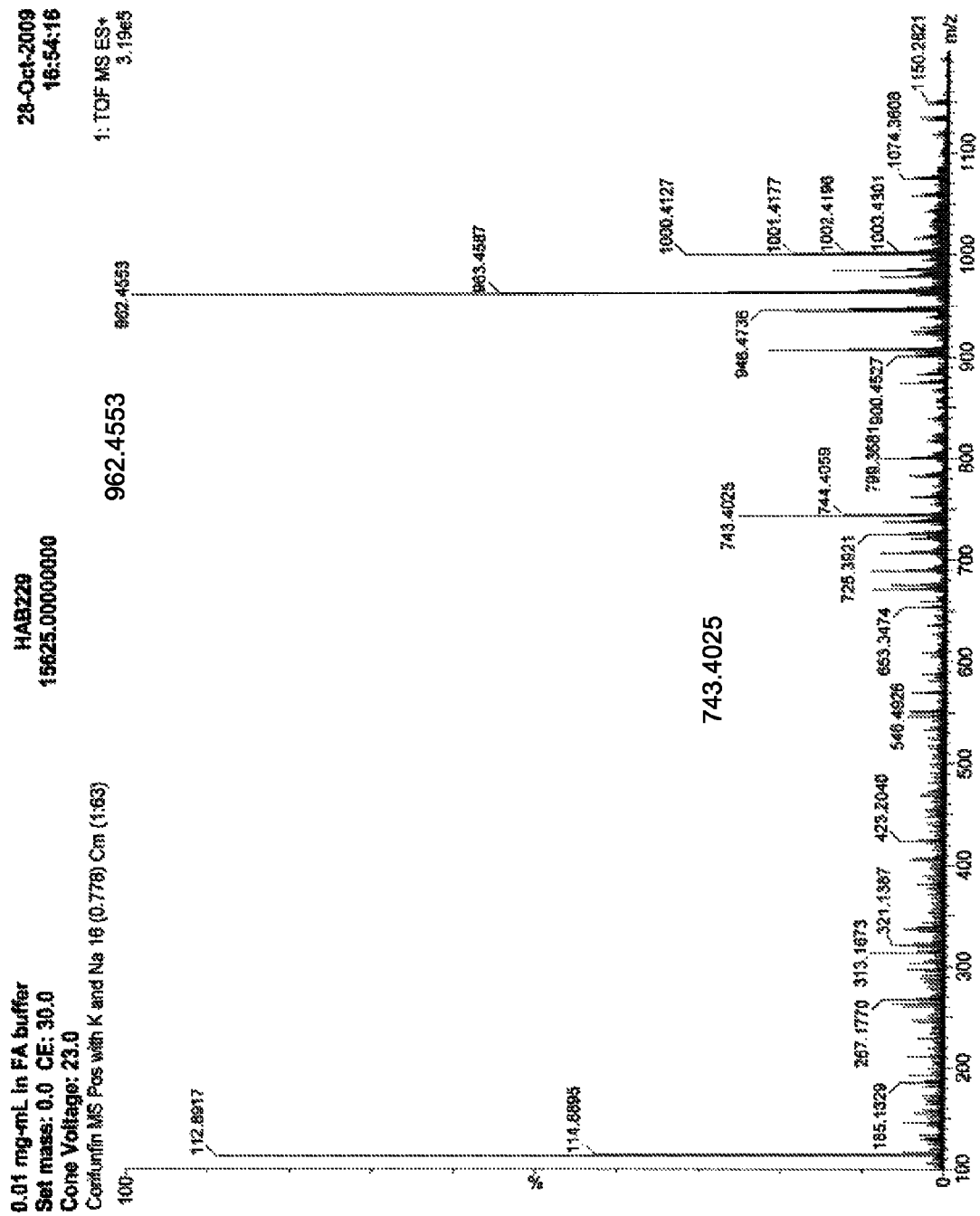
FIG. 8 shows the positive electrospray TOF mass spectrum of a K+ and Na+ doped sample of corifungin.

Significant ions were observed at m/z 906.4865 and 743.4026 which correspond to loss of $H_2O$ and loss of $H_2O$ together with the glycoside, respectively. The corifungin sample was further analyzed after the addition of a small amount of KCl and NaCl to the sample. As shown in FIG. 8, addition of K+ and Na+ allowed acquisition of a mass spectrum similar to that provided with the sample which showed a significant ion at m/z 962.4553, with little to no ion observed at m/z 924.

Figure 9:
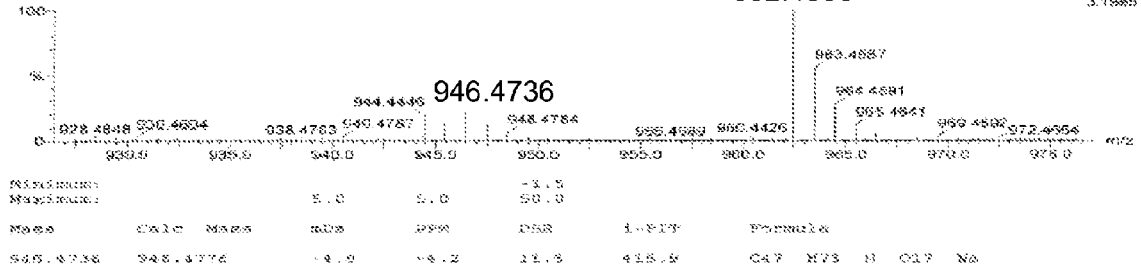
FIG. 9 shows the accurate mass analysis of the K+ and Na+ doped sample of corifungin.
Figure 9:
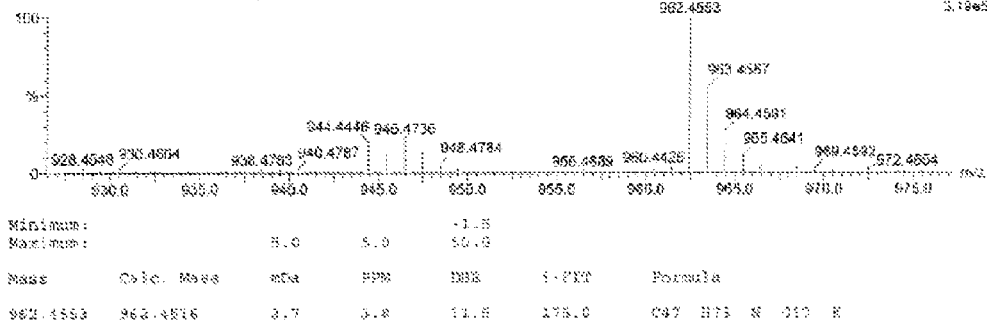

Accurate mass analysis of the ions at m/z 946.4736 and 962.4553 indicated that they correspond to the [M+Na]+ and [M+K]+ adducts, respectively, of the component with a molecular formula of $C_{47}H_{73}NO_{17}$ (FIG. 9).

Figure 10:
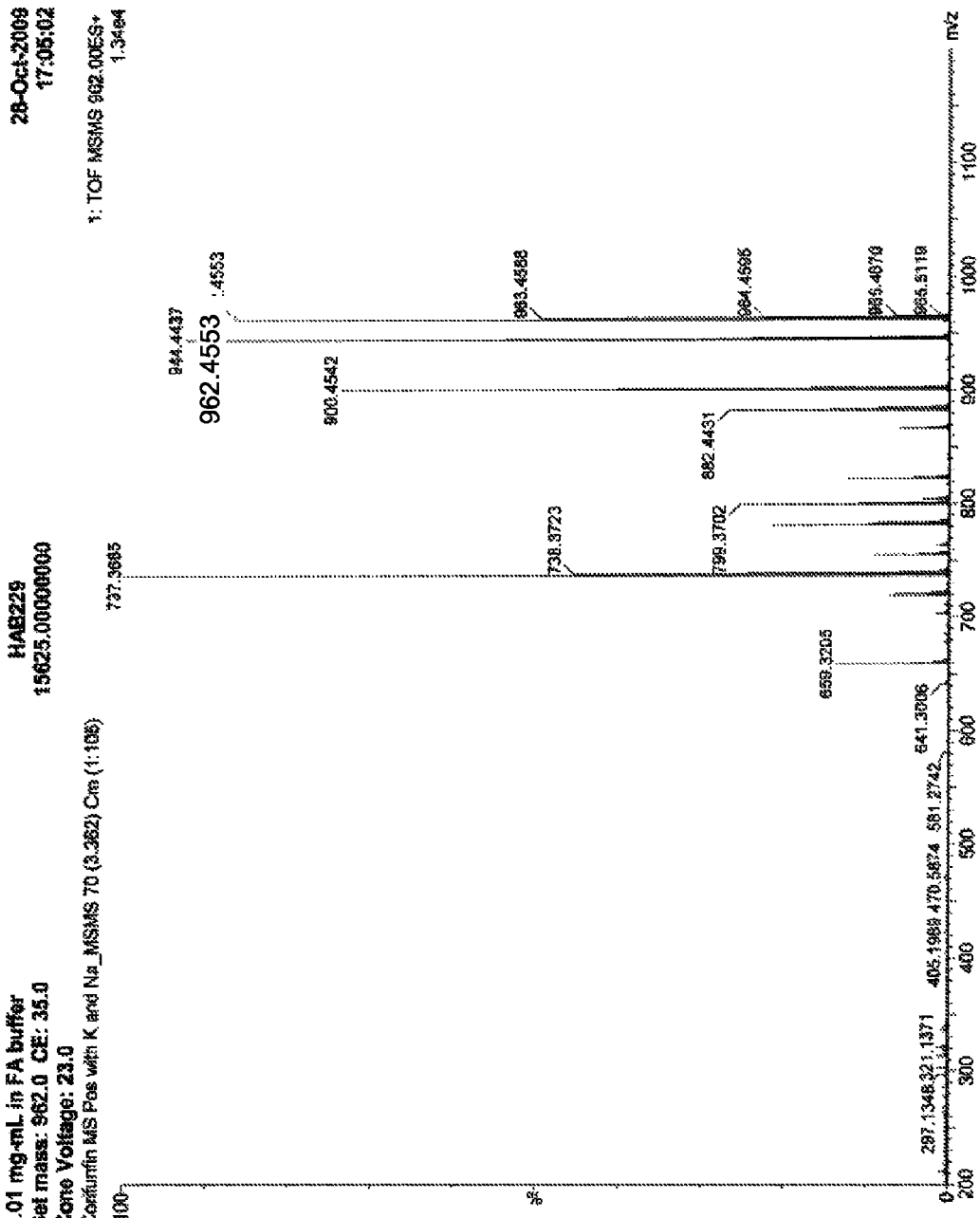
FIG. 10 shows the MS/MS analysis of the K+ and Na+ doped sample of corifungin, selecting the ion at m/z 962 for fragmentation.
Figure 11:
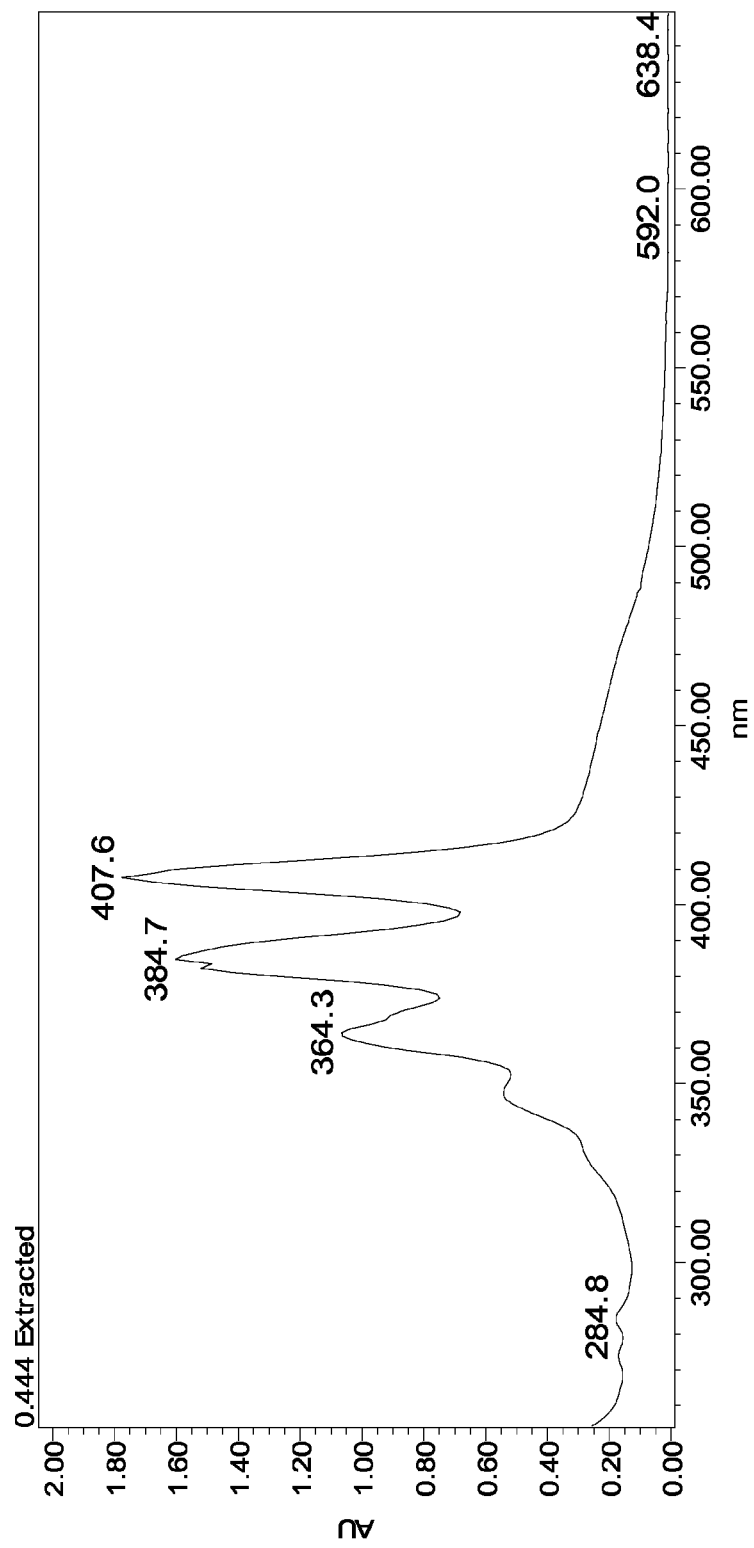
FIG. 11 shows the UV-Visible spectrum of corifungin.
Figure 12:
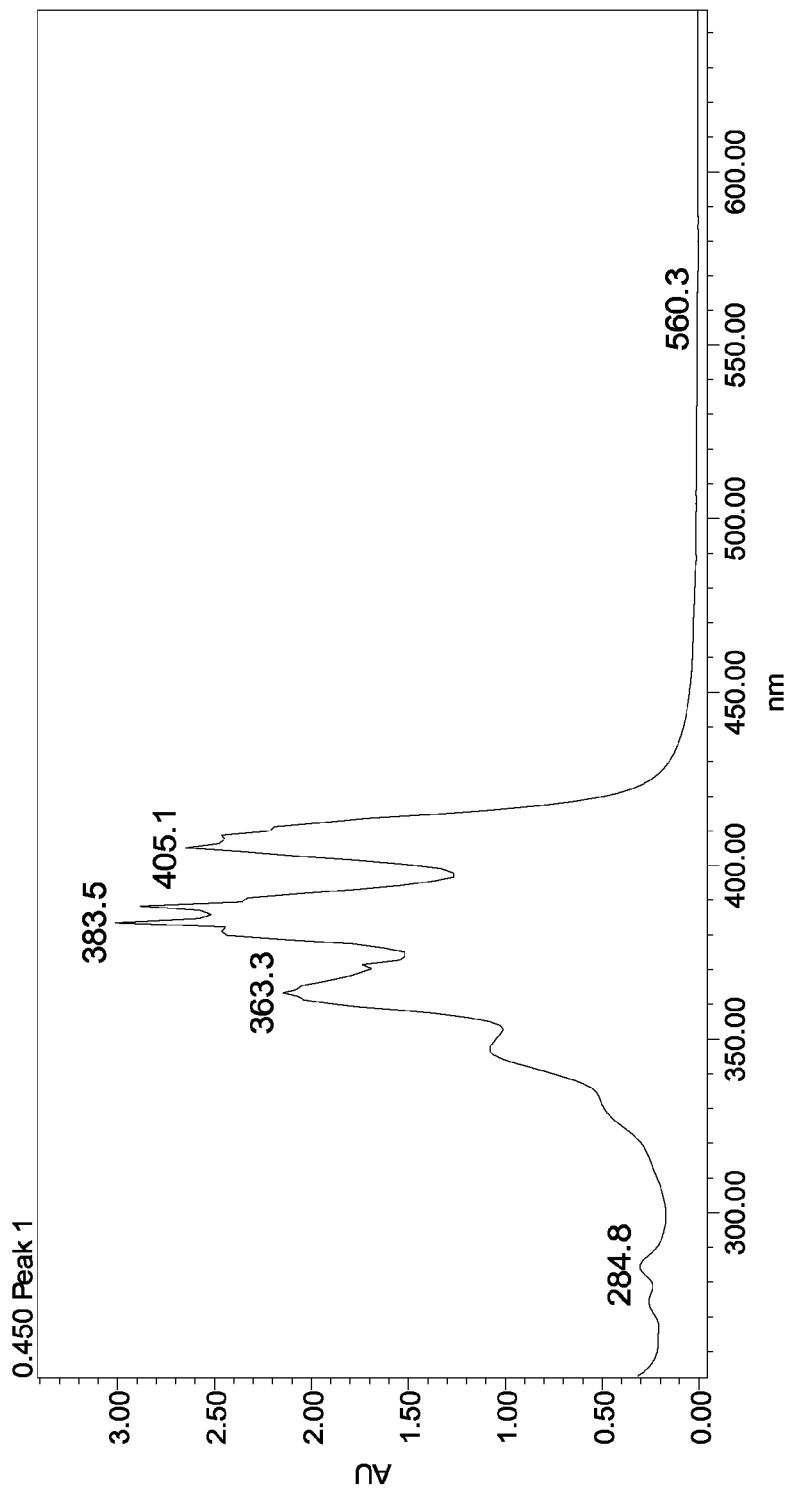
FIG. 12 shows the UV-Visible spectrum amphotericin B.

The positive electrospray MS/MS analysis selecting the [M+K]+ ion at m/z 962 is shown in FIG. 10 and was identical to the MS/MS spectrum provided with corifungin sample. These data, taken together, indicated that the ion observed at m/z 962 in the data provided is almost certainly the [M+K]+ ion of a component with the molecular formula $C_{47}H_{73}NO_{17}$.

UV-Vis Spectrum (0.050 mg/mL 10% DMSO/Methanol)

Chemical comparison: corifungin vs. amphothericin B. Corifungin was found to be a water-soluble sodium salt of amphotericin B. A summary of chemical properties of corifungin and amphotericin B is shown below in Table 1.

TABLE 1

Molecular weight, molecular formula and water-solubility properties of corifungin.

| | Molecular weight | Molecular formula | Water solubility |
|---|---|---|---|
| Corifungin | 946.5 | $C_{47}H_{73}NO_{17}Na$ | very soluble: |
| Amphotericin B | 924.5 | $C_{47}H_{73}NO_{17}$ | >100 mg/mL insoluble |

EXAMPLE 3

In Vitro Antifungal Activity

In-vitro antifungal susceptibility assays using CLSI M27-A2 for *Candida* species and CLSI M38-A for molds were adopted (Reference Method for Broth Dilution Antifungal Susceptibility Testing of Yeasts; Approved Standard-Second Edition. CLSI document M27-A2 [ISBN 1-56238-469-4]. CLSI, Pennsylvania, USA 200); activity expressed as minimum inhibitory concentration (MIC). In addition, MFC (mean fungicidal concentration) was done for each species. The geometric mean (GM) was calculated for each isolate using all three results. All testing was performed in triplicate to verify the reproducibility of the data.

Antifungal Activity Against *Candida, Aspergillus*, and Other Common Molds:

Eighty-three *Candida* strains were evaluated. This included 12 different *Candida* species, which are the species that are most commonly involved in the majority of candidal infections in humans. The species include ten isolates of *C. albicans, C. glabrata, C. parapsilosis, C. tropicalis, C. krusei, C. lusitaniae*, and *C. kefyr*, along with five isolates of *C. dubliniensis*, and two isolates each of *C. guilliermondii* and *C. rugosa*. In addition, there was also one isolate each of *C. sake, C. lipolytica, C. sphaerica* and *C. norvegica*.

The results of this study are shown in Table 2 below. These results demonstrate that corifungin has substantial in vitro activity against numerous *Candida* species. The mean minimal inhibitory concentration (MIC) of corifungin and amphotericin B for *C. albicans* was 0.5 µg/mL for both antifungals; for *C. tropicalis* 0.5 and 1 µg/mL; for *C. dubliniensis* 0.125 and 0.5 µg/mL; for *C. parapsilosis* 1 and 0.5 µg/mL; for *C. lusitaniae* 0.5 for both; for *C. krusei* and *C. glabrata* 1.0 µg/mL for both, respectively. See e.g., Table 2.

The lowest MICs for corifungin were seen in *C. albicans, C. lusitaniae* and *C. dubliniensis* at 0.5 µg/mL. Similarly, the MFCs for all of the *Candida* species evaluated were between 1-2 µg/mL for corifungin and amphotericin B.

TABLE 2

In vitro susceptibility assays comparing corifungin, amphotericin B and voriconazole against *Candida* spp.

| *Candida* spp. | Antifungal Agent | MIC (µg/mL) Range | $MIC_{50}$ | $MIC_{90}$ | GM | MFC |
|---|---|---|---|---|---|---|
| *C. albicans* (10) | corifungin | 0.12-1 | 0.5 | 1 | 0.612 | 2 |
| | Amphotericin B | 0.12-1 | 0.5 | 1 | 0.612 | 1 |
| | Voriconazole | <0.03-0.25 | 0.03 | 0.06 | 0.06 | nd |
| *C. glabrata* (10) | corifungin | 0.5-1.0 | 1 | 1 | 0.9 | 2 |
| | Amphotericin B | 0.5-1.0 | 1 | 1 | 0.9 | 1 |
| | Voriconazole | 0.12-2 | 0.5 | 0.5 | 0.56 | Nd |
| *C. parapsilosis* (10) | corifungin | 0.5-1.0 | 1 | 1 | 0.9 | 2 |
| | Amphotericin B | 0.5-1.0 | 0.5 | 1 | 0.7 | 2 |
| | Voriconazole | <0.03-0.12 | <0.03 | 0.03 | 0.04 | Nd |
| *C. tropicalis* (10) | corifungin | 0.5-1.0 | 1 | 1 | 0.95 | 2 |
| | Amphotericin B | 0.5-1.0 | 1 | 1 | 0.95 | 2 |
| | Voriconazole | <0.03-0.5 | 0.06 | 0.12 | 0.13 | Nd |
| *C. lusitaniae* (10) | corifungin | 0.25-1.0 | 0.5 | 1.0 | 0.575 | 2 |
| | Amphotericin B | 0.25-1.0 | 0.5 | 1.0 | 0.575 | 0.5 |
| | Voriconazole | <0.03-0.06 | <0.03 | 0.03 | 0.03 | Nd |
| *C. kefyr* (10) | corifungin | 0.5-2 | 1 | 2 | 1.02 | 2 |
| | Amphotericin B | 0.12-2.0 | 1 | 2 | 1.25 | 1 |
| | Voriconazole | <0.03-16 | <0.03 | 0.6 | 1.63 | Nd |
| *C. krusei* (10) | corifungin | 0.5-2.0 | 1 | 2 | 1.41 | 2 |
| | Amphotericin B | 0.5-2.0 | 1 | 2 | 1.29 | 2 |
| | Voriconazole | 0.25-0.5 | 0.25 | 0.5 | 0.425 | nd |
| *C. rugosa* (2) | corifungin | 0.5-1.0 | | | 0.83 | 2 |
| | Amphotericin B | 0.5-1.0 | | | 0.83 | 2 |
| | Voriconazole | 0.25 | | | 0.25 | Nd |
| *C. guilliermondii* (2) | corifungin | 0.5 | | | 0.5 | 1 |
| | Amphotericin B | 0.5 | | | 0.5 | 1 |
| | Voriconazole | 0.06 | | | 0.06 | Nd |
| *C. dubliniensis* (5) | corifungin | 0.125-1 | 0.125 | 1 | 0.375 | |
| | Amphotericin B | 0.125-1 | 0.5 | 1 | 0.4 | |
| Other *Candida* spp. (4) | corifungin | 0.5-1.0 | 1 | | 0.83 | 2 |
| | Amphotericin B | 0.5-1.0 | 1 | | 0.95 | 2 |
| | Voriconazole | <0.03-1.0 | 0.06 | | 0.39 | nd |

GM = geometric mean
Other *Candida* species (*C. lipolytica, C. sake, C. sphaerica, C. norvegica*)

A total of 31 isolates of *Aspergillus* were evaluated. This included six different species of *Aspergillus* which included six strains of *A. fumigatus*, and 5 strains of *A. flavus, A. terreus, A. niger* and *A. glaucus*.

Several of the more common molds were also tested and evaluated including five strains of *Alternaria, Cladosporium, Scopulariopsis, Acremonium*, and *Paecilomyces*. Also evaluated were some of the more uncommon fungi such as *Exophilia jeanselmei* (3), *Emmonsia parvum* (*Chrysporium parvum*) (2) and *Epioccum* spp. (2). Conventional ATCC strains of different *Candida* and *Aspergillus* species were used as controls.

The mean minimal inhibitory concentration ($MIC_{50}$) of corifungin and amphotericin B was 0.5 µg/mL for *A. glaucus*; 1 µg/mL for *A. niger* and *A. versicolor*, and 2 µg/mL for *A. fumigatus* and *A. flavus*, respectively (Table 3). Overall, the corifungin range for all *Aspergillus* strains tested was from 0.5-2.0 µg/mL, with the exception of one *A. flavus* isolate that displayed an MIC of 16 µg/mL. The highest $MIC_{50}$ was seen in the *A. terreus* strains, which are known to be either less susceptible to or intrinsically resistant to polyenes. In addition, corifungin also displayed excellent in vitro activity against a wide array of molds including *Alternaria, Cladosporium, Scopulariopsis*, and *Paecilomyces*. In contrast, *Acremonium* and *Exophilia* appear to be resistant to it.

TABLE 3

In vitro susceptibility assays comparing corifungin to amphotericin B and voriconazole against *Aspergillus* spp and other molds.

| Fungus | No. Isolates | corifungin | | | Amphotericin B | | |
|---|---|---|---|---|---|---|---|
| | | Range | $MIC_{50}$ | GM | Range | $MIC_{50}$ | GM |
| *Aspergillus* spp. | | | | | | | |
| *A. fumigates* | 6 | 0.5-2 | 2 | 1.75 | 0.5-2 | 2 | 1.58 |
| *A. niger* | 5 | 0.5-1 | 1 | 0.8 | 0.5-1 | 1 | 0.8 |
| *A. glaucus* | 5 | 0.25-1 | 0.5 | 0.7 | 0.25-1 | 0.5 | 0.7 |
| *A. terreus* | 5 | 2-4 | 4 | 3.2 | 2-4 | 2 | 2.0 |
| *A. flavus* | 5 | 2-16 | 2 | 4.8 | 2-16 | 2 | 4.8 |
| *A. versicolor* | 5 | 0.25-2 | 1 | 0.9 | 0.25-2 | 1 | 0.9 |
| *Alternaria* spp. | 5 | 0.06-0.5 | 0.25 | 0.262 | 0.25-0.5 | 0.25 | 0.25 |
| *Cladosporium* spp. | 5 | 0.5-2 | 1 | 0.9 | 0.25-0.5 | 0.25 | 0.7 |
| *Scopulariopsis* spp. | 5 | 0.5-1 | 1 | 0.95 | 0.5-1 | 1 | 0.95 |
| *Acremonium* spp. | 5 | 4-8 | 8 | 7.2 | 8 | 8 | 8 |
| *Paecilomyces* spp. | 5 | 1-2 | 1 | 1.6 | 0.5-2 | 1 | 1.4 |
| *E. jeanselmei* | 3 | 2-8 | 4 | 4.67 | 2-8 | 4 | 4.67 |
| *Emmonsia parvum* | 2 | 0.25 | 0.25 | 0.25 | 0.25 | 0.25 | 0.25 |
| *Epioccum* spp. (*Chrysporium parvum*) | 2 | 1 | 1 | 1 | 1 | 1 | 1 |

Activity Against Endemic Fungal Pathogens

Current therapy for endemic pathogens is either slowly cidal in vivo or has toxicity problems, and alternatives are needed. The broth macrodilution and the CLSI-recommended MIC (minimal inhibitory concentration) methods were used in this study against 14 clinical isolates: *Coccidioides* (C) (5 isolates), *Blastomyces* (2), *Histoplasma capsulatum* (H) (5) and *Paracoccidioides* (P) (2). The MFC (minimal fungicidal concentration) endpoint was >96% kill of the inoculum.

As demonstrated in Table 4, corifungin's MICs ranged narrowly from 0.5 (the 2 P) to 2 mcg/mL in 14/14 cases. Amphotericin B's MICs ranged from 0.5 (for 4 of the H) to 4 (for 3 of the C) mcg/mL. Corifungin's MFCs equaled MICs in 14/14 cases. Amphotericin B MFCs ranged from 0.5 (for 4 of the H) to ≥8 (for 3 of the C), and equaled amphotericin B MICs in 11/14 cases, with 3 C having amphotericin B MFCs 1 to ≤3 dilutions higher than amphotericin B MIC. Corifungin's MICs were ≤2 twofold dilutions different from amphotericin B in all 14 tests, with 5 corifungin<amphotericin B (3 of these C, 2 P), 5 corifungin>amphotericin B (4 of these H), and 4 same. Corifungin's MFCs were ≤2 dilutions different from amphotericin B in 12/14 tests, with 2 C isolates having amphotericin B MFCs ≥4-fold higher than corifungin.

TABLE 4

In vitro susceptibility assays comparing corifungin to amphotericin B against endemic fungal pathogens.

| Isolate # | corifungin MIC/MFC | Amphotericin B MIC/MFC |
|---|---|---|
| *Coccidioides* sp | | |
| 1 | 2/2 | 2/8 |
| 2 | 1/1 | 4/8 |
| 3 | 2/2 | 1/>8 |
| 4 | 2/2 | 4/4 |
| 5 | 1/1 | 4/4 |
| *Blastomyces dermatitidis*: | | |
| 1 | 16/16 | 2/2 |
| 2 | 8/8 | 1/1 |

Time Kill Assays (TKA)

Figure 13:
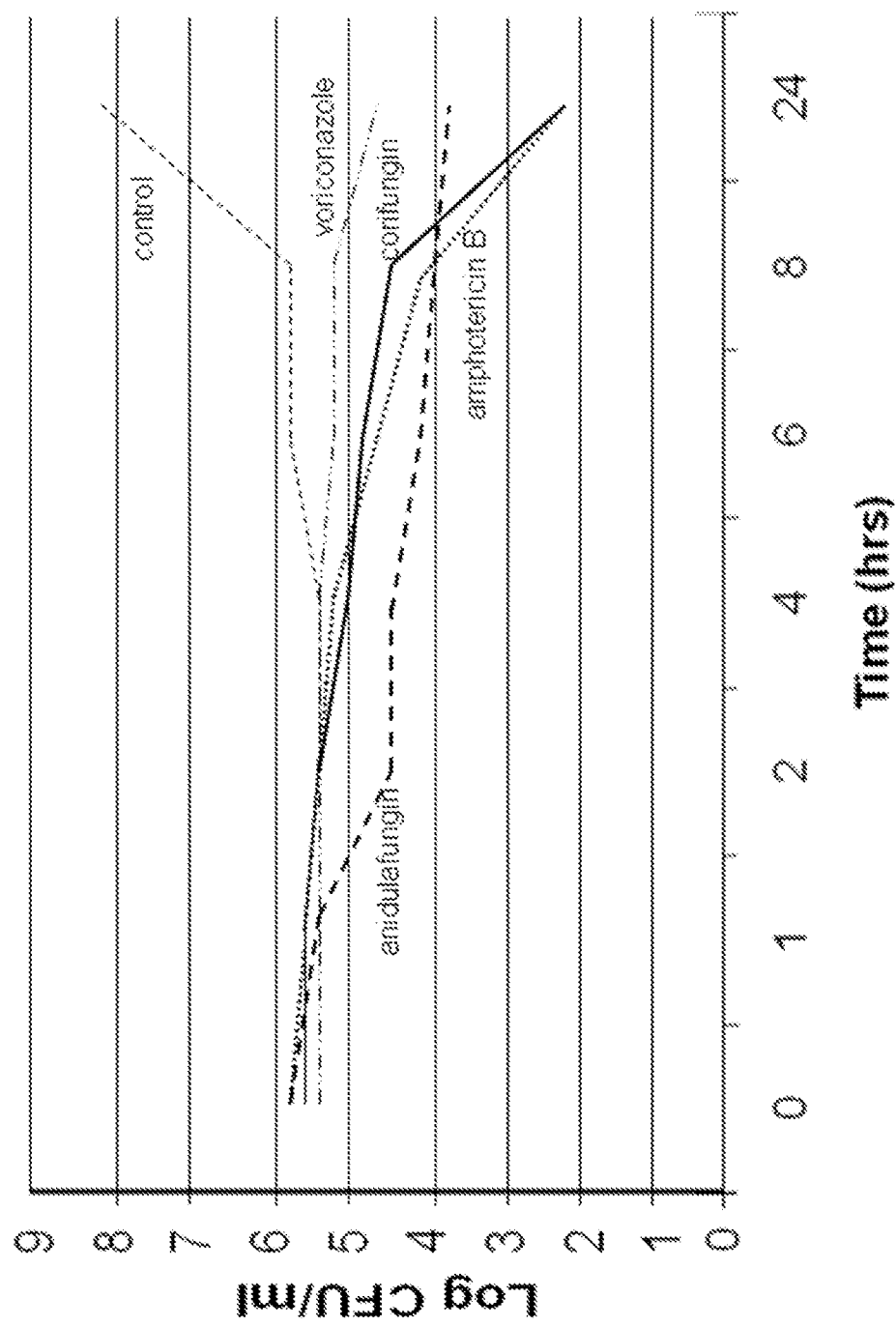
FIG. 13 shows the time kill profiles of corifungin against *C. parapsilosis* compared to anidulafungin, voriconazole, and amphotericin B.
Figure 14:
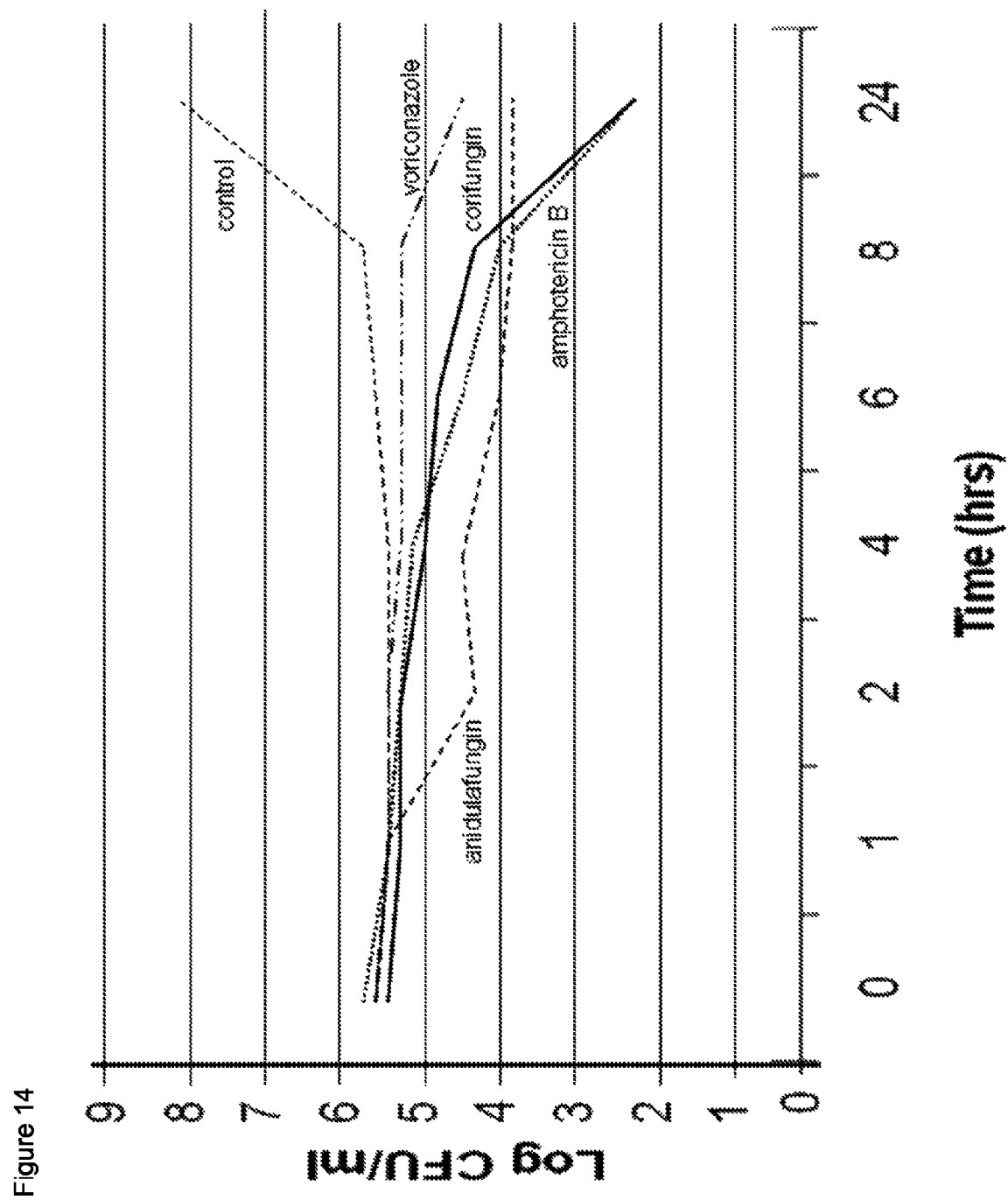
FIG. 14 shows the time kill profiles of corifungin against *C. glabrata* compared to anidulafungin, voriconazole, and amphotericin B.
Figure 15:
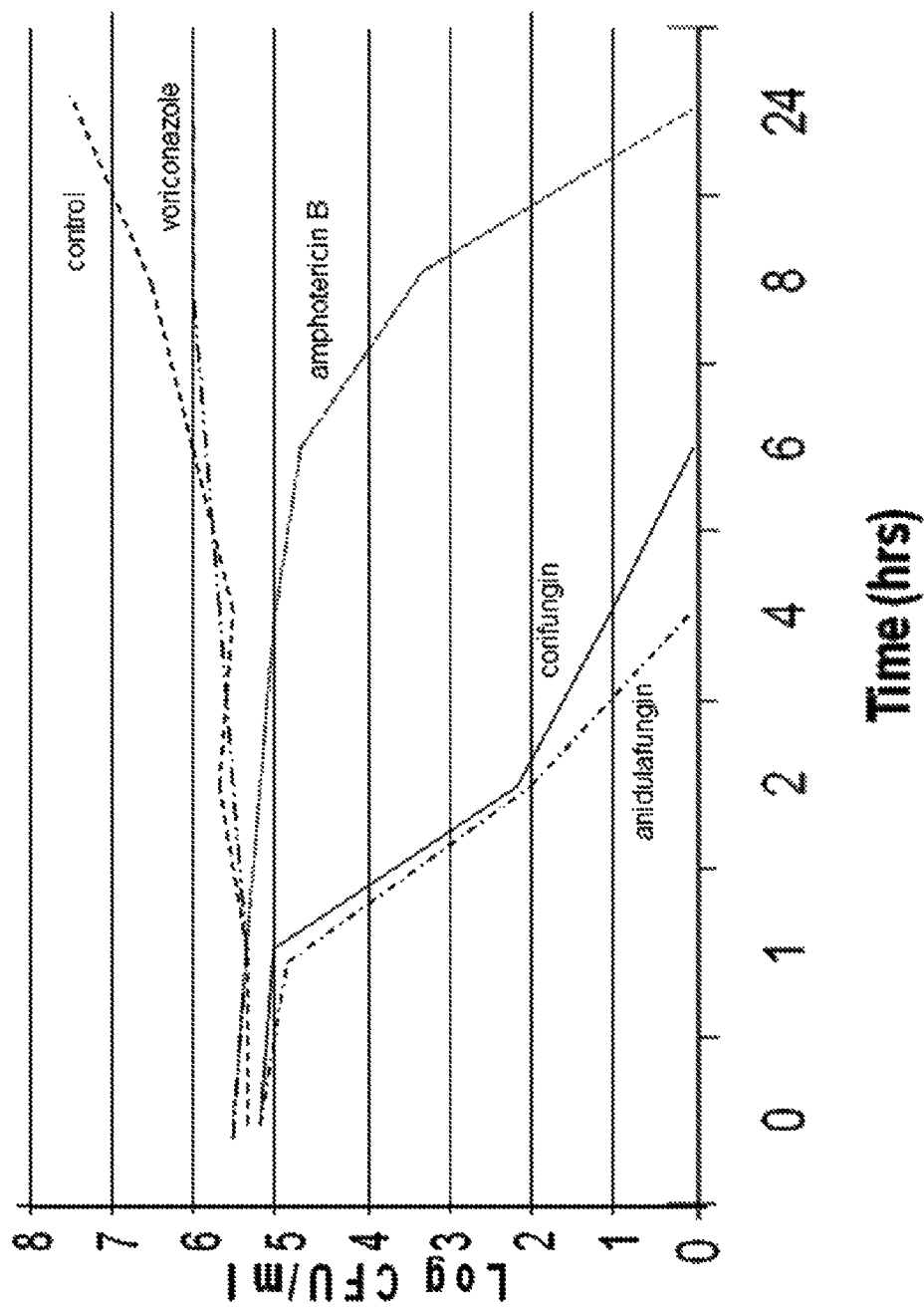
FIG. 15 shows the time kill profiles of corifungin against *C. albicans* compared to anidulafungin, voriconazole, and amphotericin B.

The activity profiles of corifungin other antifungal drugs using the time kill assay (TKA). FIGS. 13, 14, and 15 demonstrate the substantial fungicidal activity of corifungin compared to both amphotericin B and also to anidulafungin against the three most commonly isolated *Candida* spp.

EXAMPLE 4

In Vivo Antifungal Activity

Activity Against *Candida* in Immunocompetent Mice
Methodology

Male CD-1 (Crl.) mice weighing 24±2 g were maintained in a controlled temperature (22° C.-24° C.) and humidity (60%-70%) environment with 12 hours light dark cycles for at least one week. Free access to standard lab chow for mice (MF-18, Oriental Yeast Co., Ltd. Japan) and RO water and conduct of study was in accordance with the Guide for the Care and Use of Laboratory Animals (National Academy Press, Washington, D.C., 1996).

Mice were inoculated intravenously (IV) with an LD90-100 of *Candida albicans* (ATCC 44858), 5.2×105 CFU/mouse in 0.2 mL of phosphate-buffered saline (PBS, pH 7.4) without mucin. Corifungin at 0.5, 5.0 and 50 mg/kg and vehicle control were each administered orally (PO) to test animals one hour after the fungal inoculation. The positive reference agent of amphotericin B (3 mg/kg) was administered (PO). The dosing volume was 10 mL/kg.

Corifungin, amphotericin B, and the vehicle control (distilled water) were administered orally to test animals one hour after fungal inoculation. Mortality was monitored once daily for 15 days.

Results

Figure 16:
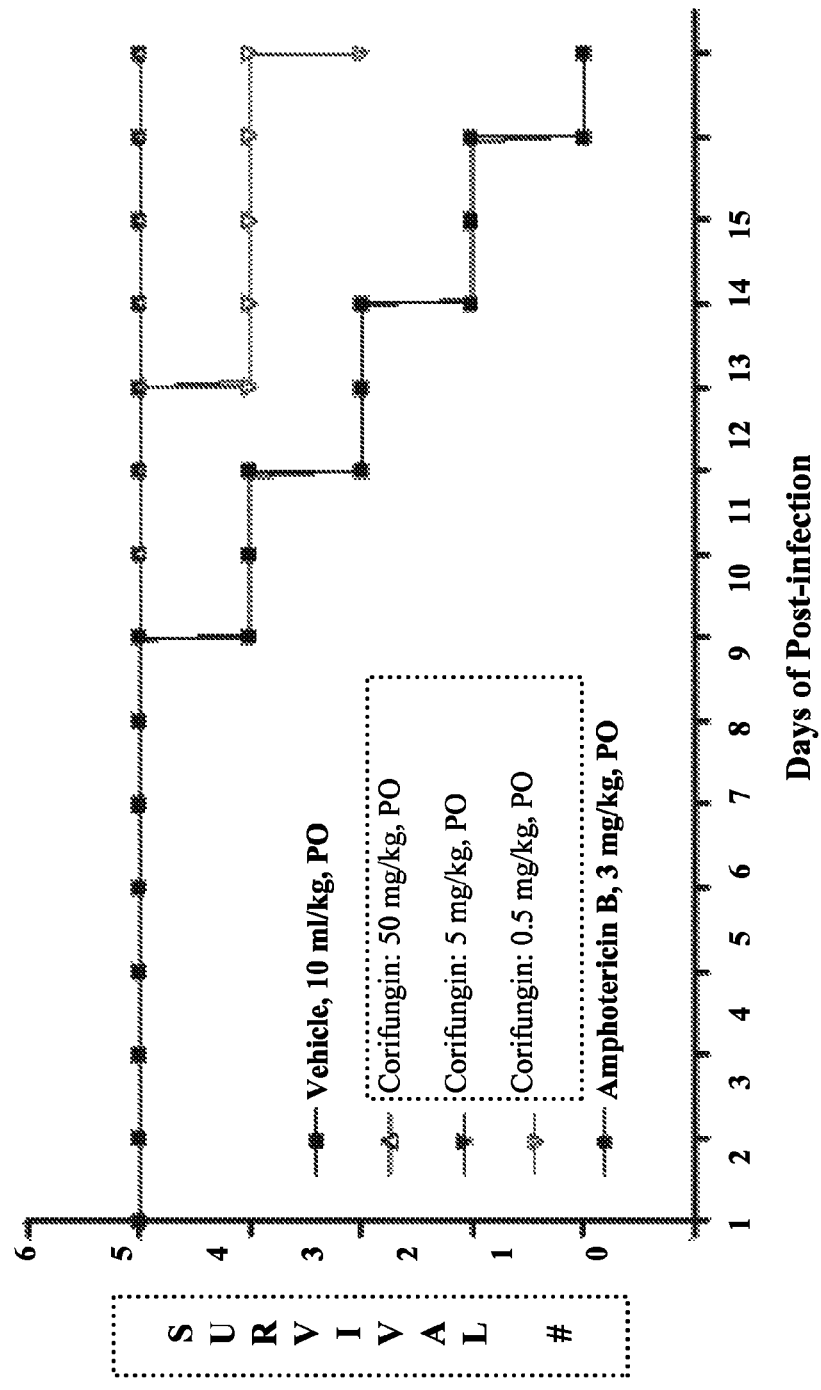
FIG. 16 shows the effect of corifungin on survival in mice infected with *C. albicans*. The mice were inoculated intravenously (IV) with an LD90-100 of *Candida albicans* (ATCC 44858), $5.2 \times 10^5$ CFU/mouse in 0.2 mL of phosphate-buffered saline (PBS, pH 7.4) without mucin. Corifungin was administered orally to test animals 1 hour after the fungal inoculation. Mortality was monitored once daily for 15 days.

As demonstrated in FIG. 16, significant protection (>50% increase of survival rate) was observed for corifungin at doses of 5.0 and 50.0 mg/kg (80% increase in survival) relative to the vehicle control group (0%) during the 15-day observation period Minimum effective dose is in the 0.5-1.0 mg/kg range. The positive control, amphotericin B at 3 mg/kg, PO exhibited 80% increase in survival rate.

Activity Against Vaginal Infections in Mice
Methodology

Female C3H (instead of CBA/J) mice, 8-10 weeks old and weighing 20 g obtained from National Institutes of Health (NCI, Frederick, Md.) were first injected subcutaneously (under manual restraining) with 1.0 mg estradiol valerate dissolved in sesame oil 72 h prior to vaginal inoculation. A condition of pseudoestrus was required to obtain a persistent vaginal infection in rodents. Weekly injections satisfy this requirement. Hence for these experiments, estrogen was given on days −2 with inoculation on day 0. For vaginal inoculation, animals were anesthetized "to effect" by isofluorane inhalation. To anesthetized animals, $5 \times 10^5$ C. albicans blastospores in 20 μL PBS was introduced into the vagina, using a pipetman. Corifungin treatments given by oral gavage (5 and 50 mg/kg in 250 μL water and 50 mg/kg in 250 μL PBS pH 7.5) began on day 2 post-inoculation and continued once daily through day 4. Corifungin was dissolved in water then diluted with PBS. Corifungin treatment given by intraperitoneal (IP) injection was 50 mg/kg in 500 μL water. Positive controls for the infection and negative controls for the drug included vehicle (water/PBS)-treated infected animals. On day 5, separate groups of 6 animals were sacrificed by cervical dislocation and the vaginas lavaged with 100 μL of phosphate buffered saline (PBS). The lavage fluid was subsequently cultured for enumeration of organisms. The lavage fluid is diluted serially using 1:10 dilutions (10 μL into 90 μL PBS). From each dilution tube, 10 μL is added to a Sabouraud/50 μ/mL chloramphenicol agar plate and spread with a sterile spreader. The plates are incubated at 30° C. for 48-72 h. The numbers of yeast colonies are counted on the plates and expressed as colony forming units (CFU).

Results

Figure 17:
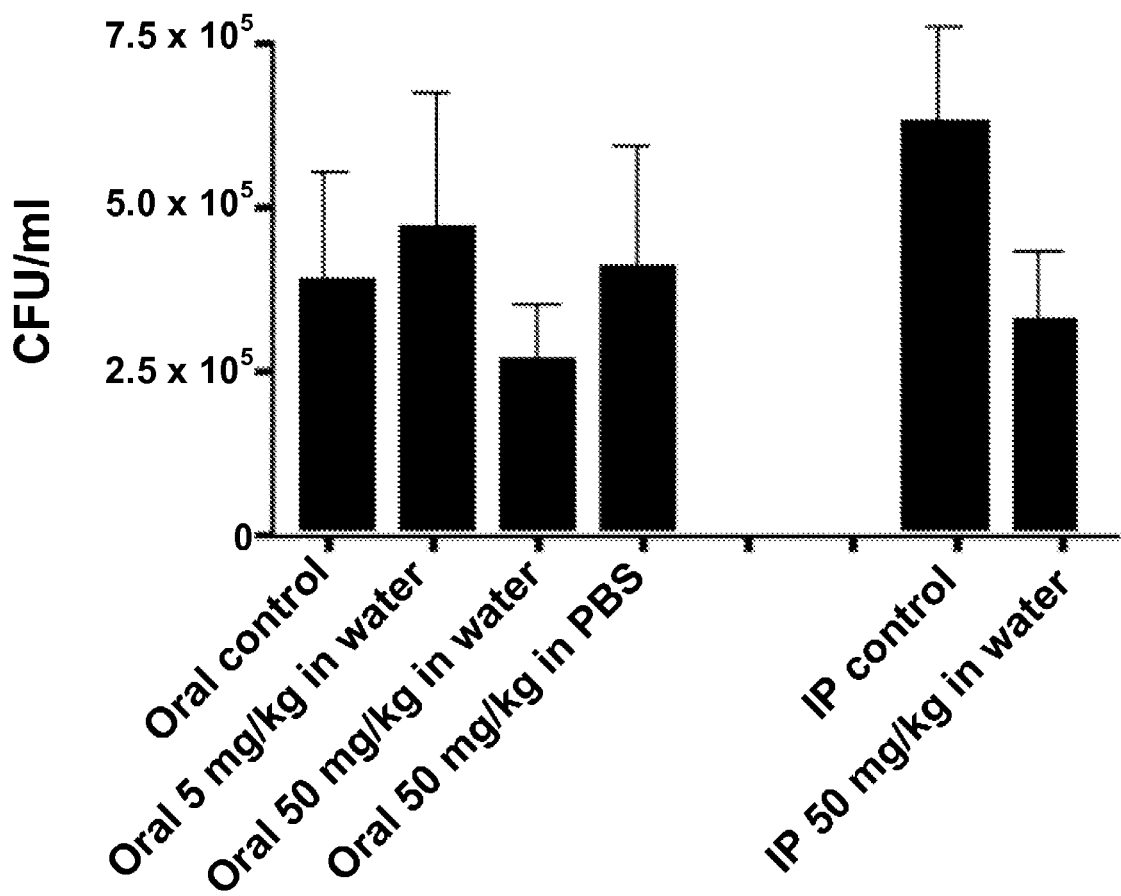
FIG. 17 shows that corifungin effectively reduced vaginal infection by *C. albicans* at 50 mg/kg dose.

As demonstrated in FIG. 17, corifungin dissolved in water and administered orally by gavage or intraperitoneally was active against *Candida albicans* DB597.94 at 50-mg/kg dosage.

Activity Against Fungal Infections in Neutropenic Mice
Methodology

Six-week-old ICR/Swiss specific-pathogen-free female mice weighing 23 to 27 g were used for all studies (Harlan Sprague Dawley, Madison, Wis.). All animal studies were approved by the Animal Research Committee of the William S. Middleton Memorial VA Hospital. Mice were rendered neutropenic (<100 polymorphonuclear leukocytes per $mm^3$) by injection with cyclophosphamide (Mead Johnson Pharmaceuticals, Evansville, Ind.) intraperitoneally 4 days (150 mg/kg of body weight) and 1 day (100 mg/kg) before infection.

Neutropenic mice were infected with a clinical isolate of *Candida* by injection of 0.1 mL of inoculum via the lateral tail vein 2 h prior to the start of drug therapy. Two hours after infection, mice were treated with single oral gavage doses of corifungin (2-, 10-, 50-, and 250-mg/kg) administered in 0.2-mL volumes. At the end of the study period, animals were sacrificed by $CO_2$ asphyxiation. After sacrifice, the kidneys of each mouse were immediately removed and placed in sterile 0.9% saline at 4° C. The homogenate was then serially diluted 1:10, and aliquots were plated on Sabouraud dextrose agar (SDA) for viable fungal colony counts after incubation for 24 h at 35° C. The lower limit of detection was 100 CFU/mL. Results were expressed as the mean CFU per kidney for two mice (four kidneys).

Results

Figure 18:
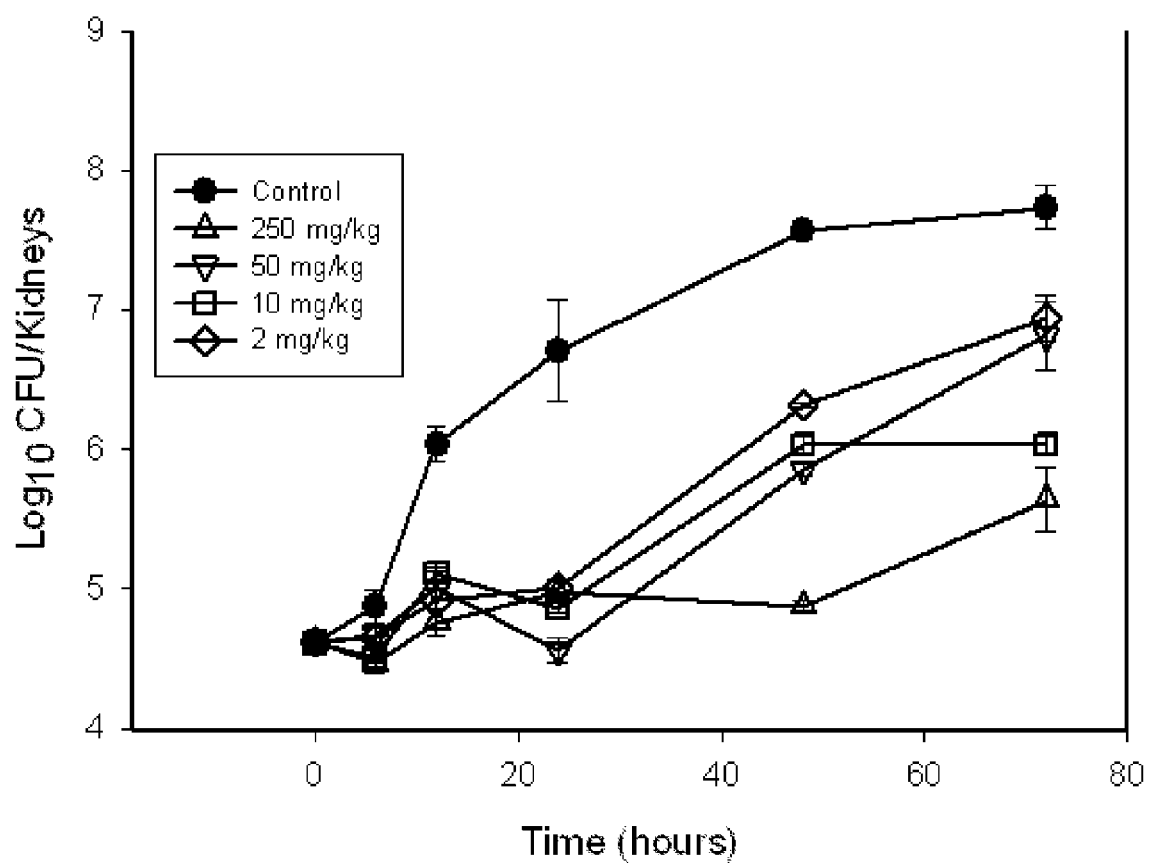
FIG. 18 shows the impact of a single oral administration of corifungin on the burden of *C. albicans* in the kidneys of neutropenic mice. Neutropenic mice were infected by tail vein 2 hours before drug administration. Single doses of corifungin were administered to mice by oral gavage. Organism burden in the kidney was utilized as the treatment endpoint over time. Groups of three mice were sampled at each time point. Each symbol represents the mean log10 cfu/kidneys from three mice and the error bars represent the standard deviation. The solid symbols represent organism burden in untreated control mice. Each dose of corifungin inhibited organism growth in the kidneys for the first 24 hours of study. The highest dose provided similar protection for 48 h and demonstrated some effectiveness at 96 h. At the 48 and 96 hour time points a dose response relationship was observed. The effectiveness over time suggests slow, saturable, but persistent absorption from the gastrointestinal track.

Organism burden in the kidney was utilized as the treatment endpoint over time. Groups of three mice were sampled at each time point. The results of this study are shown in FIG. 18. Each symbol represents the mean log10 cfu/kidneys from three mice and the error bars represent the standard deviation.

As demonstrated in FIG. 18, corifungin was very effective in reducing the *C. albicans* burden in the kidneys of neutropenic mice. Each dose of corifungin inhibited organism growth in the kidneys for the first 24 hours of study. The highest dose provided similar protection for 48 h and demonstrated some effectiveness at 96 h.

Serum samples were obtained from three mice at each of the time points for which kidney burden was assessed. A previously described microbiologic assay was used to measure corifungin concentrations. The initial assay exhibited very poor sensitivity and did not detect measurable corifungin concentrations. Assay troubleshooting improved assay sensitivity to values near the original (0.5 μg/mL) assay. Repeat run of the samples detected concentrations at the limit of detection for the highest dose level (250 mg/kg) at 12 h. Corifungin demonstrated static activity for each of the 4 dose levels for prolonged periods of time. The period of growth suppression was dose dependent suggestion saturable but continued gastrointestinal absorption. The corifungin microbiologic assay was not sensitive enough to characterize the pharmacokinetics.

EXAMPLE 5

Toxicology, Histopathology, and Pharmacokinetic (PK) of Corifungin

Toxicology
Methodology

Jugular vein cannulated (JVC) SD rats, following a 7-12 day acclimation period, were weighed and randomized into 7 experimental groups of 4 animals. Corifungin was administered daily to study rats by oral gavage for 28 days at three doses of 0.5, 50, and 250mg/kg and amphotericin B was administered intravenously three days a week at a dose of 0.5, 1.0 or 1.5mg/kg. Throughout the study, animals were observed daily Animals were weighed once a week and on the day of termination. On day 30 of the study, animals were dosed the final time and then plasma samples were collected from each animal at 15 minutes and 1, 2, 6, 24, 48 and 72 hours post dosing for terminal pharmacokinetic analysis of amphotericin B or corifungin. Animals were terminated on study day 33. Animals were fasted overnight and placed into metabolic cages for urine collection. Prior to termination, blood (0.5-1.0 mL) was collected by cardiac puncture or orbital bleed for hematology and clinical chemistry analysis. Animals were terminated by carbon dioxide asphyxiation. Hematology and a panel of clinical chemistry were conducted on all collected blood and serum samples. In addition a urinalysis panel was performed on all collected urine samples.

Clinical Chemistry Results

Table 5 summarizes the results of the clinical chemistry study. Corifungin was well tolerated in animals. At 250 mg/kg, the clinical chemistry values are within normal range. Corifungin was tolerated in animals up to a level of 250 mg/kg when administered by oral gavage for 28 days. The no adverse effect level (NOAEL) for corifungin from this study is determined to be 250 mg/kg. No toxicity was observed in rats when administered amphotericin-B intravenously at 1.5 mg/kg three times a week over 28 days.

TABLE 5

Clinical Chemistry values of rat sera orally dosed daily for 28 days with corifungin up to 250 mg/kg versus control and treatment with amphotericin B.

| Treatment dose | Na | K | Cl | Mg | BUN | Creat | ALT | ALK | TP | ALB | GLOB | A/G |
|---|---|---|---|---|---|---|---|---|---|---|---|---|
| Corifungin | | | | | | | | | | | | |
| 0.5 mg | 139 | 4.8 | 98 | 1.5 | 13 | 0.5 | 35 | 82 | 60 | 3.4 | 2.6 | 1.3 |
| 50.0 mg | 140 | 4.6 | 99 | 1.8 | 16 | 0.6 | 34 | 61 | 60 | 3.3 | 2.7 | 1.3 |
| 250.0 mg | 142 | 6.3 | 97 | 2.1 | 26 | 0.8 | 43 | 121 | 57 | 2.9 | 2.8 | 1.1 |
| Control | | | | | | | | | | | | |
| (H$_2$O) | 140 | 5.0 | 101 | 1.5 | 16 | 0.6 | 33 | 101 | 57 | 3.3 | 2.4 | 1.4 |
| Amphotericin B | | | | | | | | | | | | |
| 0.5 mg | 140 | 4.7 | 103 | 1.7 | 15 | 0.6 | 37 | 74 | 59 | 3.2 | 2.6 | 1.2 |
| 1.0 mg | 140 | 5.1 | 102 | 1.7 | 16 | 0.6 | 37 | 61 | 6.0 | 3.2 | 2.7 | 1.3 |
| 1.5 mg | 132 | 4.8 | 93 | 1.5 | 17 | 0.6 | 36 | 69 | 65 | 3.4 | 2.4 | 1.4 |

Electrolytes: Na$^+$ = Sodium; K$^+$ = Potassium; Cl$^-$ = Chloride; Mg$^{2+}$ = magnesium
Kidney marker: BUN = Blood Urea Nitrogen; Creat = Creatinine
Liver marker: ALT = Alanine Aminotransferase; ALK = Alkaline Phosphatase
Misc: TP = Total Protein; ALB = Albumin; GLOB = Globulin; A/G = Albumin/Globulin ratio Histopathology
Methodology Corifungin was administered daily to rats by oral gavage for 28 days at three doses of 0.5, 50, and 250 mg/kg. Animals were terminated on study day 33. A complete gross necropsy was performed after termination and the following tissues were collected and fixed in 10% formalin for histopathological analysis: lung and trachea, liver, spleen, esophagus, stomach, intestine, and submandibular lymph nodes/salivary gland. H & E histologic slides were prepared containing the tissues and examined by light microscopy.

Results

There were no test-article related histomorphologic findings. There was no evidence of infectious, toxic, developmental or neoplastic change or transformation occurring in any of the tissue sections evaluated.

Pharmacokinetic Profile
Methodology

Female jugular vein cannulated SD rats, following a minimum of 7 day acclimation period, were weighed and randomized into experimental groups consisting of 3 animals each. Groups 1, 2 and 3 received corifungin doses via oral gavage of 0.5 mg/kg, 50.0 mg/kg and 250 mg/kg respectively. Groups 4, 5 and 6 received corifungin doses via intravenous (IV) of 0.5 mg/kg, 1.0 mg/kg and 5 mg/kg respectively. Groups 7, 8 and 9 received amphotericin B doses of 0.5 mg/kg, 1.0 mg/kg and 1.5 mg/kg respectively. Corifungin dosing solutions were prepared directly in sterile water for oral gavage; corifungin IV dosing solutions were prepared directly in 5% dextrose. Amphotericin B-deoxycholate was prepared according to the manufacturer's directions (e.g., resuspended in 10 mL of water and further diluted into 5% dextrose). IV administration was performed via the jugular vein cannula.

Blood samples (~200-300 μL) were collected from all animals in Groups 1-9 at 15 min, 1 hr, 2 hr, 6 hr, 24 hr, 48 hr, 72 hr and 96 hr post dose administration. At least 200 μL of blood was withdrawn by pulling back on the syringe barrel; blood was collected directly from the tail vein into heparin tubes. The S-Monovet tube/syringe containing the collected blood sample was inverted to mix the blood with the anti-coagulant immediately upon collection and then placed on ice. The S-Monovet tubes were then spun to separate the plasma, and the plasma samples were transferred into new labeled 1.5 mL microfuge tubes and stored at −80° C. until ready for analysis.

Results

Figure 19:
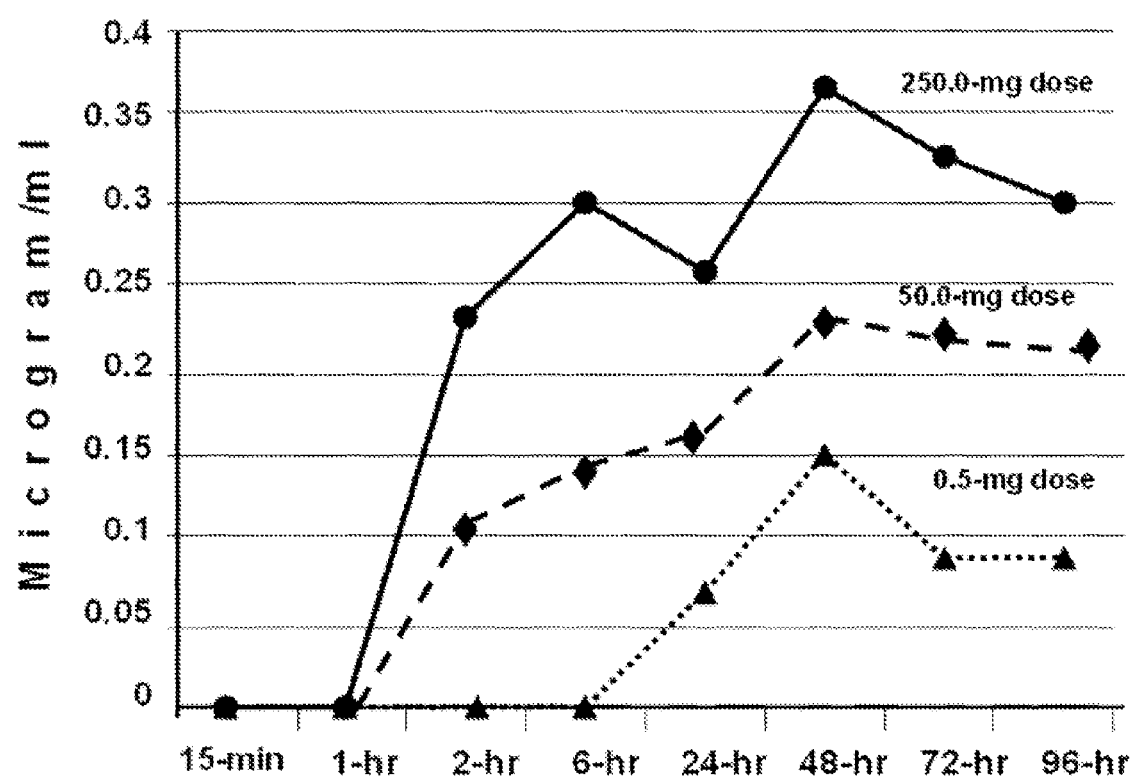
FIG. 19 shows the pharmacokinetic profile of corifungin administered per oral (PO) by gavage.
Figure 20:
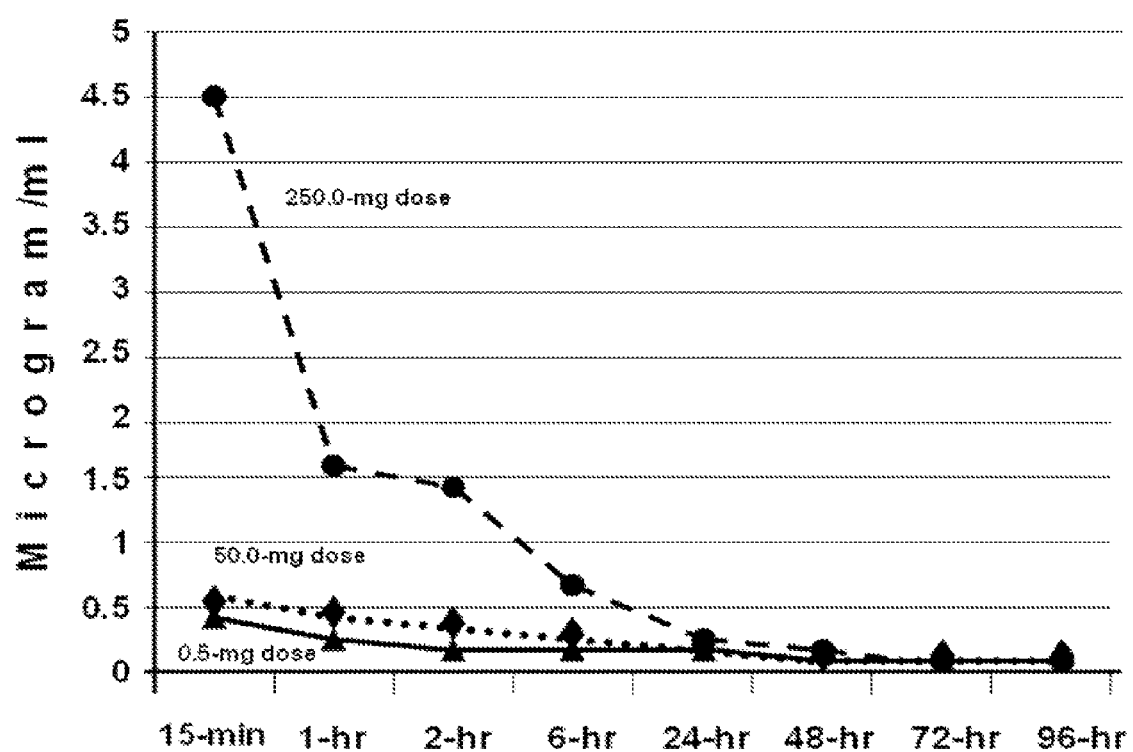
FIG. 20 shows the pharmacokinetic profile of corifungin administered by intravenous injection (IV).

Corifungin level in plasma samples were determined by microbiological assay. Thus, a standard antibiotic activity curve is established for corifungin and antifungal activity found in the sample plasma is plotted against the curve to determine antibiotic concentration. The results of this study are shown in FIG. 19 (PO administration) and FIG. 20 (IV administration). Corifungin administered PO is absorbed through the intestinal mucosa and lingers in the blood stream even after 4 days (96 hours): 0.5 mg/kg-dose peaks at 48 hours, while 50 mg/kg-dose peaks at 6 hours (see FIG. 19). On the other hand, corifungin administered IV showed a steady-state distribution profile with peak concentration just after injection (15-min) and gradually tapers off, but still detectable after 4 days (see FIG. 20).

EXAMPLE 6

Treatment of Primary Amoebic Meningoencephalitis Using Corifungin

Methodology

Ten animals (each at an age of one month) per group were used for an in vivo study investigating the treatment of primary amoebic meningoencephalitis using corifungin. The Balb/c mice were infected with 2×10$^4$/20 μL trophozoites of *Naegleria fowleri*. Infected mice were treated with one of (i) a control (PBS), (ii) amphotericin B (9 mg/kg/day for a total of 10 days), or (iii) corifungin (9 mg/kg/day for a total of 10 days). The mice were necropsied 17 days after infection. Representative brain samples were fixed in 4% paraformaldehyde/PBS, embedded, sectioned, and stained with H&E.

Results

Figure 21:
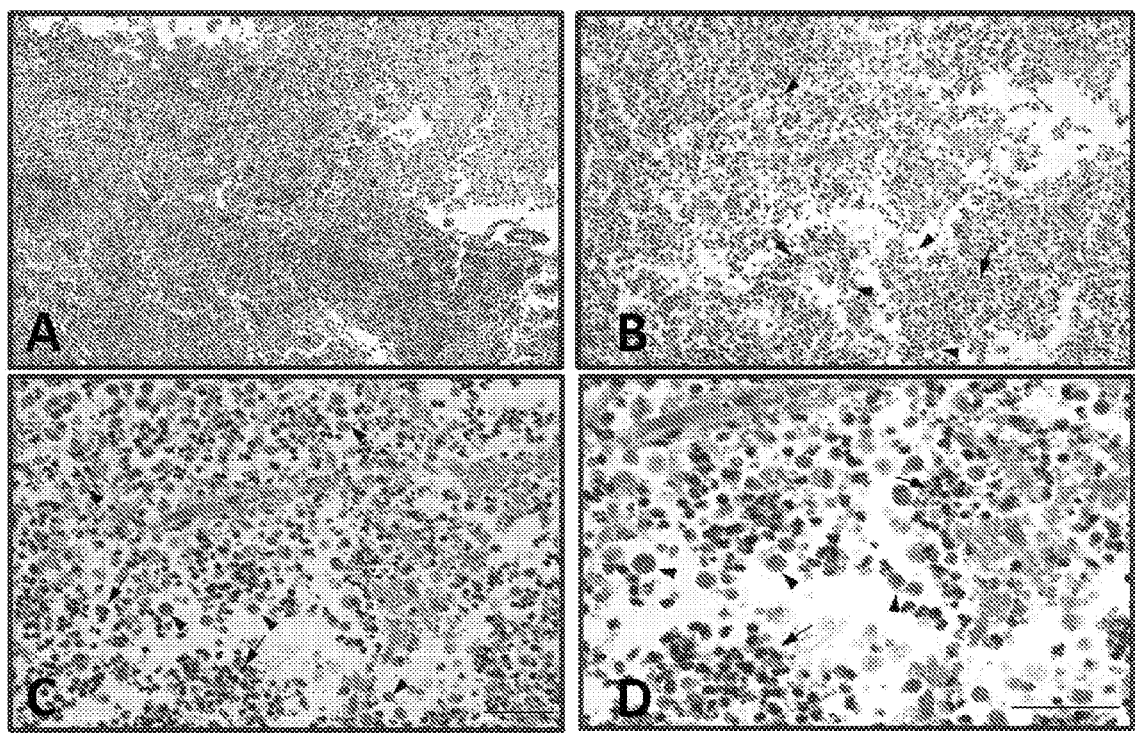
FIG. 21 shows the meningoencephalitis disease state at 11 days post-infection by *Naegleria fowleri* and following treatment with a PBS control. (A) 10×. (B) 20×. (C) 40×. (D) 60×.

Control Group. FIG. 21 shows the meningoencephalitis disease state at 11 days post-infection by *Naegleria fowleri* and following treatment with a PBS control. FIG. 21(A) depicts meningoencephalitis in Balb/c mouse as developed in the olfactory bulbs following infection with *Naegleria fowleri*. An inflammatory reaction composed mainly of neutrophils was observed. Tissue necrosis in the control group was widespread. FIG. 21(B) shows the same area and demonstrates that numerous trophozoites (arrow-heads) and inflammatory cells (arrows) were present in the tissue sample. FIGS. 21(C) and (D) show a higher magnification of the same area and demonstrates that amoebae (arrow-heads) and neutorphils (arrows) were present in the tissue sample.

Figure 22:
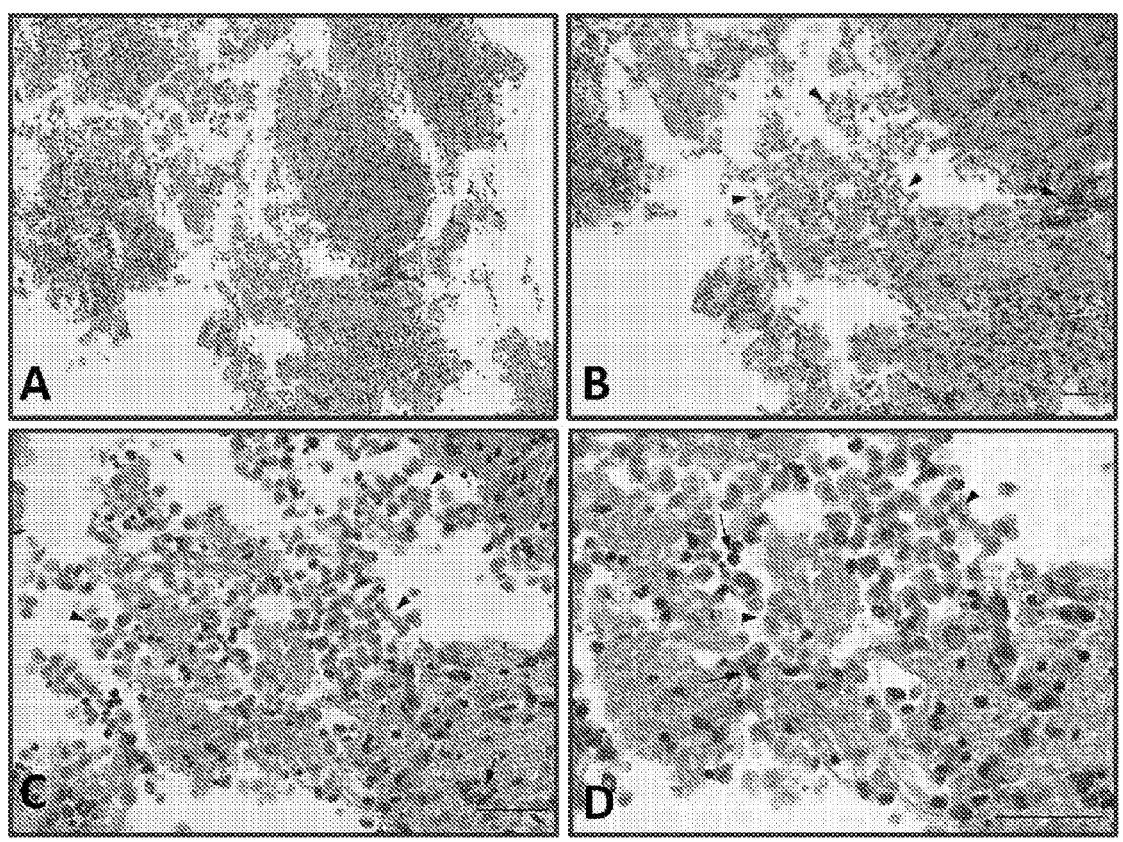
FIG. 22 shows the meningoencephalitis disease state following infection by *Naegleria fowleri* and subsequent treatment with amphotericin B (9 mg/kg/day for a total of 10 days). (A) 10×. (B) 20×. (C) 40×. (D) 60×.

Amphotericin B Group. FIG. 22 shows the meningoencephalitis disease state following infection by *Naegleria fowleri* and subsequent treatment with ampohotericin B (9 mg/kg/day for a total of 10 days). FIGS. 22(A) and (B) depict meningoencephalitis in Balb/c mouse as developed in the olfactory bulbs following infection with *Naegleria fowleri*. The olfactory bulbs showed several amoebae (arrow-heads) and inflammatory cells (arrows). FIGS. 22(C) and (D) show a higher magnification of the same area.

Figure 23:
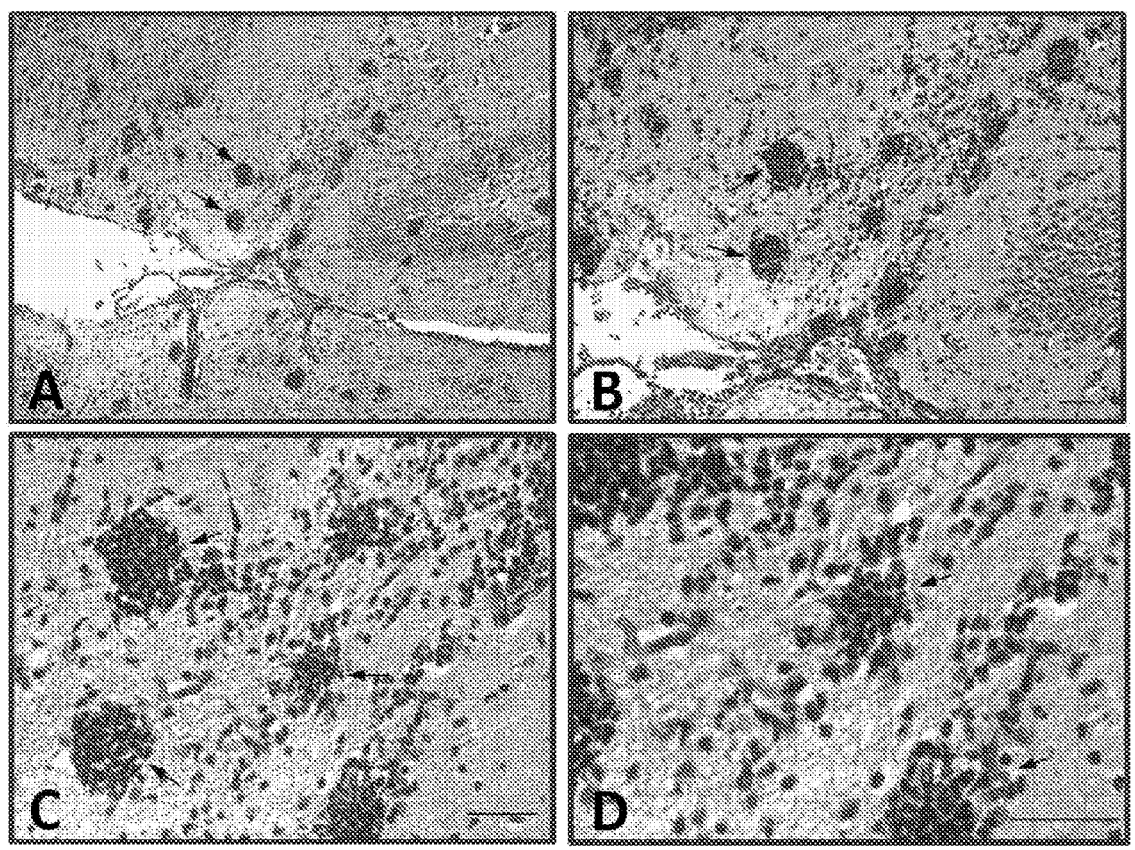
FIG. 23 shows the meningoencephalitis disease state following infection by *Naegleria fowleri* and subsequent treatment with corifungin (9 mg/kg/day for a total of 10 days). (A) 10×. (B) 20×. (C) 40×. (D) 60×.

Corifungin Group. FIG. 23 shows the meningoencephalitis disease state following infection by *Naegleria fowleri* and subsequent treatment with corifungin (9 mg/kg/day for a total of 10 days). FIGS. 23(A) and (B) depict meningoencephalitis in Balb/c mouse as developed in the olfactory bulbs following infection with *Naegleria fowleri*. The olfactory bulbs showed multiple inflammatory foci without trophozoites (arrows). FIGS. 23 (C) and (D) show a higher magnification of the same area.

Figure 24:
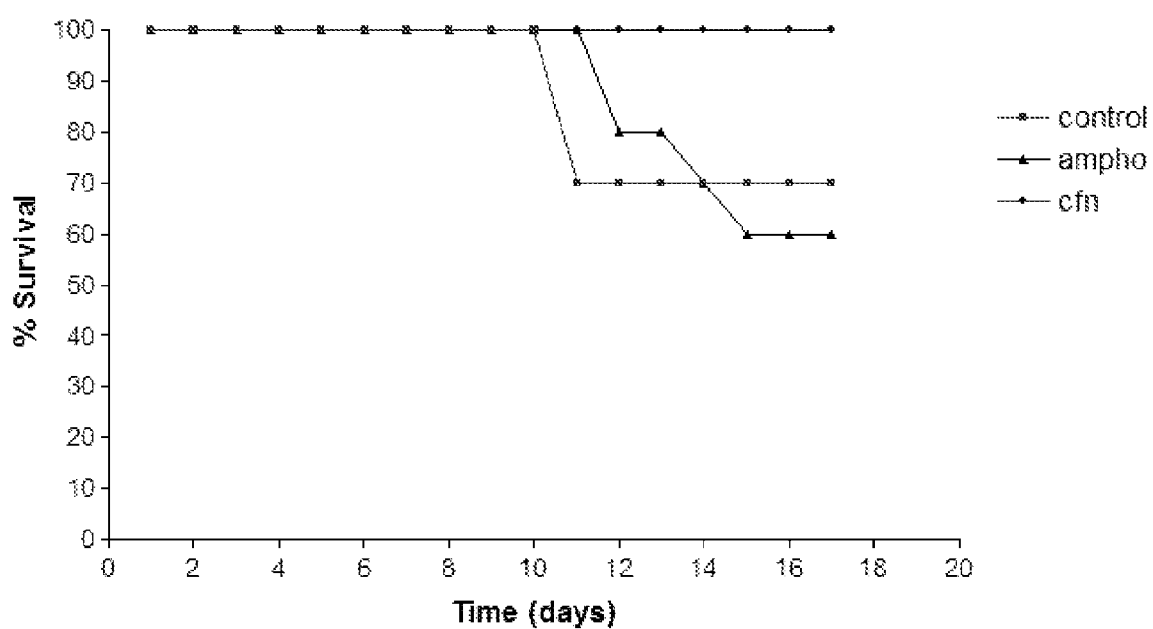
FIG. 24 shows the percentage of animals surviving as a function of time following treatement by (i) a control, (ii) amphotericin B, and (iii) corifungin.

The rate of survival was compared following *Naegleria fowleri* infection and subsequent treatment with (i) a control, (ii) amphotericin B (9 mg/kg/day for a total of 10 days), and (iii) corifungin (9 mg/kg/day for a total of 10 days). FIG. 24 shows the percentage of animals surviving as a function of time following treatement by (i) a PBS control, (ii) amphotericin B, and (iii) corifungin. As shown in FIG. 24, amphotericin B gave no improvement in survival over the control. Surprisingly, no deaths were observed for corifungin-treated animals.

EXAMPLE 7

Treatment of Visceral Leishmaniasis Using Corifungin

In Vitro Analysis
Methodology

FIG. 19 demonstrates the favorable pharmacokinetic distribution for corifungin. Corifungin was well tolerated in animals with minimal toxicity. As demonstrated in Table 5, the clinical chemistry values for corifungin are within normal range at 250 mg/kg. Corifungin was tolerated in animals up to a level of 250 mg/kg when administered by oral gavage for 28 days. The no adverse effect level (NOAEL) for corifungin from this study is determined to be >250mg/kg.

Since corifungin belongs to the same class of antibiotics as the very potent anti-leishmanial amphotericin B, its activity was tested against *Leishmania donovani* (i.e., one of the agents known to cause visceral leishmaniasis). A high-content assay was developed allowing screening for the activity of compounds against the human-infective, intracellular amastigote stage of *Leishmania*. The advantage of this technique is that the activity of compounds is directly assessed against the stage of the parasite relevant for human infection. Moreover it gives a primary indication of compound toxicity towards human cells.

Figure 25:
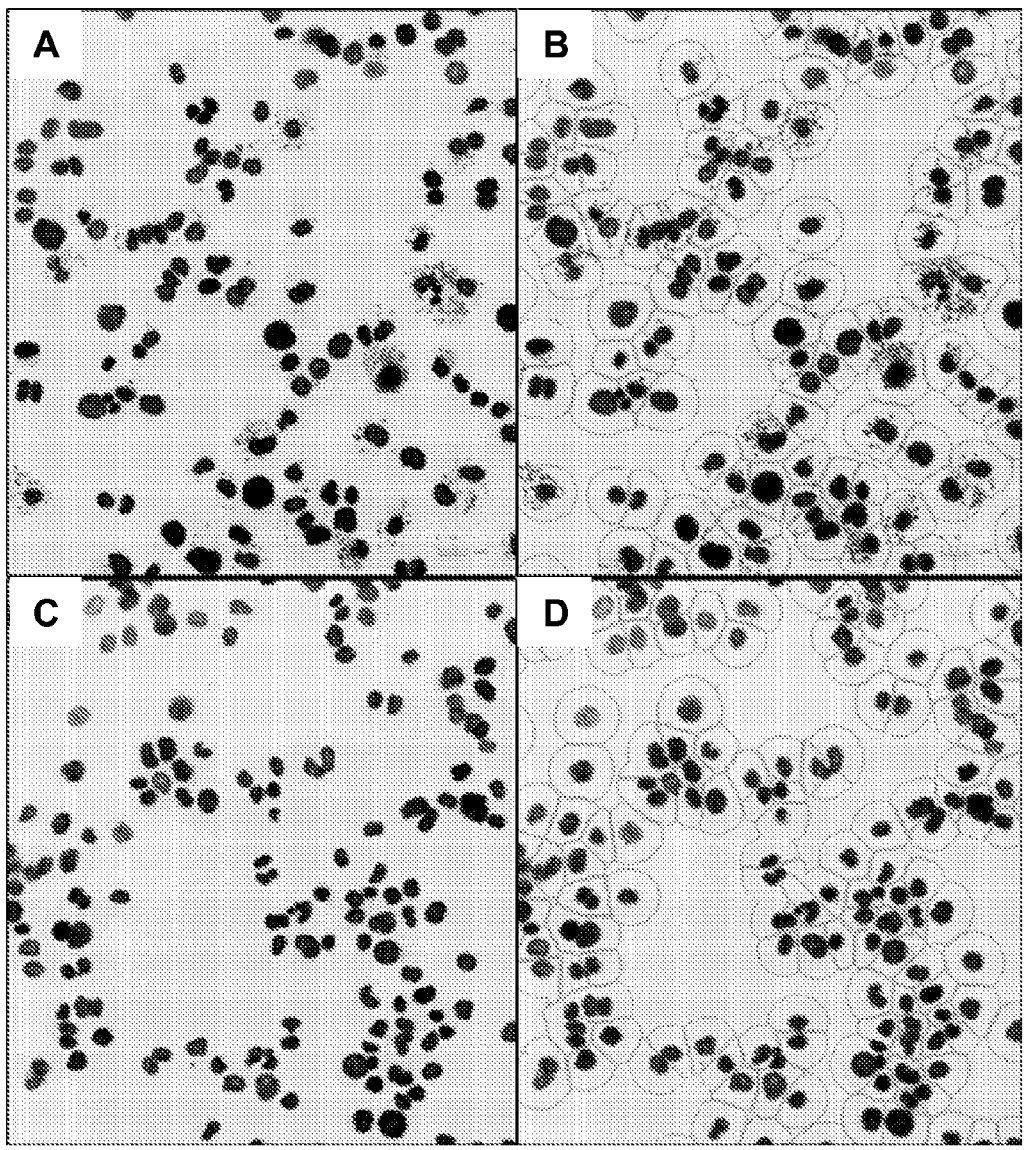
FIG. 25 shows infection of THP-1 cells with *L. donovani*. (A), (B), (C), and (D) depict the detection and segmentation of the THP-1 host cell and *L. donovani* intracellular amastigotes. The images were obtained with the INCell Analyzer 1000 (20×) of THP-1 cells infected with *L. donovani* and treated with 1% DMSO ((A) and (B)) or 2 µM amphotericin B ((C) and (D)). (E) Depicts the evolution of the ratio of parasites to host cells and the number of THP-1 host cells in a 72-hour time course for amphotericin B-treated samples.
Figure 25:
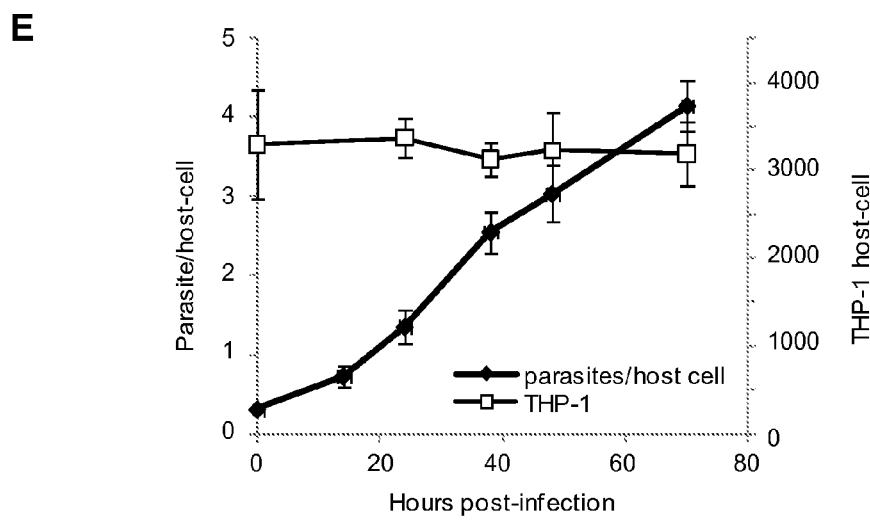
Figure 26:
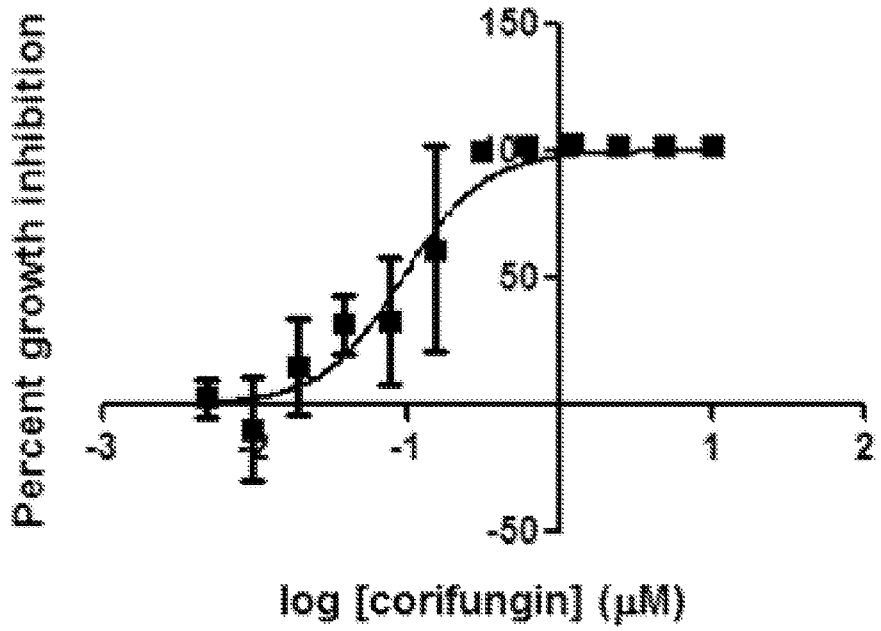
FIG. 26 shows the effect of corifungin on *L. donovani* intracellular growth and THP-1 host cell growth. (A) Shows a dose response curve for corifungin plotting the percentage of parasite growth inhibition. Values represent the mean for two independent experiments. (B) Shows the number of THP-1 macrophages infected with *L. donovani* for various treatment conditions.
Figure 26:
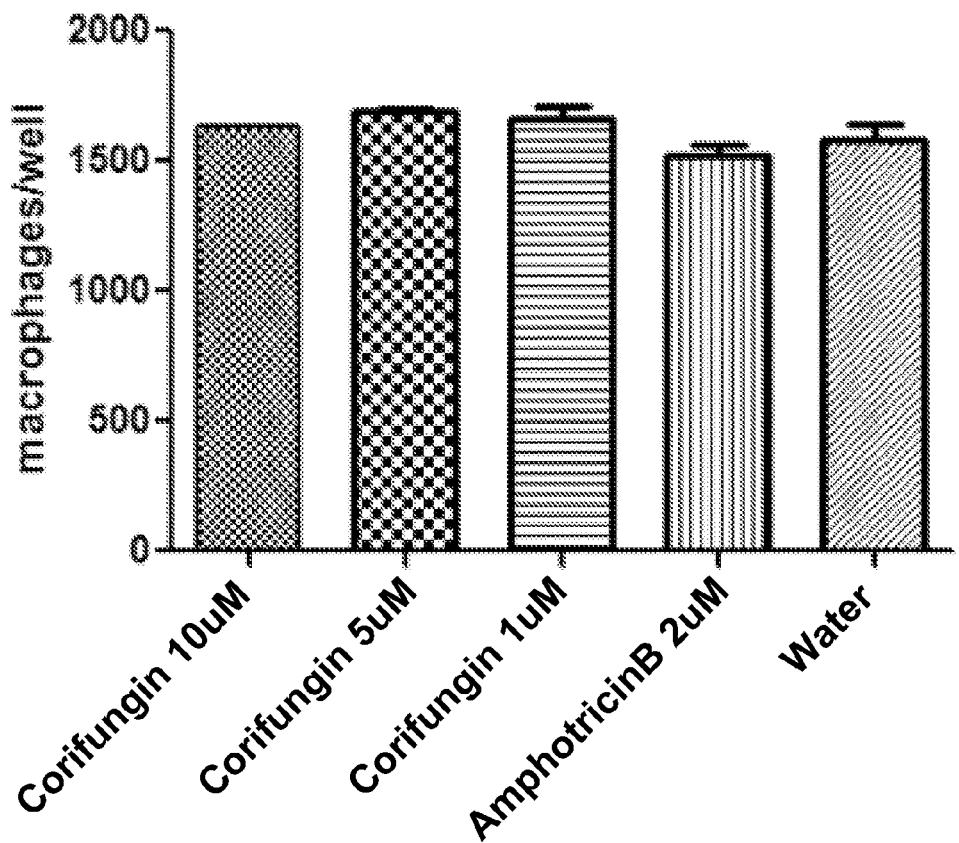

This cell-based assay uses a human monocyte cell line, THP-1 (ATCC TIB202) (Ogunkolade et al., Acta Trop, 47: 171-176 (1990)). Exponentially growing THP-1 ($5 \times 10^5$ cells/mL) were differentiated into macrophages by treatment with 0.1 µM Phorbol Myristate Acetate (PMA) at 37° C. for 48 h. After activation by PMA, cells were washed and incubated with stationary phase *L. donovani* promastigotes (strain 1S, clone 2D (MHOM/SD/62/1S-c12D)) at a macrophage/promastigote ratio of 1/15. After 4 hours of incubation at 37° C., the non-internalized promastigotes were removed by 2-3 successive washes and compounds of interest were added to the cultures. The activity of corifungin was tested in a dose response study: compounds were serially diluted 2-fold in water with final assay concentrations ranging from 10 µM to 0.005 µM. Amphotericin B (2 µM final concentration) and water were added to the culture as positive and negative controls respectively. Cultures were incubated at 37° C. for 72 hours. Cells were then fixed with formaldehyde and stained with the DNA marker DAPI (4',6'-diamidino-2-phenylindole) allowing the visualization of host cell nuclei and parasite kinetoplasts. Images acquired with an INCell Analyzer 1000 automated epi-fluorescent microscope (G.E. Healthcare) showed a significant size difference between these two organelles. This feature was exploited for image segmentation and determination of the number of parasites and host cells for each condition as shown in FIGS. 25 and 26. The ratio of parasite DNA to host nuclei was selected as the measurement output. Percentage inhibition of parasite growth was calculated based on positive and negative controls.

Results

FIG. 25 shows infection of THP-1 cells with *L. donovani*. FIGS. 25(A), (B), (C), and (D) depict the detection and segmentation of the THP-1 host cell and *L. donovani* intracellular amastigotes. The images were obtained with the INCell Analyzer 1000 (20×) of THP-1 cells infected with *L. donovani* and treated with 1% DMSO (FIG. 25(A) and (B)) or 2 µM amphotericin B (FIGS. 25(C) and (D)). Segmentation of host cell nuclei and parasite kinetoplast were imaged using the INCell developer toolbox software (FIGS. 25(B) and (D)). The large outlines in FIGS. 25(B) and (D) depict the host cell nuclei and borders representing the boundaries of the host cells. The outlines of the small granules within the host cells in FIG. 25(B) represent the parasite knetoplast.

FIG. 25(E) depicts the evolution of the ratio of parasites to host cells and the number of THP-1 host cells in a 72-hour time course for amphotericin B-treated samples. THP-1 and *L. donovani* were counted at several time points after infection using an INCell 1000. The white squares represent the average number of host nuclei per well (n=8); the black circles represent the average number of parasites counted per well divided by the number of host nuclei per well (n=8). As demonstrated in FIG. 25(E), the ratio of parasite to host cell increased over the course of *L. donovani* infection and the number of host cells remained essentially constant.

FIG. 26 shows the effect of corifungin on *L. donovani* intracellular growth and THP-1 host cell growth. FIG. 26(A) shows a dose response curve for corifungin plotting the percentage of parasite growth inhibition. Values represent the mean for two independent experiments.

Corifungin inhibited parasite growth at 10 µM (100% growth inhibition). Its $IC_{50}$ against *L. donovani* intracellular amastigotes was 0.09 µM, which is comparable to that observed for amphotericin B ($IC_{50}$ calculated for amphotericin B was 0.05 µM) (see FIG. 26 (A)). These results indicated a very potent in vitro activity of corifungin against *L. donovani*.

FIG. 26(B) compares the number of THP-1 macrophages infected with *L. donovani* following treatment with 10 µM corifungin, 5 µM corifungin, 1 µM corifungin, 2 µM amphotericin B, and water. Corifungin at the highest concentration tested (10 µM) did not affect the number of THP-1 per well, excluding a major toxic effect of the compound towards the host cells (see FIG. 26(B)).

In Vivo Analysis
Methodology

The in vivo efficacy of corifungin was evaluated in a mouse model of visceral leishmaniasis (Seifert, Antimicrob Agents Chemother 50: 73-79 (2006)). *L. donovani* promastigotes ($10^7$/mice) were injected intravenously. Seven days post-infection, the mice were treated either with water or with corifungin at 30 mg/kg (3 mice per group). Corifungin was administered intraperitoneally, daily for 5 days. The mice were weighted and sacrificed three days after completion of treatment (15 days post-infection). Parasite burden in liver tissue was quantified by quantitative limiting dilution culture: livers were homogenized and four-fold serial dilutions of the homogenized tissue suspension were then plated and cultured at 26° C. for 3 weeks. The wells were examined for viable promastigotes at 3-day intervals, and the reciprocal of the highest dilution which was positive for parasites was considered to be the concentration of parasites (Melby, et al., Infect Immun 66: 18-27 (1998)).

Results

Figure 27:
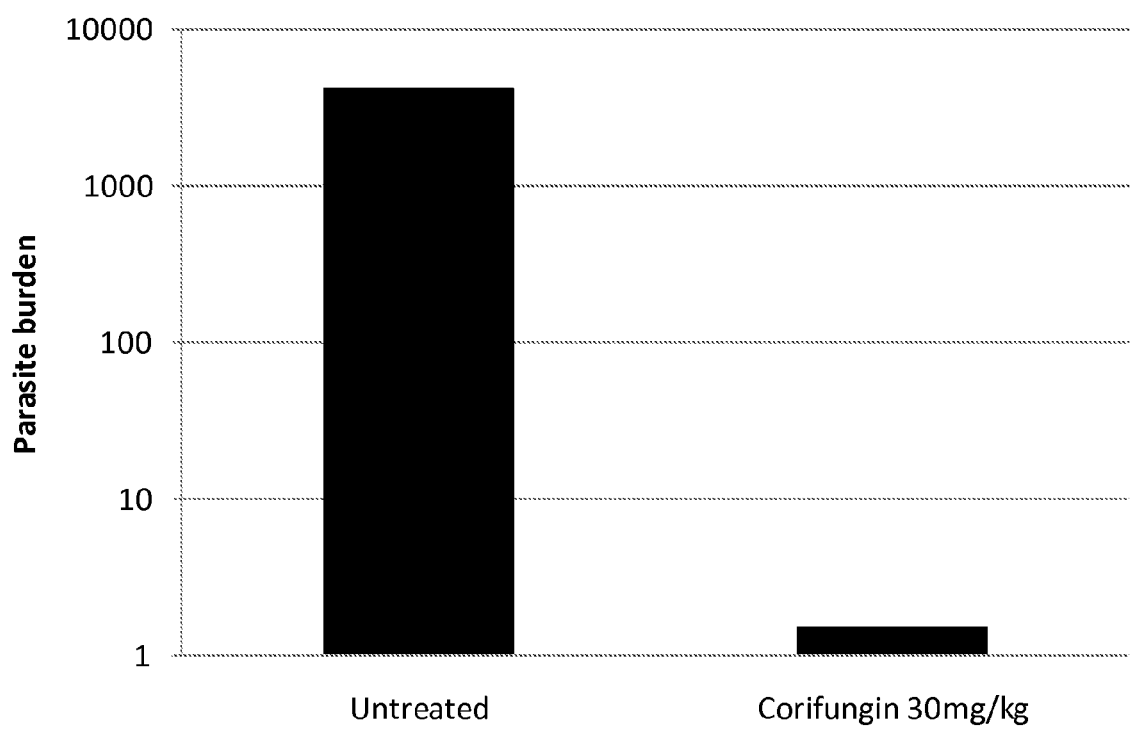
FIG. 27 shows the in vivo efficacy of corifungin in a mouse model of Leishmaniasis. Balb/c mice were infected with $10^7$ *L. donovani* promastigotes.

FIG. 27 shows the in vivo efficacy of corifungin in a mouse model of Leishmaniasis. The data points represent the parasite burdents from individual treated or untreated infected mice. Data are presented as mean±SD (n=3). As shown in FIG. 27, corifungin at 30 mg/kg completely inhibited parasite growth. Thus, corifungin was demonstrated to be active against *L. donovani* both in vitro and in vivo. Its $IC_{50}$ in vitro was comparable to amphotericin B.

EXAMPLE 8

Topical Treatment of Onychomycosis Using Corifungin

Dermatologic Evaluation by a Clinical Podiatrist:

Patient has been complaining about discolored fungused toenails, especially the right hallux. The problem has persisted for awhile. It's somewhat painful and uncomfortable. Patient has also some problems with the right thumb and some of her lesser digits as well.

Some lysis and greenish discoloration of the right thumbnail, dystrophy of the right hallux with subungual debris and hyperkeratosis. Mild OM of the left and some of the lesser digits bilaterally. About 6 nails total are involved. Skin color, moisture, temperature and texture are essentially unremarkable. No evidence of petachiae, ecchymosis or eruptions is noted. Interspaces are clear, no signs of tines noted. No sign of intertrigo is noted. Skin temperature is warm to warm proximal to distal. There are no plantar lesions noted. No atrophic skin changes are noted. No evidence of any stasis dermatitis or pigmentations is noted. No eczema is noted.

Toenail fungus infection, which has not been responsive to PENLAC® and LAMISIL®. PENLAC® NAIL LACQUER (ciclopirox) Topical Solution, 8%, is prescribed as a component of a comprehensive management program for onychomycosis (nail fungus infection). Removal of the unattached, infected nail, as frequently as monthly, by a health care professional, weekly trimming by the patient, and daily application of the medication are all integral parts of this therapy. Ciclopirox (also called LOPROX®, PENLAC® and STIEPROX®) is a synthetic antifungal agent for topical dermatologic use. It is currently being investigated as an alternative treatment to ketoconazole for seborrhoeic dermatitis as it suppresses growth of the yeast *Malassezia furfur*. Initial results show similar efficacy to ketoconazole with a relative increase in subjective symptom relief due to its inherent anti-inflammatory properties. LAMISIL® (terbinafine hydrochloride tablets). Oral 250 mg tablets are often prescribed for the treatment of onychomycosis of the toenail or fingernail due to the dermatophyte *Tinea unguium*. Fungal nail infections are located deep under the nail in the cuticle to which topically applied treatments are unable to penetrate in sufficient amounts. The tablets may, rarely, cause hepatotoxicity, so patients are warned of this and may be monitored with liver function tests. Terbinafine hydrochloride is a synthetic allylamine antifungal; highly lipophilic in nature and tends to accumulate in skin, nails, and fatty tissues.

Treatment Prescribed

Since the toenail infection was non-responsive to PENLAC® or LAMISIL®, a 1 mg/ml (water solution) of corifungin was swabbed to the infected toe twice daily for 1 week.

Results

After one month, a podiatrist checked the patient made the following observations: Both hallux nails are improving. There is in growing of the nail, but these are asymptomatic. The nail plates themselves appear to be improving.

This EXAMPLE demonstrates that corifungin effectively treats fungal infections of the toenail when topically administered.

EXAMPLE 9

Corifungin Formulations

This EXAMPLE describes two exemplary corifungin formulations that exhibit advantageously high absorption into small intestinal mucosa. In each formulation, absorption is improved by the use of a permeation enhancer. In the first formulation, corifungin was formulated with 0.5% (m/v) of the permeation enhancer, chitosan-4-thiobutylamidine (chitosan-TBA), and 5% (m/v) glutathione. In the second formulation, corifungin was formulated with 0.5% (m/v) of the permeation enhancer, chitosan, and 5% (m/v) glutathione. For each formulation, the components were homogenized and directly pressed into tablets. The effect of each formulation was evaluated by determining the quantity of rhodamine that was passed through a sample of small intestinal mucosa.

Figure 28:
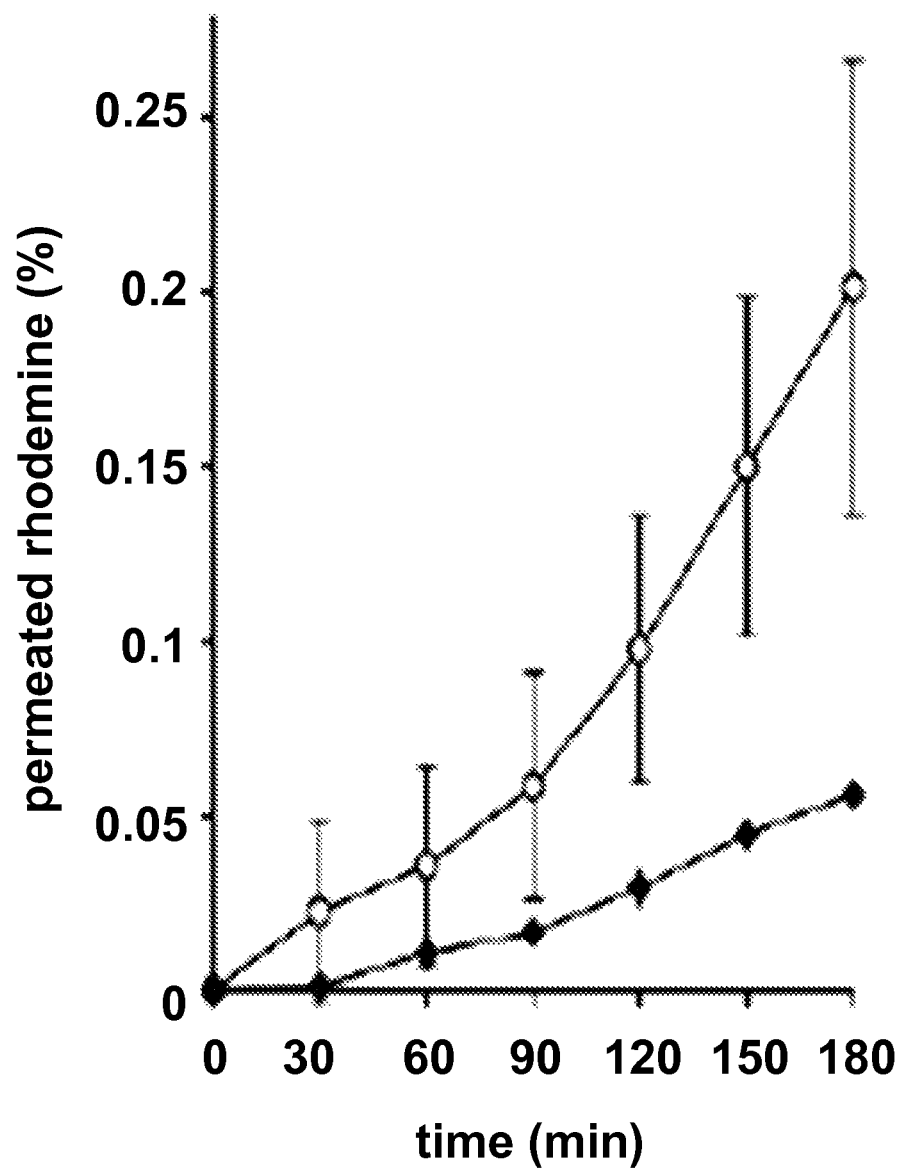
FIG. 28 shows the permeation-enhancing effect of chitosan-4-thiobutylamidine (chitosan-TBA) with glutathione (○) compared with unmodified chitosan (♦) on small intestinal mucosa.

As shown in FIG. 28, the first and second formulations significantly enhanced the permeation of the small intestinal mucosa. In particular, the first formulation comprising chitosan-4-thiobutylamidine had a particularly significant enhancement on membrane permeation.

What is claimed:

1. A method of alleviating, arresting, or inhibiting symtoms of, or conditions associated with, onychomycosis in a subject, the method comprising orally administering to the subject an effective amount of a compound of Structure (III):

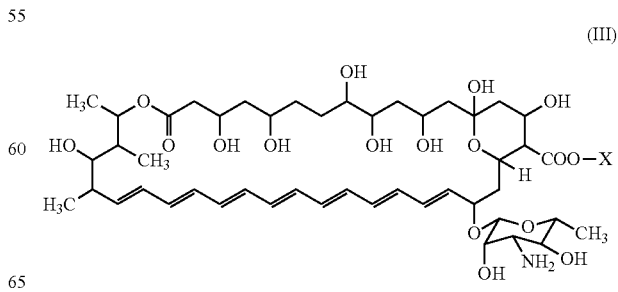

or a pharmaceutically acceptable isomer thereof, wherein:
X is a sodium.
2. The method of claim 1, wherein the compound has Structure (IV):

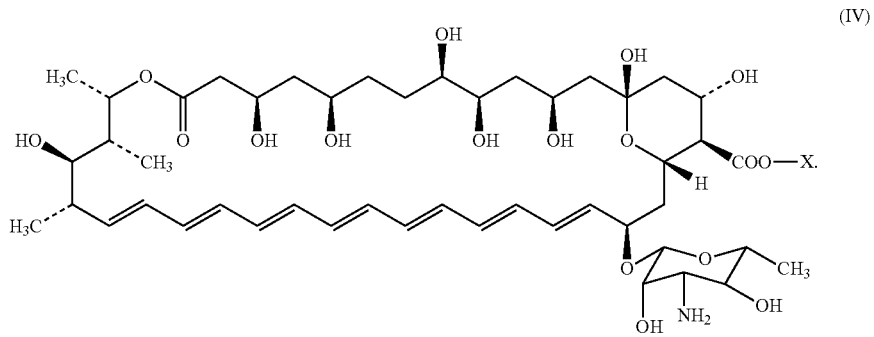

3. The method of claim 1, wherein the subject is immunocompromised.
4. The method of claim 3, wherein the subject has AIDS.
5. The method of claim 3, wherein the subject has cancer.
6. The method of claim 3, where the subject has diabetes.
7. The method of claim 3, wherein the subject has been or is being treated with immunosuppressant agents.
8. The method of claim 1, wherein the onychomycosis has been resistant to previous treatment with a topical agent.
9. The method of claim 1, wherein the onchomycosis has been resistant to previous treatment with a different systemic agent.
10. A method of alleviating, arresting, or inhibiting symptoms of, or conditions associated with, onychomycosis in a subject, the method comprising parenterally administering to the subject an effective amount of a compound of Structure (III):

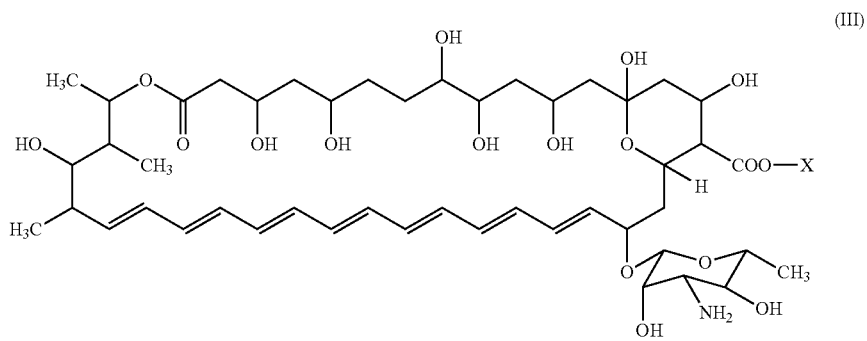

or a pharmaceutically acceptable isomer thereof, wherein:
X is sodium.
11. The method of claim 10, wherein the compound has Structure (IV):

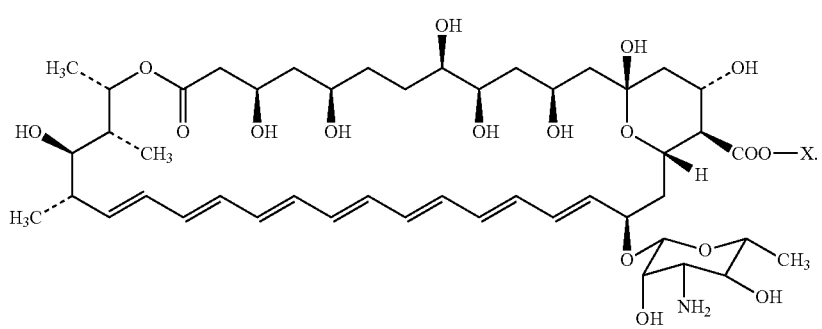
(IV)

12. The method of claim 10, wherein the subject is immunocompromised.

13. The method of claim 12, wherein the subject has AIDS.

14. The method of claim 12, wherein the subject has cancer.

15. The method of claim 12, where the subject has diabetes.

16. The method of claim 12, wherein the subject has been or is being treated with immunosuppressant agents.

17. The method of claim 10, wherein the onychomycosis has been resistant to previous treatment with a topical agent.

18. The method of claim 10, wherein the onychomycosis has been resistant to previous treatment with a different systemic agent.

* * * * *